US009758592B2

(12) United States Patent
Deshpande et al.

(10) Patent No.: US 9,758,592 B2
(45) Date of Patent: Sep. 12, 2017

(54) RECOMBINANT CELL SURFACE CAPTURE PROTEINS

(71) Applicant: Regeneron Pharmaceuticals, Inc., Tarrytown, NY (US)

(72) Inventors: Dipali Deshpande, White Plains, NY (US); Gang Chen, Yorktown Heights, NY (US); Darya Burakov, Yonkers, NY (US); James Fandl, LaGrangeville, NY (US); Thomas Aldrich, Yorktown Heights, NY (US); Vishal Kamat, Bergenfield, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 532 days.

(21) Appl. No.: 14/079,686

(22) Filed: Nov. 14, 2013

(65) Prior Publication Data

US 2014/0134719 A1    May 15, 2014

Related U.S. Application Data

(60) Provisional application No. 61/726,040, filed on Nov. 14, 2012.

(51) Int. Cl.
| | |
|---|---|
| *C07K 16/00* | (2006.01) |
| *C07K 16/42* | (2006.01) |
| *C07K 16/22* | (2006.01) |
| *C07K 16/28* | (2006.01) |

(52) U.S. Cl.
CPC .......... *C07K 16/4258* (2013.01); *C07K 16/22* (2013.01); *C07K 16/2863* (2013.01); *C07K 16/42* (2013.01); *C07K 2317/31* (2013.01); *C07K 2317/526* (2013.01); *C07K 2317/64* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,635,354 | A | 6/1997 | Kourilsky et al. |
| 5,916,771 | A | 6/1999 | Hori et al. |
| 6,080,840 | A | 6/2000 | Slanetz |
| 6,232,066 | B1 | 5/2001 | Felder et al. |
| 6,287,784 | B1 | 9/2001 | Godowski et al. |
| 6,482,655 | B1 | 11/2002 | Wei et al. |
| 6,610,485 | B1 | 8/2003 | Tsuchiya et al. |
| 6,623,957 | B2 | 9/2003 | Ward |
| 6,919,183 | B2 | 7/2005 | Fandl et al. |
| 6,927,044 | B2 | 8/2005 | Stahl |
| 7,329,731 | B2 | 2/2008 | Jakobsen |
| 7,430,476 | B2 | 9/2008 | Carr et al. |
| 7,435,553 | B2 | 10/2008 | Fandl et al. |
| 7,585,946 | B2 | 9/2009 | Fandl et al. |
| 7,700,302 | B2 | 4/2010 | Hua et al. |
| 2002/0039580 | A1 | 4/2002 | Browning et al. |
| 2002/0168702 | A1 | 11/2002 | Fandl et al. |
| 2003/0082814 | A1 | 5/2003 | Ward |
| 2005/0186623 | A1 | 8/2005 | Fandl et al. |
| 2006/0234311 | A1 | 10/2006 | Fandl et al. |
| 2009/0137416 | A1 | 5/2009 | Fandl et al. |
| 2010/0227774 | A1 | 9/2010 | Hua et al. |
| 2010/0331527 | A1 | 12/2010 | Davis et al. |
| 2011/0009280 | A1 | 1/2011 | Hufton et al. |
| 2012/0322672 | A1 | 12/2012 | Hua et al. |
| 2014/0017695 | A1 | 1/2014 | Fandl et al. |
| 2014/0072979 | A1 | 3/2014 | Fandl et al. |
| 2014/0072980 | A1 | 3/2014 | Fandl et al. |
| 2015/0160215 | A1 | 6/2015 | Fandl et al. |
| 2016/0033530 | A1 | 2/2016 | Fandl et al. |

FOREIGN PATENT DOCUMENTS

| | | |
|---|---|---|
| DE | 19900635 A1 | 7/2000 |
| EP | 0107509 A2 | 5/1984 |
| EP | 1392859 B1 | 5/2006 |
| EP | 2522724 A1 | 11/2012 |
| EP | 2949667 A2 | 12/2015 |
| WO | 94/09117 A1 | 4/1994 |
| WO | 97/29131 A1 | 8/1997 |
| WO | 99/58977 A1 | 11/1999 |
| WO | 02057423 A2 | 7/2002 |
| WO | 2014078475 A2 | 5/2014 |

OTHER PUBLICATIONS

Hamilton et al., 1993, J. Immunol. Methods. vol. 158: 107-122
Klimka et al., 2000, Brit. J. Canc. vol. 83: 252-260.*
Berglund et al., 2007, Prot. Sci. vol. 17: 606-613.*
Bonagura et al., 1998, J. Immunol. vol. 160: 2496-2505.*
Maynard et al., 2000, Ann. Rev. Biomed. Eng. vol. 2: 339-76.*
Boria, I. et al. 2008. Primer sets for cloning the human repertoire of T cell receptor variable regions. BMC Immun. 9:50.
Dangl and Herzenberg 1982. Selection of hybridomas and hybridoma variants using the fluorescence activated cell sorter. J. Immunol. Methods 52(1):1-14.
Fernandes, S. et al. 2005. Simplified fluorescent multiplex PCR method for evaluation of the T-cell receptor Vbeta-chain repertoire. Clin. Diagn. Lab. Immunol. 12(4):477-483.

(Continued)

*Primary Examiner* — Amy Juedes
(74) *Attorney, Agent, or Firm* — Honigman Miller Schwartz and Cohn LLP; Kelly T. Murphy; Jonathan P. O'Brien

(57) ABSTRACT

Recombinant cell surface capture proteins and detection molecules that are useful for isolating and detecting cells that produce a secreted heterodimeric protein of interest (POI) that has an immunoglobulin CH3 domain and/or substituted CH3 domain are provided. Recombinant cell surface capture proteins and detection molecules that isolate and detect bispecific antibodies are also provided. The invention also provides recombinant antigen-binding proteins that are capable of recognizing and binding to proteins of interest that contain a CH3 domain and/or a modified CH3 domain, such as a CH3 domain with or without amino acid substitutions at H95 and Y96 (IMGT).

8 Claims, No Drawings

(56) References Cited

OTHER PUBLICATIONS

Genevee, C. et al. 1992. An experimentally validated panel of subfamily-specific oligonucleotide primers (V alpha 1-w29N beta 1-w24) for the study of human T cell receptor variable V gene segment usage by polymerase chain reaction. Eur. J. Immunol. 22:1261-1269.
Goeddel, D.V. 1990. Systems for heterologous gene expression. Meth. Enzymol. 185:3-7.
Gorski, J. et al. 1994. Circulating T cell repertoire complexity in normal individuals and bone marrow recipients analyzed by CDR3 size spectratyping. Correlation with immune status. J. Immunol. 152(10):5109-5119.
Gray, et al. 1995. Secretion capture and report web: use of affinity derivatized agarose microdroplets for the selection of hybridoma cells. J. Immunol. Methods 182(2):155-163.
Hinz, T. and D. Kabelitz. 2000. Identification of the T-cell receptor alpha variable (TRAV) gene(s) in T-cell malignancies. J. Immnol. Methods. 246:145-148.
Hodges, E. et al. 2003. Diagnostic role of tests for T cell receptor (TCR) genes. J Clin Pathol 56:1-11.
Johnston, S.L. et al. 1995. A novel method for sequencing members of multi-gene families. Nuc. Acids Res. 23(15):3074-3075.
Laugel, B. et al. 2005. Design of soluble recombinant T cell receptors for antigen targeting and T cell inhibition. J. Bio. Chem. 280(3): 1882-1892.
Lee, et al. 2003. Microbial cell-surface display. Trends Biotechnol. 21 (1 ):45-52.
Lefranc, et al. 2003. IMGT unique numbering for immunoglobulin and T cell receptor variable domains and Ig superfamily V-like domains. Devel. Comp. Immunol. 27:57-77.
Lefranc, et al. 2005. IMGT unique numbering for immunoglobulin and T cell receptor constant domains and Ig superfamily C-like domains. Devel. Comp. Immunol. 29: 185-203.
Li, Y. et al. 2005. Directed evolution of human T-cell receptors with picomolar affinities by phage display. Nat. Biotech. 23(3):349-354.
Manz, R., et al. 1995. Analysis and sorting of live cells according to secreted molecules, relocated to a cell-surface affinity matrix. PNAS USA 92(6):1921-1925.
Martel et al., 1988. Characterization of higher avidity monoclonal antibodies produced by murine B-cell hybridoma variants selected for increased antigen binding of membrane Ig. J. Immunol. 141(5):1624-1629.
Meng, et al., 2000. Green fluorescent protein as a second selectable marker for selection of high producing clones from transfected CHO cells. Gene 242(1-2):201-207.
Moysey, R. et al. 2004. Amplification and one-step expression cloning of human T cell receptor genes. Analy. Biochem. 326:284-286.
Opekarova, et al. 2003. Specific lipid requirements of membrane proteins—a putative bottleneck in heterologous expression. Biochem. Biophys. Acta. 1610(1):11-22.
Pallavacini, et al., 1989. Rapid screening and selection of monoclonal antibodies by bivariate flow cytometric analyses. J. Immunol. Methods 117(1 ):99-106.
Pannetier, C. et al. 1995. T-cell repertoire diversity and clonal expansions in normal and clinical samples. Immunology Today 16(4):176-181.
Parks, et al. 1979. Antigen-specific identification and cloning of hybridomas with a fluorescence-activated cell sorter. PNAS 76(4):1962-1966.
Richman, SA and D.M. Kranz. 2007. Display, engineering, and applications of antigen-specific T cell receptors. Biomol. Eng. 24:361-373.
Van Dongen, JJM. et al. 2003. Design and standardization of PCR primers and protocols for detection of clonal immunoglobulin and T-cell receptor gene recombinations in suspect lymphoproliferations: Report of the BIOMED-2 Concerted Action BMH4-CT98-3936. Leukemia 17:2257-2317.
Wlodarski, M.W. et al. 2005. Pathologic clonal cytotoxic T-cell responses: nonrandom nature of the T-cell receptor restriction in large granular lymphocyte leukemia. Blood 106(8):2769-2780.
Wlodarski, M.W. et al. 2006. Molecular strategies for detection and quantitation of clonal cytotoxic T-cell responses in aplastic anemia and myelodysplastic syndrome. Blood 108(8):2632-2641.
USPTO English Translation of DE 199 00 635, 2005.
Nairn, Fluorescent Protein Tracing, Churchill Livingston, 1976, pp. 149-150.
Dean, et al. 2000. Preparation of rodent monoclonal antibodies by in vitro somatic hybridization. Monoclonal Antibodies (Shepherd and Dean, Eds). Oxford University Press. 1-23.
Barnes, et al. 2000. Advances in animal cell recombinant protein production: GS-NS0 expression system. Cytotechnology 32: 109-123.
Bebbington, et al. 1992. High-level expression of a recombinant antibody from myeloma cells using a glutamine synthetase gene as an amplifiable selectable marker. Bio/Technology 10: 169-175.
Crowe, et al. 1992. Humanized monoclonal antibody CAMPATH-1H: myeloma cell expression of genomic constructs, nucleotide sequence of cDNA constructs and comparison of effector mechanisms of myeloma and Chinese hamster ovary cell-derived material. Clin. Exp. Immunol. 87: 105-110.
Morrison, et al. 1988. Production and Characterization of Genetically Engineered Antibody Molecules. Clin. Chem. 34(9): 1668-1675.
Witzenbichler, et al. 1998. Chemotactic Properties of Angiopoietin-1 and -2, Ligands for the Endothelial-specific Receptor Tyrosine Kinase Tie2. The Journal of Biological Chemistry. 273(29): 18514-18521.
Van Vugt, et al. 1999. The FcγRIa (CD64) Ligand Binding Chain Triggers Major Histocompatibility Complex Class II Antigen Presentation Independently of Its Associated FcR γ-Chain. Blood. 94(2): 808-817.
Olsson, et al. 1987. Structure and evolution of the repetitive gene encoding streptococcal protein G. Eur. J. Biochem. 168: 319-324.
Gomi, et al.1990. The gene sequence and some properties of protein H. A novel IgG-binding protein. J Immunol. 144(10): 4046-4052.
Sondermann, et al. 2000. The 3.2-A crystal structure of the uman IgG1 Fc fragment-FcγRIII complex. Nature. 406(6793): 267-273.
Mendelsohn, et al. 1999. Protein Interaction Methods—Toward an Endgame. Science. 284: 1948-1950.
Stenroos, et al. 1998. Homogeneous time-resolved IL-2IL-2Rx Assay using Fluorescence Resonance Energy Transfer. Cytokine. 10(7): 495-499.
Selvin. 2000. The renaissance of fluorescence resonance energy transfer. Nature Structural Biology. 7(9): 730-734.
De Angelis. 1999. Why FRET over genomics? Physiol Genomics. 1(2): 93-99.
McKinney, et al. 1995. Optimizing antibody production in batch hybridoma cell culture. Journal of Biotechnology. 40: 31-48.
Boder, et al., "Directed evolution of antibody fragments with monovalent femtomolar antigen-binding affinity", PNAS, Sep. 26, 2000, vol. 97, No. 20, pp. 10701-10705.
Boder, et al., "Yeast surface display for screening combinatorial polypeptide libraries", Nature Biotechnology, Jun. 1997, vol. 15, pp. 553-557.

* cited by examiner

RECOMBINANT CELL SURFACE CAPTURE PROTEINS

CROSS-REFERENCE TO RELATED APPLICATIONS

This application claims the benefit under 35 USC §119(e) of U.S. Provisional Patent Application No. 61/726,040, filed 14 Nov. 2012, which application is herein specifically incorporated by reference in its entirety.

BACKGROUND

Sequence Listing

This application incorporates by reference the Sequence Listing submitted in Computer Readable Form as file 8600A_ST25.txt created on Oct. 30, 2013 (86,267 bytes).

Field of the Invention

The field of this invention is related to recombinant cell surface capture proteins and a methods for identifying, isolating and enriching cells that produce secreted proteins that contain heterodimers, e.g. bispecific proteins. More specifically, the cell surface capture proteins and methods allow rapid and efficient isolation of high expression recombinant antibody-producing cell lines, including rapid and efficient isolation of specific hybridomas and cells secreting heterodimeric proteins, e.g. bispecific antibodies, thereby enriching the heterodimeric species (bispecific molecule) and preferentially isolating the heterodimeric from the homodimeric species.

Prior art methods for expressing a gene of interest (GOI) in a host cell are known. Briefly, an expression vector carrying the GOI is introduced into the cell. Following stable integration, standard methods for isolating high expression cells involve collection of cell pools, hand-picking colonies from plates, isolation of single cells by limited dilution, or other methods known in the art. Pools or individual clones are then expanded and screened for production of the protein of interest (POI) by direct measurement of POI activity, by immunological detection of POI, or by other suitable techniques. These procedures are laborious, inefficient, expensive, and the number of clones that can be analyzed is usually limited to a few hundred.

The large degree of heterogeneity in protein expression by cells following stable integration requires that many individual clones be screened in an effort to identify the rare integration event that results in a stable, high expression production cell line. This requirement calls for methods that enable rapid identification and isolation of cells expressing the highest level of protein production. Moreover, the collection of clone pools or hand-picked colonies risks losing high expression cells, which often grow more slowly, to faster growing low expression cells. Therefore, a need exists for methods that allow rapid screening and isolation of individual cells capable of high level expression of a secreted POI. Where the POI contains more than one subunit, it is necessary to select preferentially for a desired heterodimeric species versus a homodimeric species.

Incorporation of flow cytometry into methods used for the isolation of stable expression cell lines has improved the capability of screening large numbers of individual clones, however, currently available methods remain inadequate for diverse reasons. Diffusion of the POI between cells of different characteristics was also a problem.

BRIEF SUMMARY

The present invention describes a high-throughput screening method for the rapid isolation of those cells that secrete protein by directly screening for the protein of interest (POI). This invention also allows for the convenient monitoring of POI expression on a single-cell basis during the manufacturing process. Furthermore, this technology can be directly applied to screening of bispecific antibody-producing cells, or any cell producing a heterodimeric protein. The technology can also be directly applied to screening of cells producing modified T cell receptors, such as, for example, cells that produce soluble forms of T cell receptors.

In one aspect, the invention provides a method of detecting and isolating cells that produce a secreted protein of interest (POI), comprising: a) constructing a nucleic acid molecule that encodes a cell surface capture molecule capable of binding a POI; b) transfecting a cell expressing the POI with the nucleic acid molecule of step a); c) detecting the surface-displayed POI by contacting the cells with a detection molecule, where in the detection molecule binds the POI; and d) isolating cells based on the detection molecule.

In various embodiments, the protein of interest includes a ligand, a soluble receptor protein, a growth factor, a fusion protein, an antibody, a bispecific antibody, an Fab, a single chain antibody (ScFv), or a fragment thereof. When the protein of interest is an antibody, the antibody is selected from the group consisting of IgM, IgG, IgA, IgD or IgE, as well as various subtypes or variants of these. In a specific embodiment, the antibody is an anti-Dll4 antibody, an anti-ErbB3 antibody, an anti-EGFR antibody, a dual-specific anti-ErbB3 /EGFR bispecific antibody, or an anti-IL-6 receptor antibody.

In more specific embodiments, the protein of interest is a growth factor selected from the group consisting of Interleukin (IL)-1, IL-2, IL-4, IL-5, IL-6, IL-7, IL-9, IL-10, IL-13, IL-15, IL-16, IL-17, IL-18, IL-21, Ciliary Neurotrophic Factor (CNTF), erythropoietin, Vascular Endothelial Growth Factor (VEGF), angiopoietin 1 (Ang-1), angiopoietin 2 (Ang-2), TNF, Interferon-gamma, GM-CSF, TGFβ, and TNF Receptor.

In various embodiments, the protein of interest comprises a variable domain of a T cell receptor. In specific embodiments, the protein of interest is a soluble T cell receptor (sTCR), or a protein comprising a T cell receptor extracellular domain fused to an Fc (TCR-Fc), In a specific embodiment, the Fc is a human Fc. In various embodiments, the protein comprises a variable domain of a T cell receptor extracellular domain. In various embodiments, the protein comprises a variable domain and a constant region of a T cell receptor extracellular domain.

The nucleic acid that encodes the protein of interest may be from any source, naturally occurring or constructed through recombinant technology, and may be selected from a DNA library.

In various embodiments, the cell surface capture molecule is a ligand-specific receptor, a receptor-specific ligand, an antibody-binding protein, an antibody or antibody fragment, such as an ScFv, or a peptide. When the capture molecule is a peptide, the peptide may be isolated from a phage display library. In more specific embodiments, the capture molecule may be Ang1, Ang2, VEGF, Tie1, Tie2, VEGFRI (Flt1), VEGFRII (Flk1 or KDR), CNTF, CNTFR-α, cytokine receptor components, fusions of two or more cytokine receptor components, or a fragment thereof. When the capture molecule is an antibody-binding protein, the antibody-binding protein may be an Fc receptor, an anti-immunoglobulin antibody, an anti-immunoglobulin (anti-Ig) ScFv, an anti-Fc antibody, anti-Fc* antibody, Protein A, Protein L, Protein G, Protein H or functional fragments thereof. As such, in some embodiments, the capture molecule is a fusion protein comprising an antigen, Protein A, or anti-Ig ScFv fused to a transmembrane domain or a GPI linker.

In various embodiments where the protein of interest comprises a T cell receptor variable domain, the cell surface capture molecule comprises an Fc receptor or a membrane-associated antigen capable of being recognized by the variable domain of the T cell receptor.

In some embodiments where the protein of interest is a heterodimeric protein, such as a heterodimeric protein having a first subunit and a second subunit, the cell surface capture molecule comprises an antigen, Protein A, or ScFv capable of binding the first subunit and not the second subunit, or such cell surface capture molecule binds the second subunit and not the first subunit.

In various embodiments where the protein of interest is an IgG1, IgG2, IgG4, or a bispecific antibody having one CH3 domain comprising a mutation the abrogates binding to protein A and the other CH3 domain capable of binding to protein A; or a fusion protein comprising an Fc region from IgG1, IgG2, IgG4, or an Fc region having one CH3 domain comprising a mutation that abrogates binding to protein A and the other CH3 domain capable of binding to protein A, the cell surface capture molecule comprises an anti-immunoglobulin ScFv, such as an anti-Fc or anti-Fc*ScFv.

In several embodiments, the methods of the invention further comprise a membrane anchor that serves to anchor the POI to the cell membrane, exposed to the outside of the cell, and thus functions as a cell surface capture molecule. In specific embodiments, the membrane anchor is a transmembrane anchor or a GPI link. Examples of specific transmembrane anchors include the transmembrane domain of an Fc receptor, such as the transmembrane domain of human FcγRI, an example of which is cited in SEQ ID NO:17. The membrane anchor may be native to the cell, recombinant, or synthetic.

In various embodiments, the protein of interest comprises a T cell receptor variable region, and the cell surface capture molecule comprises a membrane-associated antigen. In a specific embodiment, the membrane-associated antigen is a recombinant fusion protein comprising an antigen capable of being recognized by the T cell receptor variable region fused to a membrane anchor wherein the antigen is associated with the cell surface. In a specific embodiment, the recombinant fusion protein comprises an antigen fused to a transmembrane anchor or a GPI link. In another specific embodiment, the cell surface capture molecule comprises a recombinant fusion protein comprising an membrane anchor and an antigen that is capable of binding to a major histocompatibility (MHC) molecule, including but not limited to, for example, tumor antigens and self proteins of transformed phenotype.

In further embodiments, a signal sequence is added to the amino terminus of a POI, such that the protein is transported to the cell surface, and functions as a cell surface capture molecule. The signal sequence may be native to the cell, recombinant, or synthetic.

In various embodiments, a blocking molecule which binds the cell surface capture molecule is added to reduce the diffusion of the POI from the expressing cell to a neighboring cell. In another embodiment, the diffusion of the POI from the expressing cell to a neighboring cell and its adherence to that cell is reduced by increasing the viscosity of the media.

The cell isolated by the methods of the invention may be an antibody-producing cell fused to an immortalized cell. In more specific embodiments, the antibody-producing cell is a B-cell or derivative thereof. A B-cell derivative may be a plasma cell, a hybridoma, a myeloma, or a recombinant cell.

In addition, the methods of the invention are useful for identification of B-cells and derivatives thereof, or hybridomas that express secreted antibodies of a desired specificity, affinity or isotype. The invention can also be used for isolation of cells that express desired levels of an antibody or antibody fragments.

Detection of the cells with the displayed POI may be accomplished through the use of any molecule capable of directly or indirectly binding the displayed POI. Such detection molecules may facilitate the detection and/or isolation of the cells displaying the POI. In one embodiment, two molecules that bind each other and are deferentially labeled are utilized. The detection and/or isolation may be accomplished through standard techniques known in the art.

In another aspect, the invention features a method of detecting and isolating cells that produce a secreted protein of interest (POI), comprising: a) transfecting a cell with a nucleic acid that encodes a cell surface capture molecule, wherein the cell surface capture molecule is capable of binding the POI; b) transfecting the cell of a) simultaneously or subsequently with a second nucleic acid that encodes a POI wherein the POI is expressed and secreted; c) detecting the surface-displayed POI by contacting the cell with a detection molecule, which binds the POI; and d) isolating cells based on the detection molecule.

In another aspect, the invention features a method of detecting and isolating cells that produce a POI, comprising: a) detecting a cell that expresses a cell surface capture molecule in high yield; b) isolating and culturing the cell detected in (a); c) transfecting the cell in (b) with a nucleic acid that encodes a POI wherein such POI is secreted; d) detecting the surface-displayed POI by contacting the cells with a detection molecule which binds the POI; and e) isolating cells based on the detection molecule.

In another aspect, the invention provides a method of detecting and isolating cells that produce high levels of protein of interest (POI), comprising: a) transfecting cells with a nucleic acid that encodes such cell surface capture molecule capable of binding the POI, wherein the cell expresses the POI; b) detecting a cell from (a) that expresses said cell surface capture molecule in high yield; c) isolating and culturing a high yield cell; d) detecting the surface-displayed POI by contacting the cell with a detection molecule binds the POI; and e) isolating the detected cell.

In another aspect, the invention provides a method of detecting and isolating cells that produce high levels of a heterodimeric protein, comprising: (a) transfecting cells with a nucleic acid that encodes a cell surface capture molecule, which is a fusion protein comprising a membrane anchor domain and is capable of binding a first subunit of the heterodimeric protein, wherein the cell expresses the heterodimeric protein; (b) detecting a cell of (a) that expresses the surface capture molecule in high yield; (c) isolating and culturing the cell that expresses the surface capture molecule in high yield; (d) detecting the heterodimeric protein on the surface of the isolated and cultured cell of step (c) with a detection molecule that binds a second subunit of the heterodimeric protein; and (e) isolating the cell detected in step (d) that bears the detected heterodimeric protein on its surface.

In another aspect, the invention provides a method of detecting and isolating cells that produce high levels of an immunoglobulin, comprising: (a) transfecting cells with a nucleic acid that encodes a cell surface capture molecule capable of binding the immunoglobulin, wherein the cell expresses the immunoglobulin; (b) detecting a cell of (a) that expresses the surface capture molecule in high yield; (c) isolating and culturing the cell that expresses the surface capture molecule in high yield; (d) detecting the immunoglobulin on the surface of the isolated and cultured cell of step (c) with a detection molecule that binds the immunoglobulin; and (e) isolating the cell detected in step (d) that bears the detected immunoglobulin on its surface.

In some of these methods the heterodimeric protein or immunoglobulin is an antibody, and the first subunit of the heterodimeric protein or immunoglobulin comprises a heavy chain domain comprising a wild type CH3 domain. In certain embodiments, the CH3 domain comprises a histidine residue at position 95 according to the IMGT exon numbering system and a tyrosine residue at position 96 according to the IMGT exon numbering system.

In another aspect, the invention provides a method of detecting and isolating cells that produce high levels of a bispecific antibody, comprising: (a) transfecting cells with a nucleic acid that encodes a cell surface capture molecule, which is a fusion protein comprising a membrane anchor domain, such as an ScFv fusion protein and is capable of binding the bispecific antibody, wherein the cell expresses the bispecific antibody; (b) detecting a cell of (a) that expresses the surface capture molecule in high yield; (c) isolating and culturing the cell that expresses the surface capture molecule in high yield; (d) detecting the bispecific antibody on the surface of the isolated and cultured cell of step (c) with a detection molecule that binds the bispecific antibody; and (e) isolating the cell detected in step (d) that bears the detected bispecific antibody on its surface.

In another aspect, a method for detecting cells that produce a desired level of an affinity agent that comprises a T-cell receptor (TCR) variable region is provided.

In another aspect, a method for detecting cells that produce a desired level of a TCR-Fc is provided, comprising: (a) transfecting cells with a nucleic acid that encodes an Fc receptor capable of binding a TCR-Fc, wherein the cell expresses an antigen recognized by the TCR-Fc; (b) detecting a cell of (a) that expresses the TCR-Fc in high yield; (c) isolating and culturing the cell that expresses the TCR-Fc in high yield; (d) detecting the antigen on the surface of the isolated and cultured cell of step (c) with a detection molecule; and (e) isolating the cell detected in step (d) that bears the detected antigen on its surface.

In various embodiments, the TCR is selected from a human TCR and a rodent TCR such as a rat, mouse, or hamster TCR. In a specific embodiment the Fc is a human Fc. In another specific embodiment, the Fc is a human Fc and the Fc receptor is a high affinity human Fc receptor. In a specific embodiment, the high affinity human Fc receptor is a human FcγRI.

In various embodiments, the cell surface capture protein is surface-bound antigen. In a specific embodiment, the antigen is bound to the surface by fusion to a transmembrane domain or a GPI linker.

In some aspects of the method for selecting enhanced cells that produce a protein of interest, recombinant antigen-binding proteins can be used as cell surface capture proteins (CSCP), detection molecules (DM), and/or blocking molecules. Therefore, the invention provides recombinant antigen-binding proteins.

In one aspect, the invention provides a recombinant antigen-binding protein that binds a human IgG1-Fc domain, a human IgG2-Fc domain, or a human IgG4-Fc domain, or any protein that comprises for example an amino acid sequence of SEQ ID NO:26, which encodes a human Fc. In some embodiments, the recombinant antigen-binding protein binds the polypeptide with a $K_D$ of less than about 40 nM as measured in a surface plasmon resonance assay.

In some embodiments, the recombinant antigen-binding protein comprises one or more complementarity determining regions (CDRs) of a heavy chain variable region (HCVR) having an amino acid sequence that is at least 95% identical to SEQ ID NO:15, or of a light chain variable region (LCVR) having an amino acid sequence that is at least 95% identical to SEQ ID NO:16. In one case, the protein comprises a heavy chain CDR-1 (HCDR-1) having the amino acid sequence of SEQ ID NO:27, an HCDR-2 having the amino acid sequence of SEQ ID NO:28, an HCDR-3 having the amino acid sequence of SEQ ID NO:29, a light chain CDR-1 (LCDR-1) having the amino acid sequence of SEQ ID NO:30, and an LCDR-2 having the amino acid sequence of SEQ ID NO:31. In some cases, the protein comprises an HCVR having an amino acid sequence that is at least 95% identical to SEQ ID NO:15 (some of which are identical to SEQ ID NO:15) and an LCVR having an amino acid sequence that is at least 95% identical to SEQ ID NO:16 (some of which are identical to SEQ ID NO:16).

Recombinant antigen-binding proteins, which are antibodies, are useful as detection molecules (DMs).

In some embodiments, the recombinant antigen-binding protein is an ScFv fusion protein, which in some cases comprises a heavy chain variable domain with an amino acid sequence that is at least 95% identical to (or identical to) SEQ ID NO:15, a light chain variable domain with an amino acid sequence that is at least 95% identical to (or identical to) SEQ ID NO:16, and a membrane anchor domain. In one embodiment, the membrane anchor domain is derived from an Fc receptor, such as the transmembrane domain of the human FcγR1 protein, as represented by SEQ ID NO:17, or SEQ ID NO:21, which contains not only the transmembrane domain, but also the C-terminal cytoplasmic domain (SEQ ID NO:18). In one specific embodiment, the ScFv fusion protein has the amino acid sequence of SEQ ID NO:19. Recombinant antigen-binding proteins, which are ScFv fusion proteins, are useful as CSCPs and as DMs.

In another aspect, the invention provides a polynucleotide that encodes the antigen-binding protein of the preceding aspect. In one embodiment, such as in the case where the antigen-binding protein is an antibody, the polynucleotide encodes the light chain. Likewise, the polynucleotide may encode the heavy chain. In the case in which the antigen-binding protein is an ScFv fusion protein, the polynucleotide may encode the ScFv-FcγRTM-cyto fusion protein of SEQ ID NO:19. For example, the polynucleotide of SEQ ID NO: 20 encodes SEQ ID NO:19.

In another aspect, the invention provides a nucleic acid vector that encompasses the polynucleotide of the preceding aspect. In one embodiment, the vector comprises the polynucleotide, which encodes the antigen-binding protein, operably linked to an upstream promoter, and followed by a downstream polyadenylation sequence. The promoter can be any promoter, such as for example a CMV promoter. Thus in one case, the vector may contain the sequence of SEQ ID NO:25. In one embodiment, the vector may contain a nucleic acid sequence that encodes a selectable marker, such as for example neomycin resistance. In one embodiment, the vector may contain a nucleic acid sequence that encodes an energy transfer protein, such as green fluorescence protein (GFP), or a derivative thereof, such as yellow fluorescence protein (YFP). Thus in one case, the vector may contain the sequence of SEQ ID NO:24.

The vector may be circular or linear, episomal to a host cell's genome or integrated into the host cell's genome. In some embodiments, the vector is a circular plasmid, which in one specific embodiment has the nucleic acid sequence of SEQ ID NO:23 for the ScFv-FcγR-TM-cyto-encoding polynucleotide, in another specific embodiment comprises the nucleic acid sequence of the antibody heavy chain-encoding polynucleotide, and yet another specific embodiment comprises the nucleic acid sequence of the antibody light chain-encoding polynucleotide. In some embodiments, the vector is a linear construct, which may be integrated into a host cell chromosome. In one specific embodiment, the linear construct has the nucleic acid sequence of SEQ ID NO:22 for the ScFv-FcγR-TM-cyto-encoding polynucleotide. In another specific embodiment, the linear construct comprises the nucleic acid sequence of the antibody heavy chain-encoding polynucleotide. In yet another specific embodiment, the linear construct comprises the nucleic acid sequence of the antibody light chain-encoding polynucleotide.

The host cell may be any cell, prokaryotic or eukaryotic. However, in one specific embodiment, the host cell is a CHO cell, such as a CHO-K1 cell.

In another aspect, the invention provides a host cell that expresses the antigen-binding protein of the preceding aspect, and/or contains the polynucleotide or nucleic acid vector of the preceding aspects. In some embodiments, the host cell is a CHO cell. In a specific embodiment, the host cell is a CHO-K1 cell. In one embodiment, host cell is used in the production of a protein of interest, and the antigen-binding protein is used as a cell surface capture protein according to the methods disclosed in this application.

In one aspect, the invention provides a host cell useful in the production of a protein of interest. The host cell harbors a polynucleotide or nucleic acid vector of a preceding aspect, and produces an antigen-binding protein of a preceding aspect, which serves as a cell surface capture protein. The cell surface capture protein binds to the protein of interest inside the host cell, and is transported through the secretory apparatus of the cell, and is expressed on the surface of the host cell. Thus, in one embodiment, the host cell comprises a cell surface capture protein positioned in the host cell plasma membrane, with the capturing moiety facing outside of the cell. In one embodiment, the cell surface capture molecule is bound to a protein of interest, which is positioned at the plasma membrane and oriented outside of the cell.

In one embodiment, the host cell produces or is capable of producing an ScFv fusion protein that binds to a protein of interest that contains an Fc domain, which contains a histidine at IMGT position 95 and a tyrosine at IMGT position 96. Examples include IgG1, IgG2, and IgG4 proteins. In one embodiment, the ScFv fusion protein contains amino acid sequences set forth in SEQ ID NO:27, SEQ ID NO:28, SEQ ID NO:29, SEQ ID NO:30, and SEQ ID NO:31. In one specific embodiment, the ScFv fusion protein comprises the amino acid sequence of SEQ ID NO:19. In a specific embodiment, the host cell comprises a cell surface capture protein positioned at the plasma membrane and bound to an IgG1, IgG2 or IgG4, or a bispecific antibody containing at least one heavy chain of an IgG1, IgG2 or IgG4, and which may have a second heavy chain that is of another type or contains one of more amino acid substitutions.

In one aspect, the invention provides a recombinant antigen-binding protein that binds a substituted CH3 polypeptide comprising one or more amino acid substitutions selected from the group consisting of (a) 95R, and (b) 95R and 96F according to the IMGT exon numbering system, or (a') 435R, and (b') 435R and 436F according to the EU numbering system, or any protein that comprises for example an amino acid sequence of SEQ ID NO:42, which encodes a substituted human Fc (also known as Fc*). In some embodiments, the recombinant antigen-binding protein binds the polypeptide with a $K_D$ of less than about 60 nM as measured in a surface plasmon resonance assay.

In some embodiments, the recombinant antigen-binding protein comprises one or more complementarity determining regions (CDRs) of a heavy chain variable region (HCVR) having an amino acid sequence that is at least 95% identical to SEQ ID NO:38, or of a light chain variable region (LCVR) having an amino acid sequence that is at least 95% identical to SEQ ID NO:39. In one case, the protein comprises a heavy chain CDR-1 (HCDR1) having the amino acid sequence of SEQ ID NO:32, an HCDR-2 having the amino acid sequence of SEQ ID NO:33, an HCDR-3 having the amino acid sequence of SEQ ID NO:34, a light chain CDR-1 (LCDR-1) having the amino acid sequence of SEQ ID NO:35, and an LCDR-2 having the amino acid sequence of SEQ ID NO:36. In some cases, the protein comprises an HCVR having an amino acid sequence that is at least 95% identical to SEQ ID NO:38 (some of which are identical to SEQ ID NO:38) and an LCVR having an amino acid sequence that is at least 95% identical to SEQ ID NO:39 (some of which are identical to SEQ ID NO:39).

In some embodiments, the recombinant antigen-binding protein is an antibody, which comprises a heavy chain and a light chain. The heavy chain may comprise an amino acid sequence that is at least 95% identical to (or 100% identical to) SEQ ID NO:40. The light chain may comprise an amino acid sequence that is at least 95% identical to (or 100% identical to) SEQ ID NO:41. Recombinant antigen-binding proteins, which are antibodies, are useful as detection molecules (DMs).

In some embodiments, the recombinant antigen-binding protein is an ScFv fusion protein, which in some cases comprises a heavy chain variable domain with an amino acid sequence that is at least 95% identical to (or identical to) SEQ ID NO:38, a light chain variable domain with an amino acid sequence that is at least 95% identical to (or identical to) SEQ ID NO:39, and a membrane anchor domain. In one embodiment, the membrane anchor domain is derived from an Fc receptor, such as the transmembrane domain of the human FcγR1 protein, as represented by SEQ ID NO:17, or SEQ ID NO:21, which contains not only the transmembrane domain, but also the C-terminal cytoplasmic domain of SEQ ID NO:19. In one specific embodiment, the ScFv fusion protein has the amino acid sequence of SEQ ID NO:43. Recombinant antigen-binding proteins, which are ScFv fusion proteins, are useful as CSCPs and as DMs.

In another aspect, the invention provides a polynucleotide that encodes the antigen-binding protein of the preceding aspect. In one embodiment, such as in the case where the antigen-binding protein is an antibody, the polynucleotide encodes the light chain, such as for example the light chain of SEQ ID NO:41. Likewise, the polynucleotide may encode the heavy chain, such as, for example, the heavy chain of SEQ ID NO:40. In the case in which the antigen-binding protein is an ScFv fusion protein, the polynucleotide may encode the ScFv-FcγR-TM-cyto fusion protein of SEQ ID NO:43. Representative exemplar polynucleotides include those polynucleotides of SEQ ID NO:49, 50 and 51, respectively.

In another aspect, the invention provides a nucleic acid vector that encompasses the polynucleotide of the preceding aspect. In one embodiment, the vector comprises the polynucleotide, which encodes the antigen-binding protein, operably linked to an upstream promoter, and followed by a downstream polyadenylation sequence. The promoter can be any promoter, such as for example a CMV promoter. Thus in one case, the vector may contain the sequence of SEQ ID NO:47. In one embodiment, the vector may contain a nucleic acid sequence that encodes a selectable marker, such as for example neomycin resistance. In one embodiment, the vector may contain a nucleic acid sequence that encodes an energy transfer protein, such as green fluorescence protein (GFP), or a derivative thereof, such as yellow fluorescence protein (YFP). Thus in one case, the vector may contain the sequence of SEQ ID NO:46.

The vector may be circular or linear, episomal to a host cell's genome or integrated into the host cell's genome. In some embodiments, the vector is a circular plasmid, which in one specific embodiment has the nucleic acid sequence of SEQ ID NO:44 for the ScFv-FcγR-TM-cyto-encoding polynucleotide, in another specific embodiment has the nucleic acid sequence of the antibody heavy chain-encoding polynucleotide, and yet another specific embodiment has the nucleic acid sequence of the antibody light chain-encoding polynucleotide. In some embodiments, the vector is a linear construct, which may be integrated into a host cell chromosome. In one specific embodiment, the linear construct comprises the nucleic acid sequence of SEQ ID NO:51 for the ScFv-FcγR-TM-cyto-encoding polynucleotide. In another specific embodiment, the linear construct comprises the nucleic acid sequence of SEQ ID NO:50 for the antibody heavy chain-encoding polynucleotide. In yet another specific embodiment, the linear construct comprises the nucleic acid sequence of SEQ ID NO:49 for the antibody light chain-encoding polynucleotide.

The host cell may be any cell, prokaryotic or eukaryotic. However, in one specific embodiment, the host cell is a CHO cell, such as a CHO-K1 cell.

In another aspect, the invention provides a host cell that expresses the antigen-binding protein of the preceding aspect, and/or contains the polynucleotide or nucleic acid vector of the preceding aspects. In some embodiments, the host cell is a CHO cell. In a specific embodiment, the host cell is a CHO-K1 cell. In one embodiment, host cell is used in the production of a protein of interest, and the antigen-binding protein is used as a cell surface capture protein according to the methods disclosed in this application.

In one aspect, the invention provides a host cell useful in the production of a protein of interest. The host cell harbors a polynucleotide or nucleic acid vector of a preceding aspect, and produces an antigen-binding protein of a preceding aspect, which serves as a cell surface capture protein. The cell surface capture protein binds to the protein of interest inside the host cell, and is transported through the secretory apparatus of the cell, and is expressed on the surface of the host cell. Thus, in one embodiment, the host cell comprises a cell surface capture protein positioned in the host cell plasma membrane, with the capturing moiety facing outside of the cell. In one embodiment, the cell surface capture molecule is bound to a protein of interest, which is positioned at the plasma membrane and oriented outside of the cell.

In one embodiment, the host cell produces or is capable of producing an ScFv fusion protein that binds to a protein of interest that contains an Fc domain, which contains an arginine at IMGT position 95 and a phenylalanine at IMGT position 96 (Fc*). Examples include IgG3 and substituted CH3 regions of IgG1, IgG2, and IgG4 proteins. In one embodiment, the ScFv fusion protein contains amino acid sequences set forth in SEQ ID NO:32, SEQ ID NO:33, SEQ ID NO:34, SEQ ID NO:35, SEQ ID NO:36 and SEQ ID NO:37. In one specific embodiment, the ScFv fusion protein comprises the amino acid sequence of SEQ ID NO:43. In a specific embodiment, the host cell comprises a cell surface capture protein positioned at the plasma membrane and bound to an IgG3 or a substituted IgG1, IgG2 or IgG4, which contain the arginine at IMGT position 95 and phenylalanine at IMGT position 96 ("Fc*"), or a bispecific antibody containing at least one heavy chain of a the Fc* type and the other heavy chain of the IgG1, IgG2 or IgG4 wildtype.

In another aspect, the invention provides a method of detecting, isolating, or enriching for a cell that stably expresses a protein of interest (POI). The method includes the step of expressing in the host cell a cell surface capture protein (CSCP) and a POI. According to this method, the CSCP binds to a "first site" on the POI to form a CSCP-POI complex inside the host cell. This CSCP-POI complex is then transported through the secretory system of the host cell, and is secreted from the cell. Since the CSCP contains a membrane binding domain (e.g., SEQ ID NO:17), the CSCP-POI complex is displayed on the surface of the host cell, with the POI exposed outside of the cell. According to the method, the host cell is then contacted with a detection molecule (DM), which binds to a "second site" on the POI. Those cells that bind the DM are selected for identification, isolation, pooling, and/or enrichment. In one embodiment, the DM-bound host cell is selected by fluorescence activated cell sorting.

In one embodiment, the method also includes the step of contacting the cell with a blocking molecule prior to selecting the host cell. The blocking molecule binds to any CSCP that is not bound to the POI. The blocking molecule does not bind to the CSCP-POI complex.

In some embodiments, the POI contains multiple subunits, such as an antibody that comprises two heavy chains and two light chains. In that case, the first site on the POI may reside on a first subunit, and the second site on the POI may reside on a second subunit. In some embodiments, the POI contains multiple subunits, such as a heterodimeric protein. In the case of a heterodimeric protein, the first site on the POI may reside on a first subunit, such as a first receptor, and the second site on the POI may reside on a second subunit, such as a second receptor or coreceptor. In some embodiments, the heterodimeric proteins are different receptors that interact to form the heterodimer. Where the POI is an antibody, the first site on the POI may reside on a first heavy chain, and the second site on the POI may reside on a second heavy chain. In some embodiments, the antibody contains subunits that differ by at least one amino acid, such as an antibody having at least one heavy chain with a wild type CH3 domain and the other heavy chain having at least one amino acid substitution in the CH3 domain. In this case, the CSCP may be an antigen-binding protein as described herein, such as an antigen or anti-Ig ScFv fusion protein. Here, the detection molecule (DM) may comprise a labeled recombinant antigen-binding protein as described herein, such as a labeled antigen or anti-Ig antibody or ScFv molecule.

In some cases, for example where the POI is a bispecific antibody, the first site may reside on a heavy chain that has a CH3 domain containing a histidine residue at position 95 according to the IMGT exon numbering system and a tyrosine residue at position 96 according to the IMGT exon numbering system (Fc). Then, the second site may reside on a heavy chain that has a CH3 domain containing an arginine residue at position 95 according to the IMGT exon numbering system and a phenylalanine residue at position 96 according to the IMGT exon numbering system (Fc*). In this case, the CSCP may be an antigen-binding protein described in a preceding aspect, such as an ScFv fusion protein containing the amino acid sequences of SEQ ID NO:27, SEQ ID NO:28, SEQ ID NO:29, SEQ ID NO:30, and SEQ ID NO:31; which in a specific embodiment comprises SEQ ID NO:19. Here also, the detection molecule (DM) may comprise a labeled recombinant antigen-binding protein described in a preceding aspect, such as an antibody or ScFv molecule containing the amino acid sequences of SEQ ID NO:32, SEQ ID NO:33, SEQ ID NO:34, SEQ ID NO:35, SEQ ID NO:36, and SEQ ID NO:37; which in a specific embodiment comprises either SEQ ID NO:40 and SEQ ID NO:41 (anti-Fc* antibody), or SEQ ID NO:43 (ScFv*). Here, the blocking molecule may be an Fc polypeptide (e.g., single chain), such as hFc, or any molecule that can bind to the CSCP without also binding to the DM. In one embodiment, the detection molecule may be a labeled anti-human IgG F(ab')$_2$.

In other cases in which the POI is a bispecific antibody, the first site may reside on a heavy chain that has a CH3 domain containing an arginine residue at position 95 according to the IMGT exon numbering system and a phenylalanine residue at position 96 according to the IMGT exon numbering system (Fc*). Then, the second site may reside on a heavy chain that has a CH3 domain containing a histidine residue at position 95 according to the IMGT exon numbering system and a tyrosine residue at position 96 according to the IMGT exon numbering system. In this case, the CSCP may be an antigen-binding protein described in a preceding aspect, such as an ScFv fusion protein containing the amino acid sequences of SEQ ID NO:32, SEQ ID NO:33, SEQ ID NO:34, SEQ ID NO:35, SEQ ID NO:36, and SEQ ID NO:37; which in a specific embodiment comprises SEQ ID NO:43. Here also, the detection molecule (DM) may comprise a labeled recombinant antigen-binding protein described in a preceding aspect, such as an antibody or ScFv molecule containing the amino acid sequences of SEQ ID NO:27, SEQ ID NO:28, SEQ ID NO:29, SEQ ID NO:30, and SEQ ID NO:31; which in a specific embodiment comprises either a heavy chain and a light chain (anti-hFc antibody), or SEQ ID NO:19 (ScFv). Here, the blocking molecule may be an Fc* polypeptide (e.g., single chain), or any molecule that can bind to the CSCP without also binding to the DM. In one embodiment, the detection molecule may be a labeled anti-human IgG F(ab')$_2$.

In some aspects, the invention provides a method of detecting or isolating a cell that stably expresses a heterodimeric protein comprising the steps of (a) expressing in a host cell a cell surface capture protein (CSCP) and a heterodimeric protein, wherein (i) the CSCP binds to a first site on the heterodimeric protein to form a CSCP– heterodimeric protein complex inside the host cell, (ii) the CSCP– heterodimeric protein complex is transported through the host cell, and (iii) then displayed on the surface of the host cell; (b) contacting the host cell with a detection molecule, wherein the detection molecule binds to a second site on the heterodimeric protein; and (c) selecting the host cell which binds the detection molecule. In some embodiments, the heterodimeric protein comprises multiple subunits and the first site on the heterodimeric protein resides on a first subunit, and the second site resides on the heterodimeric protein resides on a second subunit. In some embodiments, the cell surface capture molecule comprises an antigen, Protein A, or ScFv capable of binding the first subunit and not the second subunit.

In one aspect, the invention provides a method of producing a bispecific antibody comprising the step of expressing in a host cell a cell surface capture protein ("CSCP"), an antibody light chain, a first antibody heavy chain, which contains a CH3 domain comprising a histidine at IMGT position 95 and a tyrosine at IMGT position 96, and a second antibody heavy chain, which contains a CH3 domain comprising an arginine at IMGT position 95 and a phenylalanine at IMGT position 96. While inside the host cell, the CSCP binds to the first antibody heavy chain but does not bind to the second antibody heavy chain, the second antibody heavy chain binds to the first antibody heavy chain, and the light chains bind to the heavy chains, thus forming a CSCP-Antibody ternary complex. This ternary complex is secreted and presented onto the surface of the host cell. The host cell may be contacted with a blocking molecule, which binds to a CSCP on the cell surface, but only in those situations in which the CSCP is not bound to the antibody-of-interest, i.e., an "empty" CSCP. The host cell is then contacted with a DM that binds to or is capable of binding to the second antibody heavy chain. The host cell that binds the DM is identified, selected, and/or pooled. In some embodiments, the host cells that bind the DM are selected, pooled, cultured and expanded, and then subjected to another round of expression, detection, selection, pooling and expansion. This process may be reiterated multiple times to enrich for the production of high titers of bispecific antibodies.

In one embodiment, the CSCP employed in the method is an ScFv-fusion protein containing the amino acid sequences of SEQ ID NO:27, SEQ ID NO:28, SEQ ID NO:29, SEQ ID NO:30, and SEQ ID NO:31. In one embodiment, the CSCP comprises the amino acid sequence of SEQ ID NO:19. In one embodiment, the DM employed in the method is a protein containing the amino acid sequences of SEQ ID NO:32, SEQ ID NO:33, SEQ ID NO:34, SEQ ID NO:35, SEQ ID NO:36, and SEQ ID NO:37. In one embodiment, the DM is an antibody comprising a heavy chain sequence of SEQ ID NO:40 and a light chain sequence of SEQ ID NO:41. In another embodiment, the DM is an ScFv fusion protein containing the amino acid sequence of SEQ ID NO:43. A label, for example a fluorescent moiety like FITC or Alexa Fluor® 488, may be attached to the DM. Fluorescence activated cell sorting may be used as the detection and selection means.

In an alternative embodiment, the method of producing a bispecific antibody comprises the step of expressing in a host cell a cell surface capture protein ("CSCP"), an antibody light chain, a first antibody heavy chain, which contains a CH3 domain comprising an arginine at IMGT position 95 and a phenylalanine at IMGT position 96 (Fc*), and a second antibody heavy chain, which contains a CH3 domain comprising a histidine at IMGT position 95 and a tyrosine at IMGT position 96. While inside the host cell, the CSCP binds to the first antibody heavy chain but does not bind to the second antibody heavy chain, the second antibody heavy chain binds to the first antibody heavy chain, and the light chains bind to the heavy chains, thus forming a CSCP-Antibody ternary complex. This ternary complex is secreted and presented onto the surface of the host cell. The host cell may be contacted with a blocking molecule, which binds to a CSCP on the cell surface, but only in those situations in which the CSCP is not bound to the antibody-of-interest, i.e., an "empty" CSCP. The host cell is then contacted with a DM that binds to or is capable of binding to the second antibody heavy chain. The host cell that binds the DM is identified, selected, and/or pooled. In some embodiments, the host cells that bind the DM are selected, pooled, cultured and expanded, and then subjected to another round of expression, detection, selection, pooling and expansion. This process may be reiterated multiple times to enrich for the production of high titers of bispecific antibodies.

In one embodiment of this alternative embodiment, the CSCP employed in the method is an ScFv-fusion protein containing the amino acid sequences of SEQ ID NO:32, SEQ ID NO:33, SEQ ID NO:34, SEQ ID NO:35, SEQ ID NO:36, and SEQ ID NO:37. In one embodiment, the CSCP comprises the amino acid sequence of SEQ ID NO:43. In one embodiment, the DM employed in the method is a protein containing the amino acid sequences of SEQ ID NO:27, SEQ ID NO:28, SEQ ID NO:29, SEQ ID NO:30, and SEQ ID NO:31. In one embodiment, the DM is an antibody comprising a heavy chain sequence and a light chain sequence. In another embodiment, the DM is an ScFv fusion protein containing the amino acid sequence of SEQ ID NO:19. A label, for example a fluorescent moiety like FITC or Alexa Fluor® 488, may be attached to the DM. Fluorescence activated cell sorting may be used as the detection and selection means.

In both the first embodiment and the alternative embodiment, the host cell, which is the product of the iterative selection, pooling and expansion, is capable of producing, or does produce bispecific antibody at a titer of at least 2 g/L, wherein the bispecific antibody species (Fc/Fc*) represents at least 40% by mass of the total antibody produced by the host cell (Fc/Fc+Fc*/Fc*+Fc/Fc*).

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

The method of the invention provides substantial advantages over current methods for isolation and identification of protein-secreting cells. For example, cells that secrete antibodies may be rapidly and conveniently isolated based on desired specificity, avidity, or isotype. Furthermore, the amount of secreted protein produced may be directly quantified, unlike many methods in the prior art wherein production of secreted protein is indirectly quantified.

Recently, two additional methods that utilize flow cytometry have been developed for the high throughput isolation of stable high expression cell lines. The first method involves modification of the expression plasmid to include a transcriptional read out for the GOI mRNA. This is most often accomplished by inserting an internal ribosomal entry site (IRES) and a gene whose protein product is easily monitored by flow cytometry, most frequently green fluorescent protein (GFP), between the stop codon of the GOI and the terminal poly A site (Meng et al. (2000) Gene 242:201). The presence of an IRES allows the POI and GFP to be translated from the same mRNA. Therefore, the expression level of the GFP gene is indirectly related to the mRNA level for the GOI. Clones that accumulate the GFP at high levels are isolated by flow cytometry and then screened for POI production. Because this method depends on the coupling of GOI expression to the reporter gene by use of an IRES in a recombinant construction, it is not applicable to the isolation of hybridomas.

The use of flow cytometry in the isolation of expression clones allows for the rapid analysis of large numbers of clones in a high throughput format. Moreover, use of flow cytometry significantly reduces the direct handling of cells. Unfortunately, the level of GFP production is not a direct measure of the production level of the POI. Various mechanisms may uncouple the production of secreted POI from accumulation of GFP. Differences in production of the POI and the GFP reporter may result from differences in the translation efficiency of the two genes, secretion efficiency of the POI, or stability of the polycistronic mRNA.

Another method that uses flow cytometry to isolate expression clones involves encapsulation of cells within agarose microdrops (Weaver et al. (1990) Methods Enzymol. 2:234). In this method biotinylated antibodies specific for the POI are bound to the biotinylated agarose through streptavidin such that secreted POI is captured and retained within the microdrop (Gray et al., (1995) J. Immunol. Methods 182:155). The trapped POI is detected by immunostaining with an antibody specific for the POI. To reduce the encapsulating agarose from absorbing POI secreted from adjacent cells, the cells are placed in a low-permeability medium. Those cells with the highest antibody staining of the POI in the embedding agarose are identified and isolated by flow cytometry. The gel microdrop approach screens cells directly for their ability to secrete POI, rather than indirectly screening for expression of GOI mRNA, but requires the availability of suitable antibodies for trapping and staining the secreted POI and the procedure requires special equipment to generate the agarose gel microdrops. Moreover, some cells may be sensitive to the encapsulation process.

A variation of this method circumvents the requirement for embedding cells in a matrix by directly binding an antibody, specific for the POI, to the cell surface (Manz et al. (1995) PNAS 92:1921-1925). In this method, non-specific biotinylation of cell surface proteins with biotin-hydroxysuccinimide ester is followed by contact with a streptavidin-conjugated antibody capable of binding the POI. Cells secreting the POI become decorated with the POI which is then detected with an appropriately labeled second antibody. However, diffusion of POI between neighboring cells is problematic, and this method also requires a high viscosity medium to reduce diffusion of POI away from expressing cells. Because these high viscosity media are required for discriminating cells, the cells must be washed and placed in a medium suitable for cell sorting if so desired.

The problems associated with identification and isolation of high expression recombinant cell lines especially applies to the isolation of hybridomas that express an antibody of interest. However, the identification of useful hybridomas includes several additional problems; they must be screened first for antigen-binding activity, then for immunoglobulin isotype. Moreover, GFP-based methods are not applicable to the identification and isolation of hybridomas because construction of hybridomas does not include a recombinant construct such that expression of the antibody genes can be linked to a transcriptional reporter such as GFP. Hybridoma screening is a slow, laborious endeavor where the number of clones screened is limited by existing technologies.

The instant invention describes a novel and previously unknown method of identifying and isolating cells that produce secreted proteins. The invention is based on the production of a cell line that expresses a molecule, localized to the cell surface, which binds the POI. The cell surface-displayed POI can then be detected by labeling with various detection molecules. The amount of POI displayed on the cell surface, under specific conditions, is a direct measure of the total amount of POI secreted. POI producers may then be isolated from non-producers, and levels of production or POI characteristics may be differentiated. The advantage of the invention is that it directly quantifies the secreted POI rather than indirectly measuring the mRNA.

This invention relates to the construction or use of cells that express cell surface capture molecules which bind various secreted POIs in the same cell that produces the POI. As the cell secretes the POI, these cell surface capture molecules bind it, or complexes of POI and cell surface capture molecules may form intracellularly and then get secreted. Binding may occur in an autocrine manner or while being secreted. The cells that produce the secreted POI may then be identified and isolated. Such identification and isolation may be based on characteristics of the POI, production of the POI or lack thereof, or by specified levels of production. The cell surface capture molecule and/or the POI may be produced by the cell in its native state, or the cell surface capture molecules and/or the POI may be recombinantly produced. Through the construction or use of such a cell, any secreted protein may be captured by the cell surface capture molecule provided there is a corresponding affinity between the two. As explained further, any molecule may be manipulated such that it can be used as a cell surface capture molecule. Therefore, this invention may be utilized to isolate any cell that secretes a protein.

Most any protein has the capacity to function as a cell surface capture molecule as described by the invention. What is necessary is the ability of the desired protein to be anchored to the cell membrane and exposed to the extracellular space. If the desired cell has a signal sequence then only a membrane anchor, including but not limited to a transmembrane anchor or a GPI linkage signal, need be added to the cell surface capture molecule such that it remains anchored in the cell membrane exposed to the outside of the cell. Furthermore, if the desired protein lacks a signal sequence, a signal sequence may be added to the amino terminus of the desired protein, such that it is transported to the cell surface. A signal sequence and a membrane anchor may be native to the cell, recombinant, or synthetic.

Cells often secrete a wide variety of proteins, endogenously or following the introduction of recombinant DNA. Any secreted protein may be identified and the cell producing it may be isolated according to the method of this invention. Such secreted proteins include but are not limited to growth factors, growth factor receptors, ligands, soluble receptor components, antibodies, bispecific antibodies, recombinant Trap molecules, Fc-containing fusion proteins, sTCRs, TCR-Fc's, and peptide hormones. Such secreted proteins may or may not be recombinant. That is, the secretion of some proteins of interest from the desired cell may not require the introduction of additional nucleotide sequences. For example, the secretion of antibodies from B-cells or plasma cells is not the result of introduction of recombinant nucleotide sequences into the B-cell or plasma cell. Recombinant secreted proteins may be produced by standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). These secreted proteins are useful for many commercial and research purposes. This invention encompasses the production of such secreted proteins through the methodologies of the invention. Detection of the cells with the displayed POI may be accomplished through the use of any molecule capable of directly or indirectly binding the displayed POI. Such detection molecules may facilitate the detection and/or isolation of the cells displaying the POI.

The invention is applicable to the isolation of, inter alia, a) ligand-producing cells by using the ligand-specific receptor as the cell surface capture molecule, b) soluble receptor-producing cells by using a surface bound receptor-specific ligand as the cell surface capture molecule, c) antibody-producing cells by using an antibody-binding protein as the cell surface capture molecule, d) sTCR's by using an s-TCR-binding protein (e.g., and antigen recognized by the TCR) as the cell surface capture molecule, e) TCR-Fc's, by using an Fc-binding protein as a cell surface capture molecule, or f) bispecific antibodies that harbor a mutation in one of its CH3 domains that abrogates protein A binding, by using a fusion protein capture molecule that comprises an ScFv domain fused to an FcγR transmembrane and cytoplasmic domain.

In accordance with the methodology of this invention, a cell is first transfected with a vector containing a nucleotide sequence that encodes a cell surface capture molecule that is capable of binding the secreted POI, under conditions in which such cell surface capture molecule is expressed. Transfected cells which are appropriate producers of such cell surface capture molecules are then detected and isolated, and such cells are cultured. These cells may either naturally produce the POI, or the POI may be recombinantly produced. If the cells naturally produce the POI, they are ready for detection and isolation. If the POI is to be recombinantly produced, then the isolated and cultured cells expressing the specified cell surface capture molecule are transfected with second nucleotide sequence that encodes the secreted POI, under conditions in which the secreted POI is expressed. Upon expression, the secreted POI binds to the cell surface capture molecules and the cells displaying bound POI are detected and isolated.

If the POI is naturally produced by the cell, the cell will not be transfected with nucleotide sequence encoding the POI. Therefore, this aspect of the invention is applicable to any and all cells producing a POI. In addition, if the cell surface capture molecule is naturally produced by the cell, the cell need not be transfected with nucleotide sequences encoding the cell surface capture molecule. Therefore, this aspect of the invention is applicable to any and all cells producing a cell surface capture molecule.

A wide variety of host cells may be transfected. These cells may be either of eukaryotic or of prokaryotic origin. The cells will often be immortalized eukaryotic cells, and in particular, mammalian cells, for example monkey kidney cells (COS), Chinese hamster ovary cells (CHO), HeLa cells, baby hamster kidney cells (BHK), human embryonic kidney cells (HEK293), leukocytes, myelomas, cell lines transfected with adenovirus genes, for example, AD5 E1, including but not limited to immortalized human retinal cells transfected with an adenovirus gene, for example, PER.C6™ cells, and embryonic stem cells. The cells may also be non-mammalian cells including bacterial, fungi, yeast and insect cells, including, but not limited to, for example *Escherichia coli, Bacillus subtilus, Aspergillus* species, *Saccharomyces cerevisiae*, and *Pichia pastoris*. All cells may be grown in culture trays medium under appropriate conditions or in a synergistic host. The most desirable cells will be mammalian cells capable of culture.

The secreted POI bound to the cell surface capture molecule may be detected and isolated by various techniques known in the art. Cultures cells displaying the secreted POI may be contacted with (a) molecule(s) capable of directly or indirectly binding the secreted POI wherein such detection molecule(s) may contain a detection label, such as, for example, a chromogenic, fluorogenic, colored, fluorescent, or magnetic label. The label bound to the detection molecule may be detected and the cell isolated using various methods. Most preferably, within a cell population the label will be detected and the cell isolated utilizing flow cytometry. Alternatively, the detection molecule may be used for the direct isolation of cells displaying the POI. This may be accomplished by conjugation of the detection molecule to a culture plate, paramagnetic molecules, or any other particle or solid support. In addition, displayed POI may be detected directly by a property of the detection molecule or the POI.

In one embodiment, two detection molecules that bind each other and are differentially labeled are used to detect a displayed secreted POI that blocks that interaction. If a cell displays a secreted POI that binds the first detection molecule and blocks the interaction between the first and second detection molecule, that cell may be isolated based on the presence of only the first detection molecule on its surface. On the other hand, if a cell displays a secreted POI that binds the first detection molecule but does not block the interaction between the first and second detection molecule, that cell may be isolated based on the presence of both detection molecules on its surface. For example, antibody producing cells expressing antibodies that specifically block, or do not block, the formation of a receptor-ligand complex may be identified. If the detection molecules are a receptor and its ligand which are differentially labeled, then an antibody producing cell that expresses antibodies that block the receptor-ligand complex from forming may be detected by the presence of one label on its surface, whereas an antibody producing cell that expresses antibodies that do not block the receptor-ligand complex from forming may be detected by the presence of both labels on its surface.

In any of the embodiments and with regards to isolating expressing cells from non-expressing cells or lesser expressing cells, one of the principal difficulties, when the POI is a secreted protein, is diffusion of POI between neighboring cells. Therefore, it is critical that any system that is designed to capture the secreted POI on the cell surface must prevent the diffusion of the POI from the expressing cell to a neighboring cell and its adherence to that cell. If diffusion is allowed to occur, and neighboring cells become decorated with the secreted POI, then separation of cells based upon the degree of POI decoration will fail to discriminate high expressing cells from cells with low expression levels, and may fail to effectively isolate expressing from non-expressing cells.

Therefore one embodiment of this invention is to block the diffusion of the secreted POI between neighboring cells. This may be accomplished by the addition of a blocking molecule that binds either the cell surface capture molecule or the POI and prevents the binding of the secreted POI to the cell surface capture molecule. In this aspect, the detection molecules do not bind the blocking molecule. For example, if the cell surface receptor is the hFcγRI and the secreted POI possesses the human IgG Fc fragment, then diffusion of the secreted POI between neighboring cells may be blocked by the addition of exogenous rat IgG to the culture media. Detection of cells displaying secreted POI, and not bound rat IgG, is achieved by use of antibodies specific for human IgG Fc that do not recognize rat IgG. In another embodiment, binding of the secreted POI between neighboring cells is reduced by increasing the viscosity of the media.

In one embodiment of this invention, the secreted POI is not allowed to accumulate in the media. This may be accomplished by regulating the expression of the secreted POI and/or the cell surface capture molecule such that brief expression of the POI results in sufficient POI to bind the cell surface capture molecule but insufficient amounts for diffusion. In another embodiment, cells may be removed from the media containing accumulated POI, the POI bound to the cells is stripped off, and POI expression is allowed to continue for a limited period of time such that secreted POI does not accumulate in the media. Proteins may be stripped by methods known in the art, for example, washing cells with low pH buffer.

According to this invention, those cells in a cell population that bind the most detection molecules also express the most secreted POI. In fact, the more POI that an individual cell secretes, the more POI is displayed on the cell surface. This correlation between the amount of surface-displayed POI and the expression level of the POI in that cell allows one to rapidly identify cells with a desired relative expression level from a population of cells.

In one embodiment, a DNA library may be used to express secreted protein which may be displayed on the cell surface by the cell surface capture molecule. For example, a library of DNA may also be generated from the coding regions of the antibody variable domains from B-cells isolated from immunized animals. The DNA library may then be expressed in a cell that expresses a cell surface capture molecule specific for antibodies such that clones of desired specificity, isotype, or avidity may be identified and isolated by the method of the invention. In another embodiment, a library of DNA may be generated from the coding regions of T cell receptor variable domains from T-cells, and fused to, for example, an Fc capable of binding to an Fc-binding protein. The DNA library may them be expressed in a cell that expresses an Fc-binding protein such that clones of desired specificity, isotype, or avidity may be identified and isolated as described herein.

In another embodiment, transgenic mammals may be created that express a particular cell surface capture molecule in one or more cell types. The cells from such transgenic mammals may then be screened directly for the production of a POI. For example, it may be desirable to express a cell surface capture molecule, specific for antibodies, in plasma cells. Accordingly, plasma cells from immunized mice may be harvested and those cells producing antibodies specific to the desired antigen may be isolated by the method of the invention.

In a further embodiment of the invention, antibody production is measured through the use of a CHO cell line that expresses the human FcγR1 receptor (FcγRI) which binds the particular antibody or TCR-Fc that is the POI.

In another aspect of the invention, the protein of interest comprises one or more T cell receptor variable domains or a soluble T cell receptor. The one or more T cell receptor variable domains can be covalently linked to a moiety that can bind a cell surface capture protein. In a specific embodiment, the one or more T cell receptor variable domains are fused to an Fc sequence, e.g., a human Fc sequence, and the cell surface capture protein is an Fc receptor, e.g., an FcγR.

The general structures of TCR variable domains are known (see, e.g., Lefranc and Lefranc (2001) The T Cell Receptor FactsBook, Academic Press, incorporated herein by reference; see, e.g., pp. 17-20; see also, Lefranc et al. (2003) IMGT unique numbering for immunoglobulin and T cell receptor variable domains and Ig superfamily V-like domains, Developmental and Comparative Immunology 27:55-77, and Lefranc et al. (2005) IMGT unique numbering for immunoglobulin and T cell receptor constant domains and Ig superfamily C-like domains, Developmental and Comparative Immunology 29:185-203, each incorporated herein by reference). In one embodiment, a TCR variable domain of a TCR-Fc comprises an N-terminal region having a variable domain of 104-125 amino acids. In another embodiment, the TCR-Fc further comprises a TCR constant region comprising 91-129 amino acids. In another embodiment, the TCR-Fc further comprises a connecting peptide comprising 21-62 amino acids.

In one embodiment, the Fc sequence is fused directly or through a linker to the TCR variable domain. In another embodiment, the TCR-Fc comprises a TCR variable region and a TCR constant region, and the Fc sequence is fused directly or through a linker to the TCR constant region. In another embodiment, the TCR-Fc comprises a TCR variable region, a TCR constant region, and a connecting peptide, and the Fc sequence is fused directly or through a linker to the connecting peptide.

The sTCR, TCR-Fc, or fusion protein comprising one or more T cell receptor variable regions can be selected so as to specifically bind an antigen of interest, for example, a substance produced by a tumor cell, for example, tumor cell substance that is capable of producing an immune response in a host. In a specific embodiment, the antigen is an antigen that is present on the surface of a tumor cell (i.e., a tumor antigen), is recognized by a T cell, and that produces an immune response in a host. Tumor antigens include, for example, alphafetoprotein (AFP), carcinoembryonic antigen (CEA), MUC-1, epithelial tumor antigen (ETA), tyrosinase (e.g., for malignant melanoma), melanoma-associated antigen (MAGE), and mutated or abnormal forms of other proteins such as, for example, ras, p53, etc.

In one embodiment, the POI is a TCR-Fc, and the TCR-Fc comprises a TCR α chain variable region fused to an Fc sequence and a TCR β chain fused to the Fc sequence (each directly or through a linker), wherein the TCR α chain-Fc fusion and the TCR β chain-Fc fusion associate to form an αβ TCR-Fc. In a specific embodiment, the αβ TCR-Fc comprises the following two polypeptides: (1) a TCR α chain variable region fused to a TCR α chain constant region fused to an Fc sequence, and (2) a TCR β chain variable region fused to a TCR β chain constant region fused to an Fc sequence.

In another embodiment, the POI is a TCR-Fc having a TCR α variable region and a TCR β variable region and, optionally, a TCR α constant region and/or a TCR β constant region. In a specific embodiment, the TCR-Fc is encoded by a nucleic acid comprising (5' to 3') a TCR α variable region sequence, optionally followed by a TCR α constant region sequence, a TCR β variable region sequence, optionally followed by a TCR β constant region sequence, optionally a linker, then an Fc sequence. In a specific embodiment, the TCR-Fc is encoded by a nucleic acid comprising (5' to 3') a TCR β variable region sequence, optionally followed by a TCR β constant region sequence, a TCR α variable region sequence, optionally followed by a TCR α constant region sequence, optionally a linker, then an Fc sequence. In various embodiments, constructs encoding TCR-Fc's are preceded by signal sequences, e.g., secretion signal sequences, to render them secretable.

In another embodiment, the POI is a TCR-Fc, and the TCR-Fc comprises a TCR-Fc comprising a TCR γ chain fused to an Fc sequence and a TCR δ chain variable region fused to an Fc sequence to form a γδ TCR-Fc. In a specific embodiment, the γδ TCR-Fc comprises the following two polypeptides: a TCR γ chain variable region fused to a TCR γ chain constant region fused to an Fc sequence, and (2) a TCR δ chain variable region fused to a TCR δ chain constant region fused to an Fc sequence.

T cell receptor variable regions can be identified and/or cloned by any method known in the art. The T cell receptor variable regions of the protein of interest are obtainable, for example, by expressing rearranged T cell receptor variable region DNA in a cell, for example, fused to a human Fc sequence. Rearranged T cell receptor variable regions specific for a particular antigen can be obtained by any suitable method known in the art (see references below), for example, by exposing a mouse to an antigen and isolating T cells of the mouse, making hybridomas of the T cells of the mouse, and screening the hybridomas with the antigen of interest to obtain a hybridoma of interest. Rearranged T cell variable regions specific for the antigen of interest can be cloned from the hybridoma(s) of interest. T cell receptor variable regions specific for an antigen can also be identified using phage display technology, for example, as provided in references below. The variable regions can then be cloned and fused, for example, to a human Fc to make a protein of interest that can bind to a cell surface capture molecule that is an FcγR.

Methods for identifying and/or cloning T cell receptor variable regions are described, for example, in U.S. Pat. No. 5,635,354 (primers and cloning methods); Genevée et al. (1992) An experimentally validated panel of subfamily-specific oligonucleotide primers (Vα1-w29/Vβ1-w24) for the study of human T cell receptor variable V gene segment usage by polymerase chain reaction, Eur. J. Immunol. 22:1261-1269 (primers and cloning methods); Gorski et al. (1994) Circulating T Cell Repertoire Complexity in Normal Individuals and Bone Marrow Recipients Analyzed by CDR3 Size Spectratyping, J. Immunol. 152:5109-5119 (primers and cloning methods); Johnston, S. et al. (1995) A novel method for sequencing members of multi-gene families, Nucleic Acids Res. 23/15:3074-3075 (primers and cloning methods); Pannetier et al. (1995) T-cell repertoire diversity and clonal expansions in normal and clinical samples, Immunology Today 16/4:176-181 (cloning methods); Hinz, T. and Kabelitz, D. (2000) Identification of the T-cell receptor alpha variable (TRAV) gene(s) in T-cell malignancies, J. Immunol. Methods 246:145-148 (cloning methods); van Dongen et al. (2002) Design and standardization of PCR primers and protocols for detection of clonal immunoglobulin and T-cell receptor gene recombinations in suspect lymphoproliferations: U.S. Pat. No. 6,623,957 (cloning methods and primers); Report of the BIOMED-2 Concerted Action BMH4-CT98-3936, Leukemia 17:2257-2317 (primers and cloning methods); Hodges et al. (2002) Diagnostic role of tests for T cell receptor (TCR) genes, J. Clin. Pathol. 56:1-11 (cloning methods); Moysey, R. et al. (2004) Amplification and one-step expression cloning of human T cell receptor genes, Anal. Biochem. 326:284-286 (cloning methods); Fernandes et al. (2005) Simplified Fluorescent Multiplex PCR Method for Evaluation of the T-Cell Receptor Vβ-Chain Repertoire, Clin. Diag. Lab. Immunol. 12/4:477-483 (primers and cloning methods); Li, Y. et al. (2005) Directed evolution of human T-cell receptors with picomolar affinities by phage display, Nature Biotech. 23/3: 349-354 (primers and cloning methods); Wlodarski et al. (2005) Pathologic clonal cytotoxic T-cell responses: non-random nature of the T-cell receptor restriction in large granular lymphocyte leukemia, Blood 106/8:2769-2780 (cloning methods); Wlodarski et al. (2006) Molecular strategies for detection and quantitation of clonal cytotoxic T-cell responses in aplastic anemia and myelodysplastic syndrome, Blood 108/8:2632-2641 (primers and cloning methods); Boria et al. (2008) Primer sets for cloning the human repertoire of T cell Receptor Variable regions, BMC Immunology 9:50 (primers and cloning methods); Richman, S. and Kranz, D. (2007) Display, engineering, and applications of antigen-specific T cell receptors, Biomolecular Engineering 24:361-373 (cloning methods). Examples of sTCRs are provided in, for example, U.S. Pat. Nos. 6,080,840 and 7,329,731; and, Laugel, B et al. (2005) Design of Soluble Recombinant T Cell Receptors for Antigen Targeting and T Cell Inhibition, J. Biol. Chem. 280:1882-1892; incorporated herein by reference. Fc sequences are disclosed herein; examples of Fc sequences, and their use in fusion proteins, are provided, for example, in U.S. Pat. No. 6,927,044 to Stahl et al. All of the foregoing references are incorporated herein by reference.

In a further embodiment of the invention, the cell surface capture molecule is designed to engage and display those proteins of interest that are normally incapable of binding with sufficient affinity or bind with low affinity to an FcγR capture molecule. Those proteins of interest include IgG4 and IgG2 molecules. Thus, a modular capture molecule was designed and built based upon an ScFv domain fused to an FcγR transmembrane and cytoplasmic domain. The ScFv domain was derived from a high affinity anti-humanFc antibody, and contains a heavy chain variable domain fused to a light chain variable domain. The FcγR-TM-cytoplasmic domain was used to enable the proper insertion and orientation in the plasma membrane. The ScFv-FcγR-TM-cyto fusion protein is capable of binding IgG4 and other Fc containing molecules, as well as IgG2 and IgG1 subtypes, and those heterodimeric (e.g., bispecific antibodies) comprising at least one wild type CH3 domain, wherein the other CH3 domain may contain an Fc*-type substitution.

In a further embodiment of the invention, the cell surface capture molecule is designed to engage and display those proteins of interest that contain a modified CH3 domain, such as the Fc* polypeptide, which comprises H95R and Y96F amino acid substitutions (the numbering is based upon the IMGT system), e.g., SEQ ID NO: 42. Those proteins of interest include bispecific antibodies, such as antibody heterotetramers that are useful in the manufacture of bispecific antibodies are generally described in US Patent Application Publication No. US 2010/0331527 A1, Dec. 30, 2010, which is incorporated in its entirety herein by reference. Thus, a modular capture molecule was designed and built based upon an ScFv* domain fused to an FcγR transmembrane and cytoplasmic domain. The ScFv* domain was derived from a high affinity anti-Fc* antibody, and contains heavy chain variable domain fused to a light chain variable domain. The FcγR-TM-cytoplasmic domain was used to enable the proper insertion and orientation in the plasma membrane. The ScFv*-FcγR-TM-cyto fusion protein binds any Fc*-containing molecule, such as wildtype IgG3, and heterodimers of IgG4, IgG2, and IgG1, which contain at least one Fc* polypeptide sequence.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of pTE084. pTE084 was constructed by ligating the 1,436 bp Xba I fragment from pCAE100 that encodes the human FcγRI (hFcγRI; GenBank accession number M21091) into the Xba I site of pRG821. The orientation of hFcγRI in desirable plasmids resulting from the ligation was examined by restriction mapping with Not I, Pst I, Eco RI, and Stu I. pTE084 was designed for the high level expression of hFcγRI, the high affinity cell surface receptor for the Fc domain of human IgG. It contains two independent expression cassettes. One cassette is a hFcγRI gene driven by the CMV-MIE promoter, and the second cassette is the neomycin phosphotransferase II (npt) gene, which confers resistance to G418, driven by the SV40 late promoter.

Construction of a CHO K1 derivative that expresses hFcγRI. CHO K1 cells ($4\times10^6$) were transfected with pTE084 using Lipofectamine™ (Life Technologies; Rockville, Md.) following manufacturer's suggestions. The cells were placed in the culture medium (10% fetal bovine serum, 90% Ham's F-12, 2 mM L-glutamine; all reagents were from Life Technologies, Rockville, Md.) containing 500 µg/ml G418 (Life Technologies) for 15 days. The cells that survived G418 selection were trypsinized, pooled, and stained with FITC-conjugated human IgG, Fc fragment (FITC-hFc; Jackson ImmunoResearch Laboratories, West Grove, Pa.). Briefly, the cells grown on 10 cm culture plates were washed once with Dulbecco's phosphate-buffered saline (PBS) without calcium chloride and magnesium chloride (Life Technologies). Three milliliters of 0.25% trypsin (Life Technologies) were added to each plate. The plates were swirled until the cells detached from the plate. Ten milliliters of culture medium was immediately added to each plate of the detached cells. The cells were then collected by centrifugation at 1,000×g for 4 minutes. After removal of supernatant, the cells were resuspended in 4 ml of 2 µg/ml FITC-hFc diluted in culture medium. The cells were then placed on a platform shaker and stained for one hour at room temperature. To remove unbound FITC-hFc, the cells were washed twice with 20 ml PBS. The degree of FITC-hFc label on the cells was measured by flow cytometry on a MOFLO™ cell sorter (Cytomation; Fort Collins, Colo.). The FITC-hFc did not stain mock-transfected parental CHO K1 cells but gave rise to a distribution of fluorescence in the G418-resistant, pTE084-transfected pool. The top 1% most fluorescent cells from the selected pool were placed into 96-well plates at 1 cell/well by flow cytometry. Nine days later, 88 cell clones in the 96-well plates were expanded into 24-well plates. After 3 days, the cells in individual wells were washed once with 1 ml PBS, stained with 0.5 ml of 2 µg/ml FITC-hFc for 1 hour, washed twice with 1 ml PBS and examined for cell surface staining under a fluorescent microscope. The thirty three most fluorescent clones were chosen, expanded, then screened by flow cytometry.

Diffusion of secreted protein between expressing cells and non-expressing cells among cells was blocked by adding IgG: As all cells in a hFcγRI clonal cell line express a cell surface hFcγRI, they all possess the ability to bind IgG or fusion proteins consisting of the Fc domain of IgG. Because hFcγRI binds IgG from a variety of species (van de Winkel and Anderson, 1991), a panel of animal IgGs was tested for the ability to block the binding of a protein containing a human IgG1 (hIgG1) Fc tag (4SC622) to hFcγRI-expressing cells. 4SC622 is a chimeric molecule consisting of IL-2Rγ extracellular domain fused to the hIL-4Rγ extracellular domain which is then fused to the hIgG1-Fc domain. In this experiment, cultures of RGC1, an hFcγRI-expressing cell line selected from CHO K1 cells that have been stably transfected with pTE084, were incubated with 1 µg/ml 4SC622 for 18 hours in the presence or absence of 1 mg/ml IgG from different species in a 37° C. tissue culture incubator.

Cell surface binding of 4SC622 was determined by flow cytometry after washed cells were stained with phycoerythrin-conjugated mouse IgG1 monoclonal AG184 (PE-AG184) specific for the hIL-2Rγ component of 4SC622 (BD Pharmingen; San Diego, Calif.), following procedures outlined for cell staining with FITC-hFc.

It was found that hIgG completely blocked 4SC622 from binding to the hFcγRI expressed on the surface of RGC1. Rat, rabbit and canine-derived IgG also effectively blocked binding whereas bovine and ovine-derived IgG did not block. The ability of exogenously added rat IgG to block the binding of an exogenously added hIgG1 Fc-tagged protein (4SC622) to cell surface hFcγRI suggests that rat IgG can also block transfer between cells expressing a hIgG1 Fc-tagged protein at different levels. To test this, two cell lines that can be distinguished by the presence or absence of the green fluorescent protein (EGFP) were generated from RGC1. Briefly, to mark RGC1 cells with EGFP, $2 \times 10^6$ RGC1 cells were co-transfected with 0.5 mg PTE073 which encodes a hygromycin B phosphotransferase gene driven by phosphoglycerate kinase promoter, and 5 mg pRG816-EGFP which encodes EGFP gene driven by CMV-MIE promoter. The transfected cells were selected with 200 µg/ml hygromycin B (Sigma; St. Louis, Mo.) for two weeks. Green fluorescent cells were isolated by flow cytometry. One EGFP and hFcγRI-expressing clone, RGC2, was used in cell mixing experiments. The other cell line used in these experiments, RGC4, was generated by stable transfection of RGC1 with plasmid pEE14.1-622. pEE14.1-622 is a plasmid in which expression of 4SC622 is driven by the CMV-MIE promoter and includes a glutamine synthetase minigene, which confers resistance to the analog methionine sulfoximine (MSX), and allows for selection of stable integration events. RGC4 cells express hFcγRI on the cell surface and secrete the hIgG1 Fc-tagged protein 4SC622. One plate of mixed cells comprising 50% RGC2 and 50% RGC4 cells was incubated with 1 mg/ml rat IgG for 18 hours prior to staining with PE-AG184 then examined by flow cytometry. EGFP fluorescence of RGC2 cells shows that RGC2 cells also bind exogenously added 4SC622 (1 µg/ml) as indicated by an increase in PE-AG184 fluorescence. RGC4 did not fluoresce in the EGFP gate. Significantly, exogenously added rat IgG did not reduce the percentage of RGC4 cells that stained positive for cell surface 4SC622, suggesting that the binding of 4SC622 to hFcγRI occurred while the proteins were in transit to the cell surface. When RGC2 and RGC4 cells were mixed, the 4SC622 protein secreted from RGC4 cells accumulated in the medium and bound most of the RGC2 cells. However, the addition of 1 mg/ml rat IgG significantly reduced the percentage of RGC2 cells that bound 4SC622, demonstrating that rat IgG blocked the transfer of secreted hIgG1 Fc-tagged protein from expressing cells to non-expressing cells.

Example 2

Cell Surface Fluorescence Correlates with the Expression Level of 4SC622

RGC1 cells ($4 \times 10^6$) were transfected with pEE14.1-622 and a pool of stable transfectants was obtained after selection for 2 weeks in medium comprised of 10% dialyzed fetal bovine serum, 90% glutamine-free Dulbecco's Modified Eagle's Medium (DMEM), 1×GS supplement, and 25 µM MSX (All reagents were from JRH Biosciences, Lenexa, Kans.). Rat IgG was added to the culture medium to 1 mg/ml 18 hours prior to immunostaining. The cells were trypsinized, washed with PBS, and stained with 1.5 µg/ml of a polyclonal FITC-conjugated anti-human IgG (H+L) F(ab')$_2$ fragment (Jackson ImmunoResearch Laboratories) for one hour at room temperature following procedures as described for FITC-hFc staining in Example 1. Cell staining was then analyzed by flow cytometry. The distribution of fluorescence suggested that the selected pool contained cells with a wide range of 4SC622 expression levels. Cells in the top 3% (R3 bracket), 7-11% (R5 bracket), and 15-19% (R7 bracket) with respect to their immunofluorescence were sorted into three distinct pools and expanded for 9 days. Average 4SC622 production per cell for the pools was determined by measuring cell numbers and 4SC622 levels in the media after 3 days growth by an immuno-based Pandex assay (Idexx; Westbrook, Me.) following the manufacturer's recommendations. In the Pandex assay, fluoricon polystyrene assay particles coated with goat anti-human IgG, g-chain specific antibody (Sigma) were used to capture 4SC622 from the medium, and a FITC-conjugated goat anti-human IgG, Fc specific (Sigma) was used to detect bead-bound 4SC622. Known amounts of purified 4SC622 were included in the assay for calibration. Cells in the top 3%, 7-11%, and 15-19% pool were found to produce 4SC622 at 1.42, 0.36, and 0.22 pg/cell/day, respectively. Thus, there was a correlation between cell surface 4SC622 staining and specific protein production. This result suggests that individual cells that express 4SC622 at high levels may be obtained by isolating cells that were stained brightest by the polyclonal FITC-conjugated anti-human IgG (H+L) F(ab')$_2$ fragment.

Example 3

Isolation of Expression Clones in RGC1: IL-4 Trap

To directly demonstrate the efficiency in generating clonal cell lines with high level secreted protein production by our methodology, clonal 4SC622 producing cell lines were generated from RGC1. RGC1 cells (4×10$^6$) were transfected with pEE14.1-622, and selected for two weeks with 25 μM MSX to obtain a pool of stable transfectants. MSX-resistant cells were pooled and incubated with 1 mg/ml human IgG for 18 hours, prior to staining with PE-AG184. Six cells from the top 5% gate, as determined by flow cytometry analysis of cell surface 4SC622 staining, were isolated and expanded. 4SC622 production from the six clonal lines was determined and compared to 4SC622 production from clones obtained by hand-picking selected colonies followed by dilution cloning and amplification. One RGC1-derived clone, RGC4, produced 4SC622 at 12 pg/cell/day. This level is similar to that of the best 4SC622 producer isolated by hand-picking and analyzing 2,700 clones. Thus, compared with hand-picking colonies, the methodology outlined in this invention proves to be far more efficient in the screening and cloning of high producers.

VEGF Trap. Plasmids pTE080 and pTE081 encode the genes for VEGF Traps, hVEGF-R1R2 and hVEGF-R1R3. hVEGF-R1R2 is a chimeric molecule consisting of the first Ig domain of hVEGFR1 fused to the second Ig domain of hVEGFR2 which is then fused to the hIg1 FC domain. hVEGF-R1R3 is a chimeric molecule consisting of the first Ig domain of hVEGFR1 fused to the second Ig domain of hVEGFR3 which is then fused to the hIgG1-Fc domain. In these plasmids, the gene for the VEGF Trap is driven by the CMV-MIE promoter and a glutamine synthetase minigene, which confers resistance to MSX, is expressed for selection of stable integration events. RGC1 cells were transfected with either of these plasmids and grown in medium containing 25 μM MSX for 2 weeks to select for cells in which the plasmid has stably integrated. MSX-resistant cells were incubated with 0.1 μg/ml IgG2a and mouse IgG3 for 18 hours prior to staining with 1.5 μg/ml polyclonal FITC-conjugated anti-human IgG (H+L) F(ab')$_2$ fragment. Cell were stained for 1 hour then washed twice with PBS prior to flow cytometry. Single cells were sorted into 96-well tissue culture plates from the pool of cells whose fluorescence was among the highest 1%. The cells in individual wells were expanded and their productivities were determined by Pandex assays. RGC-derived clones expressing both hVEGF-R1R2 and hVEGF-R1R3 had higher specific productivities and were isolated by screening fewer clones as compared to the highest-expressing hand-picked MSX-resistant colonies. See Table 1.

TABLE I

SPECIFIC PRODUCTIVITY COMPARISON

| Protein | Transient (μg/ml) | Hand-picked CHO K1 Stable Cell Lines | | RGC1-derived Stable Cell Lines | |
|---|---|---|---|---|---|
| | | Sp. Prod. (pg/cell/day) | # clones screened | Sp. Prod. (pg/cell/day) | # clones screened |
| 4SC622 | 1.1 | 12 | 2700 | 12 | 6 |
| hVEGF-R1R2 | 33 | 68 | 190 | 77 | 62 |
| hVEGF-R1R3 | 27 | 5 | 100 | 22.6 | 42 |

Example 4

Cell Surface-bound hIgG1 Fc-Tagged Protein is Internalized by RGC1 hFcγRI is known to induce internalization of its cell surface-bound ligand. To analyze whether RGC1 cells could internalize cell surface-bound 4SC622, 1 μg/ml 4SC622 was added to RGC1 cells for 1 hour and then the cells were immediately processed for 4SC622 immunostaining with PE-AG184 and flow cytometry analysis. Ninety-three percent of the cells stained positive for cell surface 4SC622. Alternatively, 1 μg/ml 4SC622 was added to RGC1 cells for 1 hour, then the cells were washed and incubated in culture medium without 4SC622 with PE-AG184 for 18 hours. Flow cytometry analysis following immunostaining for 4SC622 showed that 9% of the cells retained 4SC622 on the cell surface. To further characterize the loss of surface-bound 4SC622, purified 4SC622 protein was added to the media of RGC1 and parental CHO K1 cells, then levels of 4SC622 in the media were measured over time. 4SC622, added to 2 μg/ml to the culture media in a 10 cm plate, was significantly lower in RGC1 conditioned medium after 3 days incubation as compared to the CHO K1 control. These results show that the concentration of 4SC622 in the culture medium is reduced by the presence of hFcγRI on the cell surface. The results suggest that the depletion of 4SC622 from the media was the result of hFcγRI-4SC622 complex internalization. This internalization of receptor-ligand complexes may facilitate the effective removal of all 4SC622 from non-expressing cells in the presence of blocking IgG during the 18-hour blocking step.

Example 5

Construction of CHO K1 Cell Lines with Inducible hFcγRI Expression

Flow cytometry-based autologous secretion trap (FASTR™) methods that utilize the hFcγRI allow rapid isolation of high expression clones. However, if hFcγRI mediates turnover of Fc-tagged proteins, then the realized production of the secreted protein by engineered hFcγRI expressing cells would be higher if hFcγRI expression could be inhibited during the production period. To this end, a CHO K1 cell line in which the expression of hFcγRI is induced by tetracycline, or the analog doxycycline, was constructed. In this system, CHO K1 cells were first engineered to express the tetracycline repressor protein (TetR) and hFcγRI was placed under transcriptional control of a promoter whose activity was regulated by TetR. Two tandem TetR operators (TetO) were placed immediately downstream of the CMV-MIE promoter/enhancer in pTE084 to generate pTE158. Transcription of hFcγRI from the CMV-MIE promoter in pTE158 was blocked by TetR in the absence of tetracycline or some other suitable inducer. In the presence of inducer, TetR protein was incapable of binding TetO and transcription of hFcγRI occurred.

CHO K1 cells were transfected with pcDNA6/TR, a plasmid that confers resistance to blasticidin in which expression of TetR originates from the CMV-MIE promoter (Invitrogen; Carlsbad, Calif.). After two weeks of selection with 2.5 μg/ml blasticidin (Invitrogen), the stable transfectants were pooled. This pool was then transfected with pTE158, a plasmid that confers resistance to G418 in which the expression of hFcγRI is dependent on a CMV-MIE/TetO hybrid promoter. The cells consecutively transfected with pcDNA6/TR and pTE158 were selected with 400 μg/ml G418 and 2.5 μg/ml blasticidin for 12 days then pooled. The pool was induced for two days by the addition of 1 μg/ml doxycycline then stained with FITC-hFc to identify cells that express hFcγRI. The top 5% of cells expressing hFcγRI were collected as a pool, expanded for 6 days in the absence of doxycycline, and were again stained with FITC-hFc for the presence of hFcγRI. Cells that did not stain for hFcγRI were collected and expanded in culture medium containing 1 μg/ml of doxycycline for three days. The pool was then stained for the presence of hFcγRI and were isolated by flow cytometry. Cells that expressed the highest levels of hFcγRI (top 1%) were sorted onto 96 well plates at one cell per well. These cells presumably contained cell that had low non-induced expression levels of FcγR1 and high inducible levels of FcγR1. After expansion, the induction of hFcγRI by doxycycline in 20 clones was confirmed by immunostaining with FITC-hFc and flow cytometry. One clone was chosen for further characterization and was named RGC10.

In the absence of doxycycline, RGC10 did not express detectable levels of hFcγRI, whereas high levels of hFcγRI were observed in cells that were induced with 1 μg/ml of doxycycline for three days. The mean fluorescence of RGC10 cells increased by more than 1,000 fold after induction by doxycycline.

Example 6

Isolation of 4SC622-producing Cell Lines from RGC10

RGC10 cells were transfected with pEE14.1-622, and MSX-resistant cells were pooled after selection with 25 mM MSX for two weeks. Expression of hFcγRI was induced by the addition of 1 μg/ml of doxycycline to the culture medium for three days. One mg/ml rat IgG was added to the culture medium containing doxycycline 18 hours prior to staining with polyclonal FITC-conjugated anti-human IgG (H+L) F(ab')$_2$ fragment and analysis by flow cytometry. Cells that expressed the highest levels of 4SC622 (top 1%) were sorted into 96 well plates at 1 cell per well. Without induction of hFcγRI expression by doxycycline, staining with polyclonal FITC-conjugated anti-human IgG (H+L) F(ab')$_2$ fragment fails to detect cell surface bound 4SC622. Sixty clones were expanded in the absence of doxycycline. The specific productivity of the 13 highest producers was determined by Pandex assay. The specific productivity of clone 1C2 was 17.8 pg/cell/day, significantly better than the 12 pg/cell/day observed for the best 4SC622 cell line previously isolated using the unregulated hFcγRI cell line RGC1.

Example 7

Sp2/0 Myeloma Cells can be Engineered to Express a Cell Surface Capture Protein

In this example, the Sp2/0-Ag14 myeloma cell line was engineered to stably express hFcγRI to demonstrate that the autologous secretion trap method was applicable to cell lines other than CHO. The gene for hFcγRI was introduced into the myeloma cell by retroviral infection. The plasmid pLXRN (Clontech; Palo Alto, Calif.), a retroviral DNA vector wherein a gene of interest may be expressed from the upstream Moloney murine sarcoma virus long terminal repeat (MoMuSV LTR) promoter, was used to generate retrovirus encoding the hFcγRI gene. The 1,363 bp Xho I fragment from pTE084, encoding the human FcγRI gene, was cloned into the Xho I site of pLXRN. A plasmid in which hFcγRI cDNA expression was dependent on the MoMuSV LTR was chosen and named pTE255.

Pantropic retrovirus for the expression of hFcγRI was generated essentially following the manufacturer's guidelines. The packaging cell line GP-293, a HEK 293-based cell line that stably expresses the viral gag and pol proteins (Clontech; Palo Alto, Calif.), was co-transfected with 10 mg each of pVSV-G and pTE255. The plasmid pVSV-G allows expression of the viral envelope protein VSV-G that confers broad host range upon the infective particles.

Construction of Sp2-hFcγRI-4. The pantropic hFcγRI retrovirus was used to infect 1×10$^7$ Sp2/0-Ag14 myeloma cells (American Type Culture Collection; Manassas, Va.) at a multiplicity of about 10 infective particles per cell. Three days after infection, cells were stained for 1 hour then washed twice with PBS prior to analysis by flow cytometry. Those cells expressing hFcγRI, as indicated by bound FITC-hFc, were collected as a pool by flow cytometry. The pool was expanded for 13 days then again stained with FITC-hFc and cells expressing hFcγRI were collected as a pool by flow cytometry. These sorted cells were cultured in 10% fetal bovine serum 90% Dulbecco's Modified Eagle's Medium (DMEM) with 4.5 g/l glucose and 4 mM glutamine for 3 weeks, stained with FITC-hFc, and the cells with mean fluorescence in the top 1% of the population were cloned by single cell sorting. After expansion, 24 clones were examined by flow cytometry for expression of hFcγRI, as described above, and one clone, Sp2-hFcγRI-4, was chosen for additional characterization.

Isolation of Sp2-hFcγRI-4 cells expressing 4SC622 protein. Sp2-hFcγRI-4 cells (1×10$^7$) were transfected with pTE209, a plasmid that allows constitutive expression of 4SC622 from the CMV-MIE promoter and confers resistance to hygromycin. The transfected cells were placed in medium containing 10% FCS, 90% D-MEM and 400 μg/ml hygromycin for 14 days. Hygromycin-resistant cells were incubated with 1 mg/ml rabbit IgG for eighteen hours prior to staining with polyclonal FITC-conjugated anti-human IgG (H+L) F(ab')$_2$ fragment. Cells were stained for 1 hour then washed twice with PBS prior to analysis by flow cytometry. Labeled cells were collected as a pool by flow cytometry then cultured for 5 days and sorted as described above. Cells from the expanded pool that bound the most polyclonal FITC-conjugated anti-human IgG (H+L) F(ab')$_2$ fragment, top 1% population, were then cloned by single cell sorting. Production of 4SC622 from ten clones was analyzed by ELISA and all 10 clones were found to express 4SC622; clone 5H11 produced 4SC622 at 0.5 pg per cell per day. These data showed that clones secreting 4SC622 were efficiently isolated by the autologous secretion trap method from a heterogeneous pool of cells derived from stable transfection of Sp2-hFcγRI-4 cells with pTE209.

To confirm that 4SC622 was autologously displayed on the surface of myeloma cells expressing both 4SC622 and hFcγRI, clone 5H11 was incubated with 1 mg/ml rabbit IgG for 18 hours then stained with FITC-conjugated anti-human IgG (H+L) F(ab')$_2$ fragment and found to display cell surface 4SC622. Secreted protein was displayed under conditions in which cross-feeding was blocked by rabbit IgG, demonstrating the autologous display of 4SC622. These data indicated that the autologous secretion trap method described above was not limited to CHO cells and may be extended to myeloma and other cell types as well.

Example 8

Protein G Chimeric Protein can Function as a Cell Surface Capture Protein

To demonstrate the application of the autologous secretion trap method to a cell surface capture protein other than hFcγRI, a cell line expressing Protein G was constructed. Protein G, from the *Streptococcus* strain G148, binds to all human and mouse IgG subclasses, and as such has utility for the isolation of recombinant cells expressing antibodies or IgG Fc fusion proteins. To demonstrate that the Protein G IgG Fc binding domain could be used as a cell surface capture protein capable of binding to all human and mouse IgG subclasses, we constructed a CHO line expressing a chimeric protein comprised of the Fc binding domain of Protein G fused to the hFcγRI transmembrane and intracellular domain. The Fc binding domain of Protein G contains three homologous repeats of 55 amino acids long (Guss et al., (1986) EMBO 5:1567 and Sjobring et al., (1991) J. Biol. Chem. 266:399) and each repeat is capable of binding one IgG Fc. To improve the expression of this chimeric protein in CHO cells, we constructed a synthetic DNA in which the signal sequence from the mouse ROR1 gene was fused to the Fc binding domain, amino acids 303 to 497 of Protein G (accession # X06173) (SEQ ID NO:1). This synthetic DNA was generated by a combination of oligonucleotide annealing, gap filling, and PCR amplification. The synthetic DNA was then fused, by PCR, to DNA encoding the transmembrane and intracellular domains, amino acids 279 to 374 (SEQ ID NO:2), of hFcγRI (accession M21091). The resultant DNA encoding the Protein G/hFcγRI chimeric protein was cloned into pTE158 downstream of the CMV-MIE promoter, replacing the gene encoding hFcγRI, to yield the plasmid pTE300.

A CHO K1 cell line adapted to grow in serum-free medium, RGC14, was transfected with pTE300, and after three days 400 µg/ml G418 was added to the culture medium to select for stable integration of pTE300. Two weeks after the start of selection, the cells were stained with FITC-hFc to identify cells that expressed hFcγRI. These cells were analyzed by flow cytometry and cells expressing hFcγRI were collected as a pool. The cells were expanded for 10 days and the population of cells expressing hFcγRI was again isolated by flow cytometry. The cells were again expanded, stained with FITC-hFc, and single cells expressing high levels of the Protein G/hFcγRI chimeric protein were isolated by flow cytometry. Single cells that stained positive for FITC-hFc binding were sorted into medium composed of 10% fetal bovine serum, 90% Ham's F12, and 400 µg/ml G418. After two weeks incubation, 48 clones were examined for binding to bovine IgG present in the culture medium by staining with FITC-conjugated antibovine IgG F(ab')$_2$ fragment (Jackson ImmunoResearch Laboratories, West Grove, Pa.). One clone, RGC18 that stained positive with this antibody was chosen for further characterization.

Isolation of expression clones in RGC18: RGC18 cells (6×10$^6$) were transfected with pTE209 and selected for integration of the plasmid by growth in 400 µg/ml hygromycin for 18 days. Hygromycin-resistant cells were incubated with 1 mg/ml rabbit IgG for eighteen hours prior to staining with polyclonal FITC-conjugated anti-human IgG (H+L) F(ab')$_2$ fragment. Cells were stained for 1 hour then washed twice with PBS prior to analysis by flow cytometry. The most fluorescent cells (top 5%) were isolated by single cell sorting and expanded for 3 weeks. Ten clones were examined for 4SC622 secretion. All clones tested secreted 4SC622 at high level, and the best clone, RGC19, had a specific productivity of 6.4 pg/cell day. This result demonstrated that 4SC622-expressing cells were efficiently isolated from a heterogeneous pool of cells derived from stable transfection of RGC18 with pTE209 by the autologous secretion trap method. Furthermore, these data clearly demonstrated that a fragment of Protein G could be engineered to include a signal sequence and transmembrane domain, and function as a cell surface capture protein.

To confirm that 4SC622 was autologously displayed on the surface of RGC19 cells expressing both Protein G/hFcγRI chimeric protein and 4SC622, RGC19 was incubated with 1 mg/ml rabbit IgG for 18 hours then stained with FITC-conjugated anti-human IgG (H+L) F(ab')$_2$ fragment and analyzed by flow cytometry. RGC19 cells were found to possess cell surface 4SC622 under these conditions in which cross-feeding was blocked by rabbit IgG, suggesting autologous display of 4SC622. Rabbit IgG effectively blocked binding of exogenous 4SC622 protein to RGC18 cells, but did not block display of 4SC622 on the cell surface of cells expressing 4SC622. These data demonstrated that the properties of the Protein G/hFcγRI chimeric protein were similar to those of hFcγRI as a cell surface capture protein, and suggested that the autologous secretion trap method can employ other proteins as cell surface capture proteins.

Example 9

Isolation of Antibody-producing Cells from RGC10

To demonstrate the utility of the autologous secretion trap method for the isolation of CHO cell lines that express recombinant antibodies we cloned the DNA encoding variable light and variable heavy genes from the KD5 hybridoma. KD5 is a hybridoma that expresses a monoclonal antibody specific for the human Tie-2 receptor.

The mouse IgG constant region gene sequences were cloned from 500 ng of mouse spleen polyA+ RNA (Clontech, Palo Alto, Calif.). Single stranded cDNA was synthesized using SuperScript First-Strand Synthesis System for RT-PCR, primed with 50 ng of random hexamers (Invitrogen Life Technologies, Carlsbad, Calif.). The mouse kappa light constant DNA sequence (accession # Z37499) was amplified from this cDNA by PCR using the primers 5' mCLK1 (Z37499) (5'-CGGGCTGATG CTGCACCAAC TGTATCCATC TTC-3') (SEQ ID NO:3) and 3' mCLK1 (Z37499) (5'-ACACTCTCCC CTGTTGAAGC TCTT-GACAAT GGG-3') (SEQ ID NO:4). The mouse IgG2a constant region DNA sequence (accession # AJ294738) was also amplified from this cDNA by PCR using the primers 5' mCH2a(AJ294738) (5'-GCCAAAACAA CAGCCCCATC GGTCTATCCA C-3') (SEQ ID NO:5) and 3' mCH2a (AJ294738) (5'-TCATTTACCC GGAGTCCGGG AGAAGCTCTT AGTCG-3') (SEQ ID NO:6). The PCR products were cloned into pCR2.1-TOPO using TOPO TA Cloning kit (Invitrogen Life Technologies, Carlsbad, Calif.) and the sequence of the constant regions were verified.

The KD5 variable region genes were amplified by RT-PCR from KD5 hybridoma mRNA and cloned into pCR2.1-TOPO using the heavy and light chain variable region primer mixes from Amersham-Pharmacia Biotech (Piscataway, N.J.). The variable heavy chain gene was PCR amplified using the pCR2.1-TOPO cloned variable region as template with the primers 5' BspMI/KD5VH N– term (5'-GAGAGTACCT GCGTCATGCA GATGTGAAAC TGCA-GGAGTC TGGCCCT-3') (SEQ ID NO:7) and 3' BspMI/KD5VH C-term (5'-GAGAGACCTG CGTCAGCTGA GGAGACGGTG ACCGTGGT-3') (SEQ ID NO:8), digested with BspMI and ligated to the BsaI-digested IgG2a constant heavy gene PCR fragment amplified with the primers 5' BsaI/CH2a N– term (5'-GAGAGGGTCT CACA-GCCAAA ACAACAGCCC CATCG-3') (SEQ ID NO:9) and 3' BsaI/CH2a C– term (5'-GAGAGGGTCT CCGGC-CGCTC ATTTACCCGG AGTCCGGG AGAA-3') (SEQ ID NO:10). This fragment was then ligated into the BspMI and NotI sites of pRG882. The resulting plasmid, pTE317, was capable of expressing the KD5 recombinant heavy chain gene, fused to the mROR1 signal sequence, from the CMV-MIE promoter. The variable light chain gene was PCR amplified using the pCR2.1-TOPO cloned variable region as template with the primers 5' BsmBI/KD5VL N– term (5'-GAGAGCGTCT CATGCAGACA TCCAGATGAC CCA-GTCTCCA-3') (SEQ ID NO:11) and 3' BsmBI/KD5VL C– term (5'-GAGAGCGTCT CACAGCCCGT TTTATTTCCA GCTTGGTCCC-3') (SEQ ID NO:12), digested with BsmBI and ligated to the BsaI-digested kappa constant light gene PCR fragment amplified with the primers 5' BsaI/CLK N– term (5'-GAGAGGGTCT CAGCTGATGC TGCAC-CAACT GTATCC-3') (SEQ ID NO:13) and 3' BsaI/CLK C– term (5'-GAGAGGGTCT CAGGCCGCTC AACACTCTCC CCTGTTGAAG CTCTTGAC-3') (SEQ ID NO:14). This fragment was then ligated into the BspMI and NotI sites of pRG882. The resulting plasmid, pTE316, was capable of expressing the KD5 recombinant light chain gene, fused to the mROR1 signal sequence, from the CMV-MIE promoter.

The 1450 bp EcoRI-NotI fragment from pTE317, encoding the KD5 heavy chain gene, was cloned into the EcoRI and NotI sites of pRG980, a vector that confers resistance to hygromycin and allows expression of recombinant genes for the UbC promoter, to yield plasmid pTE322. Similarly, the 750 bp EcoRI-NotI fragment from pTE316, encoding the KD5 light chain gene, was cloned into the EcoRI and NotI sites of pRG985, a vector that confers resistance to puromycin and allows expression of recombinant genes for the UbC promoter, to yield plasmid pTE324. RGC10 cells ($5\times10^6$) were transfected with 3 µg pTE322 and 3 µg pTE322 and selected for integration of the plasmids by growth in F12 medium supplemented with 10% fetal calf serum with 20 µg puromycin and 400 µg/ml hygromycin for 14 days. Expression of hFcγRI was induced by the addition of 1 µg/ml of doxycycline to the culture medium for three days. Double-resistant cells were incubated with 1 mg/ml rabbit IgG for eighteen hours prior to staining with goat polyclonal FITC-conjugated anti-mouse IgG (Fcγ) F(ab')$_2$ fragment (Jackson ImmunoResearch Laboratories, West Grove, Pa.). Cells were stained for 1 hour then washed twice with PBS prior to analysis by flow cytometry. The most fluorescent cells (top 5%) were isolated as a pool and expanded for 10 days, after which the protocol was repeated but the top 1% most fluorescent cells were isolated as a pool. This pool was expanded for 10 days then the top 0.1% most fluorescent cells were isolated as single cells into 96-well plates. Clones were analyzed by ELISA for expression of antibody and seven clones were chosen from 53 clones analyzed. The average specific productivity of these clones was 35 pg/cell/day and the best clone expressed the recombinant KD5 monoclonal antibody at 54 pg/cell/day.

Example 10

FASTR™ Screens Unaffected by CSCP Expression Level

To demonstrate that the expression level of the CSCP does not significantly affect the ability to isolate cells expressing an associated sPOI, FASTR™ screens for the same sPOI in two different host cell lines that each express the same CSCP but at either a high level or a low level were compared.

The FASTR™ host cell line RGC10 was selected for high-level expression of hFcγRI protein by stable integration of pTE158 and was found to contain 40 hFcγRI integrated gene copies. A new cell line, RS527, that expressed hFcγRI protein at a lower level, was generated from CHO K1 after stable transfection and selection for single copy gene integration. RS527 cells expressed significantly less hFcγRI protein than RGC10 cells as determined by Western blot analysis of whole cell lysates of the FASTR™ cell lines.

Briefly, RGC10 and RS527 cells were transfected with pTE462, a plasmid capable of expressing a secreted hFc-fusion protein Rc1-hFc and conferring resistance to hygromycin. The transfected cultures were selected with hygromycin for two weeks. The hygromycin-resistant cells were induced with 1 µg/ml doxycycline (Dox) and blocked with rabbit IgG overnight, following the FASTR™ method described herein. The next day, the RGC10/pTE462 and RS527/pTE462 cultures were stained by a FITC-conjugated antibody specific for hFc and then analyzed by flow cytometry. Three cell bins R4, R5, and R6 marking cells with low, medium, and high fluorescence respectively were sorted from each host line and expanded in tissue culture.

To compare Rc1-hFc protein production level from the six cell bins, six cultures were set up using equal number of cells for each bin. Three days later, conditioned media were collected. The Rc1-hFc protein titers in the conditioned media were determined by ELISA and were plotted against mean fluorescence of the respective cell bins. For both RGC10 and RS527 host lines, there was a similar correlation between mean fluorescence (amount of Rc1-hFc displayed on the cell surface) and sPOI protein production levels of the isolated cell pools. Most significantly, the sPOI titers in the two high fluorescence R6 bins derived from RGC10 and RS527 were similar. These data demonstrate that the expression level of the CSCP in a FASTR™ host cell line does not significantly affect the use of that host to isolate transfected cells based on expression level of a sPOI.

Example 11

Tie2 Receptor as a Cell Surface Capture Protein

Cell surface capture proteins (CSCP's) other than FcγRI can be used in the methods described herein. In this example, the Tie2 receptor functions as a CSCP and is used to isolate cells expressing a Tie-specific ScFv$_{C1b}$-Fc fusion protein made from the C1b monoclonal antibody that specifically binds the extracellular domain of Tie2 receptor. Although the CSCP for ScFv$_{C1b}$-Fc can be hFcgRI, this example demonstrates that Tie2 can also be used as the CSCP for ScFv$_{C1b}$-Fc.

To construct an inducible Tie2 CSCP cell line, CHO K1 was first stably transfected with the TetR plasmid pcDNA6/TR. The blasticidin-resistant cell pool was then stably transfected with pTE259, a plasmid that allows inducible expression of a protein comprised of the extracellular domain and transmembrane domain of Tie2. Inducible cell clones were isolated by flow cytometry after staining with an antibody specific for Tie2. The RGC54 clone was chosen to study the feasibility of FASTR™ for the expression of ScFv$_{C1b}$-Fc.

RGC54 cells were stably transfected with pTE988, a plasmid capable of expressing the secreted hFc-fusion protein ScFv$_{C1b}$-Fc and conferring resistance to hygromycin. The transfected culture was selected with hygromycin for two weeks. The hygromycin-resistant cells were induced with Dox and blocked with 1 mg/ml of purified C1b mAb. The C1b monoclonal antibody was the source of the variable regions in ScFv$_{C1b}$-Fc. The next day, the cell pool was stained by a FITC-conjugated antibody specific for hFc and then analyzed by flow cytometry. Three cell bins R6, R7, and R8 marking cells with high, medium, and low fluorescence respectively were sorted and expanded in tissue culture. Three cultures were set up using an equal number of cells for each bin to determine ScFv$_{C1b}$-Fc protein production as determined by ELISA. A correlation existed between mean fluorescence (amount of ScFv$_{C1b}$-Fc binding to Tie2 on the cell surface) and ScFv$_{C1b}$-Fc protein production levels of the isolated cell pools.

These data show that CSCP other than hFcγRI can serve as a CSCP, and also suggest that any receptor may be converted into a CSCP by removal of its cytoplasmic domain. These data also demonstrate that an antigen can be made into a CSCP and used for FASTR™ screening cells expressing an antigen-specific antibody-related molecule.

Example 12

Effective FASTR™ Screens with CSCP:sPOI Pairs Having Low Affinity

Angiopoetin-1 is a ligand for the Tie2 receptor. A chimeric protein comprising angiopoetin-1 receptor binding domain and hFc (FD1-hFc) binds to Tie2 with an affinity constant of 174 nM as determined by BIAcore™. FD1-hFc and Tie2 were chosen as sPOI and CSCP, respectively, to determine if a minimum affinity between CSCP and sPOI is required for FASTR™ screens.

In cell decoration experiments, exogenously added FD1-hFc bound specifically to RGC54 cells through Tie2. To determine if the affinity between Tie2 and FD1-hFc is sufficient to allow FASTR™ screening, RGC54 cells were stably transfected with pTE942, a plasmid capable of expressing the secreted hFc-fusion protein FD1-hFc and conferring resistance to hygromycin. The transfected culture was selected with hygromycin for two weeks. The hygromycin-resistant cells were induced with Dox and blocked with 1 mg/ml of purified FD1-mFc comprising mouse IgG1 Fc. The next day, the cell pool was stained by a FITC-conjugated antibody specific for hFc and then analyzed by flow cytometry. Three cell bins R6, R7, and R8 marking cells with high, medium, and low fluorescence, respectively, were collected. Cultures were set up using equal number of cells for each bin to determine FD1-hFc protein production levels in the conditioned media as determined by ELISA. There was a correlation between mean fluorescence (FD1-Fc binding to cell surface-bound Tie2) and FD1-hFc protein production levels of the isolated cell pools. The bin with the highest fluorescence produced the most FD1-hFc.

These data demonstrate that a CSCP:sPOI pair with low affinity (174 nM KD) can be used for effective FASTR™ screens. Importantly, the dissociation $t_{1/2}$ for FD1-Fc: Tie2 binding is less than 2 minutes, suggesting that any CSCP:sPOI pair with a measurable affinity can work in FASTR™ screens. In addition, this experiment also shows that a non-FcγRI receptor may be used as the CSCP to isolate cells expressing its ligand.

Example 12

Fusing a Transmembrane Domain onto an ScFv Makes a Functional CSCP

An CSCP can be any cell surface-bound protein that has a measurable affinity to the sPOI. To demonstrate this, a totally synthetic CSCP was constructed by fusing the transmembrane domain from the PDGF receptor to an ScFv containing the variable regions from the murine kappa chain-specific monoclonal antibody HB58. A FASTR™ host was constructed that expresses this chimeric protein (ScFv$_{HB58}$-TM$_{PDGFR}$) and was used to isolate cells expressing the angiopoeitin-2 FD domain-specific P12 antibody.

The RS655 cell line, derived from CHO K1, constitutively expresses ScFv$_{HB58}$-TM$_{PDGFR}$. Cells expressing ScFv$_{HB58}$-TM$_{PDGFR}$ can be stained by sequential incubation with P12 mAb, FD2-hFc, and FITC-conjugated anti-hIgG-P12 captured on the cell surface by the HB58 ScFv was detected by its affinity for FD2, which in turn was detected by recognition of the hFc tag. RS656 cells were derived from RS655 cells after stable transfection with a plasmid encoding the gene for eYFP. Nearly 100% of RS656 cells were eYFP-positive, and most (76%) maintained expression of ScFv$_{HB58}$-TM$_{PDGFR}$ as detected by binding to FD2-hFc.

RS655 cells were stably transfected with pTE693, a plasmid capable of expressing the heavy and light chains of the P12 antibody, and conferring resistance to puromycin. The transfected culture was selected with puromycin for two weeks to yield a pool of cells that were heterogeneous with regard to P12 mAb expression (RS655/pTE693).

To determine if ScFv$_{HB58}$-TM$_{PDGFR}$ could function as a CSCP and facilitate isolation of antibody-producing cells from non-producers, equal numbers of RS656 cells and RS655/pTE693 cells were mixed and co-cultured. When P12 expressed from RS655/pTE693 cells was allowed to diffuse and bind to ScFv$_{HB58}$ on the surface of RS656 cells a large population of yellow cells were also positive for binding FD2-hFc. However, if the ScFv$_{HB58}$ on the surface of RS656 was bound with excess murine IgG, then only non-yellow cells were positive for binding FD2-hFc, demonstrating that expressing cells were effectively separated from non-expressing cells.

These data demonstrate that an ScFv can be made into a functional CSCP by targeting it to the cell membrane. The data also show that FASTR™ allows cells expressing a secreted antibody to be detected with the antibody's antigen.

Example 13

A Protein of Interest Comprising a T Cell Receptor Variable Region

A flow cytometry-based autologous secretion trap (FASTR™) method for isolating high expression clones of a cell line that expresses a protein of interest that is a TCR-Fc is prepared in a manner analogous to preparing a cell line that expresses an antibody of interest. High expression clones are identified by screening cells that display on their surface the TCR-Fc of interest bound to hFcγR.

In these examples, the CHO K1 cell line RGC10, comprising an inducible FcγR1 as a cell surface capture molecule, is employed. RGC10 is made to express recombinant TCR-Fc's by cloning TCR variable regions, in frame, to a human Fc region either directly in frame or with a linker sequence between the TCR variable regions and the human Fc region.

To make a protein of interest that is a dimer comprising an Fc-linked TCR α variable domain and an Fc-linked TCR β variable domain, RGC10 is transfected with two vectors: a first vector capable of expressing a TCR α variable domain fusion protein with a human Fc sequence, and a second vector capable of expressing a TCR β domain fusion protein with the same human Fc sequence. Each vector includes leader sequence (e.g., a secretion signal sequence) 5' with respect to the TCR variable region, and a selectable marker that is a drug resistance gene. Following each vector transfection, cells containing the vector are selected by an appropriate drug selection. The selection results in an RGC10 cell line having both the first and the second vectors. Cells expressing proteins of interest can be detected by one or more of an antibody to the β variable domain, an antibody to the α variable domain, and an antibody to the Fc domain.

To make a protein of interest that is a dimer comprising both an α and a β TCR variable domain fused to an Fc, RGC10 is transfected with a single vector encoding a protein of interest that is constructed as follows: a leader sequence (e.g., a secretion signal sequence), followed by a TCR variable β domain fused to a linker, where the linker is, in turn, fused to a TCR variable α domain, which in turn is fused to an Fc sequence. Alternatively, the single vector can be constructed as follows: a leader sequence (e.g., a secretion signal sequence), followed by a TCR variable α domain fused to a linker, where the linker is, in turn, fused to a TCR variable β domain, which in turn is fused to an Fc sequence. Cells expressing proteins of interest can be detected by one or more of an antibody to the β variable domain, an antibody to the α variable domain, and an antibody to the Fc domain.

To make proteins of interest, as above, which also comprise a TCR α and/or TCR β constant domain, the TCR variable domain (α or β) is fused to a TCR constant domain (e.g., TCR variable domain α is fused to TCR constant domain α, and TCR variable domain β is fused to TCR constant domain β), and the TCR variable+constant domain is fused directly or through a linker to the Fc domain. Cells expressing proteins of interest can be detected by one or more of an antibody to the β variable domain, an antibody to the α variable domain, and an antibody to the Fc domain.

Cells expressing desired amounts of the TCR-Fc are isolated using the same procedure as used in isolating 4SC622-producing cell lines described herein, using one or more of an antibody to the α variable domain, an antibody to the β variable domain, an antibody to the α constant domain, and antibody to the β constant domain, and an antibody to the Fc domain. Cells expressing the highest levels of the TCR-Fc are selected as TCR-Fc-producing cell lines.

Example 14

ScFv-based CSCP for the Isolation of Multiple IgG Isotypes and Bispecific Antibodies Genetically modified mice, whose immunoglobulin heavy chain VDJ region and immunoglobulin kappa chain VJ region of their genomes were replaced with the human orthologs (i.e., Velocimmune® mice; see U.S. Pat. No. 7,105,348, which is herein incorporated by reference in its entirety), were immunized with either an Fc fragment of a human IgG4 protein (hFc, or simply Fc; SEQ ID NO: 26), or a human ΔAdpFc polypeptide containing the dipeptide mutation (H95R, Y96F by IMGT; also known as Fc*; SEQ ID NO: 42). Monoclonal antibodies were obtained from the mice and screened for their ability to bind Fc, Fc*, or antibodies comprising Fc and/or Fc*. Three antibodies that were capable of binding Fc (Ab1, Ab2, Ab3) and three that were capable of binding Fc* (Ab4, Ab5, Ab6) were tested for their ability to bind molecules having one of the following formats: Fc/Fc, Fc/Fc* (which can be a bispecific antibody), and Fc*/Fc*.

Measurements to determine binding affinities and kinetic constants were made on a Biacore 2000 instrument. Antibodies (each of Ab1-Ab8) were captured onto an anti-mouse-Fc sensor surface (Mab capture format), and human Fc (SEQ ID NO 26) homodimers, human Fc* homodimers (SEQ ID NO:42), or Fc/Fc* heterodimers were injected over the surface. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln2/(60*$k_d$). As shown in Table 2 antibodies were of 3 distinct categories: Fc specific, Fc* specific, and those showing no discrimination between Fc and Fc* (non-specific). The Fc specific antibodies were dependent on amino acids His 95 and/or Tyr 96, since these antibodies do not bind human Fc* with its dipeptide mutation (H95R, Y96F). In contrast the Fc* specific antibodies were dependent on Arg 95 and/or Phe 96, since these antibodies do not bind wild type human Fc.

Example 15

Cell Lines Producing Ab2 and Ab2-derived ScFv-FcγR Fusion Protein

The heavy chain and the light chain of the Fc-specific Ab2 were sequenced. To manufacture the recombinant Ab2 antibody, an expression vector plasmid was constructed that encodes the heavy chain and an expression vector plasmid was constructed that encodes the light chain. Both vectors enable expression and secretion of the respective subunits in a CHO cell. To express the antibody, both plasmids were transfected into a CHO-K1 cell and stable transformants were isolated. Expression of the antibody chains was driven by the constitutive CMV promoter.

TABLE 2

Affinity of Antibodies - Surface Plasmon Resonance Studies

| Antibody | POI-Target | ka (M$^{-1}$s$^{-1}$) | kd (s$^{-1}$) | KD (M) | t½ (min) | Specificity |
|---|---|---|---|---|---|---|
| Ab1 | Fc/Fc | 1.07E+05 | 3.79E−04 | 3.54E−09 | 30 | Fc |
|  | Fc/Fc* | 8.16E+04 | 3.01E−04 | 3.69E−09 | 38 |  |
|  | Fc*/Fc* | NB | NB | NB | NB |  |
| Ab2 | Fc/Fc | 7.86E+04 | 3.50E−05 | 4.45E−10 | 330 | Fc |
|  | Fc/Fc* | 5.45E+04 | 1.00-06 | 1.84E−11 | 11550 |  |
|  | Fc*/Fc* | NB | NB | NB | NB |  |
| Ab3 | Fc/Fc | 1.77E+05 | 4.08E−02 | 2.30E−07 | 0.3 | Fc |
|  | Fc/Fc* | 4.51E+04 | 2.60E−02 | 5.77E−07 | 0.4 |  |
|  | Fc*/Fc* | NB | NB | NB | NB |  |
| Ab4 | Fc/Fc | NB | NB | NB | NB | Fc* |
|  | Fc/Fc* | 6.00E+03 | 1.00E−06 | 2.00E−10 | 11550 |  |
|  | Fc*/Fc* | 2.22E+04 | 9.56E−06 | 4.50E−10 | 1209 |  |
| Ab5 | Fc/Fc | NB | NB | NB | NB | Fc* |
|  | Fc/Fc* | 3.11E+05 | 1.00E−06 | 3.21E−12 | 11550 |  |
|  | Fc*/Fc* | 5.57E+05 | 1.00E−06 | 1.79E−12 | 11550 |  |

TABLE 2-continued

Affinity of Antibodies - Surface Plasmon Resonance Studies

| Antibody | POI-Target | ka (M$^{-1}$s$^{-1}$) | kd (s$^{-1}$) | KD (M) | t½ (min) | Specificity |
|---|---|---|---|---|---|---|
| Ab6 | Fc/Fc | NB | NB | NB | NB | Fc* |
| | Fc/Fc* | 4.48E+05 | 7.43E−04 | 1.66E−09 | 16 | |
| | Fc*/Fc* | 8.73E+05 | 5.93E−04 | 6.79E−10 | 19 | |
| Ab7 | Fc/Fc | 6.02E+05 | 2.42E−04 | 4.02E−10 | 48 | Non-specific |
| | Fc/Fc* | 4.90E+05 | 2.15E−04 | 4.39E−10 | 54 | |
| | Fc*/Fc* | 4.46E+05 | 3.20E−02 | 7.18E−08 | 0.4 | |
| Ab8 | Fc/Fc | 2.59E+05 | 4.88E−04 | 1.88E−09 | 24 | Non-specific |
| | Fc/Fc* | 1.88E+05 | 4.02E−04 | 2.14E−09 | 29 | |
| | Fc*/Fc* | 4.10E+04 | 3.90E−02 | 9.60E−07 | 0.3 | |

The heavy chain and light chain sequences were used to develop an anti-Fc ScFv surface capture molecule. To manufacture the nucleic acid encoding the Ab2-derived anti-Fc ScFv-FcγR surface capture molecule, the Ab2 immunoglobulin heavy chain variable domain (SEQ ID NO:15) and the Ab2 immunoglobulin light chain variable domain (SEQ ID NO:16) amino acid sequences were reverse translated and codon optimized for CHO cell expression. Likewise, the C-terminal portion of human FcγRI was codon optimized for CHO cell expression. The codon optimized nucleotide sequences were amplified via polymerase chain reaction and ligated to form a contiguous nucleic acid sequence (SEQ ID NO:20) that encodes the ScFv-FcγR fusion protein of SEQ ID NO:19.

The nucleic acid encoding the ScFv-FcγR-TM-cyto fusion protein was inserted into an expression vector using standard PCR and restriction endonuclease cloning techniques. The resultant circular plasmid, exemplified in SEQ ID NO:23, comprises a beta-lactamase-encoding nucleic acid sequence, and two operons. The first operon comprises a nucleic acid sequence encoding yellow fluorescence protein (YFP), a variant of green fluorescent protein, in frame with a neomycin resistance marker, driven by an SV40 promoter (e.g., SEQ ID NO:24). The second operon, which is the "business-end" of the vector for the purposes of this aspect of the invention, comprises a nucleic acid sequence encoding the codon-optimized ScFv-FcγR fusion protein, driven by an hCMV-IE promoter and hCMV intron (e.g., SEQ ID NO:25).

CHO-K1 cells were transfected with the plasmid of SEQ ID NO:23. Stable integrants, which have integrated the linear construct of SEQ ID NO:22 into their genomes, were isolated.

The circular plasmid contains two Lox sites flanking the first operon and the second operon, to allow for the integration of those operons as a linear construct into the genome of the host cell. The linear construct spanning from the first Lox site to the second Lox site is exemplified in SEQ ID NO:22 and comprises from 5-prime to 3-prime: SV40 promoter, nucleic acid encoding neomycin-resistance, IRES, nucleic acid encoding eYFP, SV40 polyadenylation sequence, hCMV-IE promoter, hCMV intron, Tet-operator sequence (for controlled expression of the ScFv-FcγR-TM-cyto fusion protein), nucleic acid encoding mROR signal sequence, nucleic acid encoding Ab2 ScFv, nucleic acid encoding the FcγR transmembrane and cytoplasmic portion (SEQ ID NO: 21), and SV40 polyadenylation sequence.

Example 16

ScFv-FcγR-TM-cyto Surface Capture Targets

CHO-K1 cells containing the integrated sequence of SEQ ID NO:22 were transfected with plasmids that encode antibodies of various subtypes, e.g., IgG1, IgG2, IgG4, an IgG4 bispecific antibody containing one CH3 domain with the 95R/435R-96F/436F dual substitution while the other CH3 domain is wild-type (IgG4 Fc/Fc*), and an IgG1 bispecific antibody of the IgG1 Fc/Fc* format. The cells were treated with doxycycline to induce production of the capture molecule along with the antibody. After co-expression of the antibody and capture molecule, the cells in some cases were treated with hFc blocking protein, and detection molecule (FITC-labeled anti-hFab). Table 3 summarizes the results, and generally shows that the ScFv-FcγR surface capture fusion protein binds IgG4, IgG2, and IgG1 molecules, while the wildtype FcγR surface capture molecule binds IgG1, but not IgG4 or IgG2.

TABLE 3

Blocking Molecule Competition Assays

| | Arbitrary FITC Units (with or without hFc blocking molecule) - Mode | | | | | hFc |
|---|---|---|---|---|---|---|
| Antibody | No hFc | hFc (1 hr) | hFc (2 hr) | hFc (20 hr) | No coat | displacement? |
| | Capture molecule = ScFv-FcγR-TM-cyto Detection molecule = FITC-anti-hFab | | | | | |
| IgG1 mAb-3 | 250 | 120 | 80 | 20 | 10 | Yes |
| IgG4 mAb-4 | 250 | 100 | 55 | 20 | 10 | Yes |
| IgG4 mAb-5 | 250 | 70 | 40 | 20 | 10 | Yes |
| IgG2 mAb-6 | 200[1] | ND | ND | ND | 12[2] | Yes |

TABLE 3-continued

Blocking Molecule Competition Assays

| Antibody | Arbitrary FITC Units (with or without hFc blocking molecule) - Mode | | | | | hFc displacement? |
|---|---|---|---|---|---|---|
| | No hFc | hFc (1 hr) | hFc (2 hr) | hFc (20 hr) | No coat | |
| | Capture molecule = hFcγR Detection molecule = FITC-anti-hFab | | | | | |
| IgG1 mAb-3 | 300 | 80 | 30 | 9 | 3.5 | Yes |
| IgG4 mAb-4 | 100 | 2 | 2 | 2 | 2 | No |
| IgG4 mAb-5 | 35 | 5 | 5 | 5 | 5 | No |

[1]+Dox
[2]−Dox

Example 17

Cell Lines Producing Ab6 and Ab6-derived ScFv*-FcγR-TM-cyto

The heavy chain and the light chain of the Fc*-specific Ab6 were sequenced. The amino acid sequence of the light chain was determined to be SEQ ID NO:41. The amino acid sequence of the heavy chain was determined to be SEQ ID NO:40. To manufacture the recombinant Ab6 antibody, an expression vector plasmid was constructed that encodes the heavy chain and an expression vector plasmid was constructed that encodes the light chain. To express the antibody, both plasmids were transfected into a CHO-K1 cell, stable transformants were isolated, and expression was driven by the constitutive CMV promoter.

To manufacture the nucleic acid encoding the Ab6-derived anti-Fc*-specific ScFv*-FcγR surface capture molecule, the immunoglobulin heavy chain variable domain of the Ab6 antibody (SEQ ID NO:38) and the immunoglobulin light chain variable domain of Ab6 (SEQ ID NO:39) amino acid sequences were reverse translated and codon optimized for CHO cell expression. Likewise, the C-terminal portion of human FcγRI (SEQ ID NO: 21) was codon optimized for CHO cell expression. The codon optimized nucleotide sequences were amplified via polymerase chain reaction and ligated to form a contiguous nucleic acid sequence (SEQ ID NO:45) that encodes the anti-Fc* ScFv*-FcγR fusion protein (SEQ ID NO:43).

The nucleic acid encoding the ScFv*-FcγR-TM-cyto fusion protein was inserted into an expression vector using standard PCR and restriction endonuclease cloning techniques. The resultant circular plasmid, exemplified in SEQ ID NO:44, comprises a beta-lactamase-encoding nucleic acid sequence, and two operons. The first operon comprises a nucleic acid sequence encoding yellow fluorescence protein (YFP), a variant of green fluorescent protein, in frame with a neomycin resistance marker, driven by an SV40 promoter (e.g., SEQ ID NO:46). The second operon, which is the "business-end" of the vector for the purposes of this aspect of the invention, comprises a nucleic acid sequence encoding the codon-optimized anti-Fc* ScFv-FcγR fusion protein, driven by an hCMV-IE promoter and hCMV intron (e.g., SEQ ID NO:47).

CHO-K1 cells were transfected with the plasmid of SEQ ID NO:44. Stable integrants, which have integrated the linear construct of SEQ ID NO:48, were isolated.

The circular plasmid contains two Lox sites flanking the first operon and the second operon, to allow for the integration of those operons as a linear construct into the genome of the host cell. The linear construct spanning from the first Lox site to the second Lox site is exemplified in SEQ ID NO:48 and comprises from 5-prime to 3-prime: SV40 promoter, nucleic acid encoding neomycin-resistance, IRES, nucleic acid encoding eYFP, SV40 polyadenylation sequence, hCMV-IE promoter, hCMV intron, Tet-operator sequence (for controlled expression of the anti-Fc* ScFv*-FcγR fusion protein), nucleic acid encoding mROR signal sequence, nucleic acid encoding the Ab6-derived anti-Fc*-specific ScFv*, nucleic acid encoding the FcγR transmembrane and cytoplasmic domain polypeptide (SEQ ID NO: 21), and SV40 polyadenylation sequence.

Example 18

Sorting Bispecific Antibodies

Anti-Fc Capture & Anti-Fc* Detection

The Ab2-derived anti-Fc-specific ScFv-FcγR surface capture system was tested for its ability to detect and enrich for cells that produce bispecific antibodies. To assess the ability to detect bispecific antibodies, which harbor the 95R/435R-96F/436F substitution in one of the CH3 domains (designated Fc*), various antibodies were expressed in the Ab2-derived anti-Fc-specific ScFv-FcγR surface capture cell line, using hFc as the blocking molecule, and a FITC-labeled Ab6 anti-Fc* antibody (e.g., mAb with HC of SEQ ID NO:40, and LC of SEQ ID NO:41) as the detection molecule. The Ab2-derived anti-Fc-specific ScFv-FcγR surface capture cell line was able to detect and distinguish the bispecific antibody (Fc/Fc*) over any Fc*/Fc* or Fc/Fc monospecific antibodies using the Fc*-specific Ab6 as the detection molecule (Table 4). The wildtype FcγR surface capture cell line was not able to distinguish between the Fc/Fc*, Fc*/Fc*, and Fc/Fc IgG4 species, since FcγR is unable to bind, or binds at very low affinity to IgG4.

Anti-Fc* Capture & Anti-Fc Detection

Conversely, the Ab6-derived anti-Fc*-specific ScFv*-FcγR surface capture system was tested for its ability to detect and enrich for cells that produce bispecific antibodies. To assess the ability to detect bispecific antibodies, which harbor the 95R/435R-96F/436F substitution in one of the CH3 domains (designated Fc*), various antibodies were expressed in the Ab6-derived anti-Fc*-specific ScFv*-FcγR surface capture cell line, using hFc as the blocking molecule, and an Alexa 488-labeled Ab2 anti-Fc antibody, which recognizes non-substituted CH3, as the detection molecule. The Ab6-derived anti-Fc*-specific ScFv*-FcγR surface capture cell line was able to detect and distinguish the bispecific antibody (Fc/Fc*) over the Fc*/Fc* or Fc/Fc monospecific antibodies using the Fc-specific Ab2 as the detection molecule (Table 4). The FcγR surface capture cell line was not able to distinguish between the Fc/Fc*, Fc*/Fc*, and Fc/Fc IgG4 species.

TABLE 4

Detection of Bispecific Antibody - Mean Fluorescence Intensity (MFI)

| | | IgG1 | | | IgG4 | | | |
|---|---|---|---|---|---|---|---|---|
| ¹CSCP | ²DM | Fc/Fc* | Fc*/Fc* | Fc/Fc | Fc/Fc* | Fc*/Fc* | Fc/Fc | Fc/Fc*Specificity |
| FcγR | Ab2 | 500 | ND | 350 | 200 | 200 | 200 | NO |
| | Ab6 | 200 | 200 | 200 | ND | ND | ND | NO |
| | Anti-hFc | 1800 | ND | 1000 | ND | ND | ND | NO |
| ScFv-FcγR | Ab6 | 500 | 15 | 15 | 500 | 15 | 15 | YES |
| | Anti-hFc | ND | ND | ND | ND | ND | ND | ND |
| ScFv*-FcγR | Ab2 | 150 | 10 | 10 | ND | ND | ND | YES |
| | Anti-hFc | 200 | ND | 10 | ND | ND | ND | YES |

¹Cell surface capture protein
²Detection molecule

Example 19

Enrichment of Fc/Fc* Bispecific Antibodies

To assess the ability of the (Ab2-derived) ScFv-FcγR CSCP/(Ab6) anti-Fc* DM and the (Ab6-derived) ScFv*-FcγR CSCP/(Ab2) anti-Fc DM systems to sort and enrich bispecific antibodies, cell lines co-expressing an Fc/Fc* IgG4 monoclonal antibody (IgG4-mAb-2) and the anti-Fc ScFv-FcγR fusion protein, using hFc as the blocking molecule and the FITC-labeled anti-Fc* (Ab6) antibody as the detection molecule, were subjected to serial fluorescence activated cell sorting and pooling to enrich for production of the Fc/Fc* species. Cells yielding Fc/Fc* from the fifth and sixth series pools were analyzed for total antibody titer and titers of each antibody format: Fc/Fc*, Fc/Fc, and Fc*/Fc*. Since the cells encode both a heavy chain encoding the non-substituted CH3 domain ("Fc", i.e., comprising a histidine at IMGT position 95 and a tyrosine at IMGT position 96) and a heavy chain encoding the substituted CH3 domain ("Fc*", i.e., comprising an arginine at IMGT position 95 and a phenylalanine at IMGT position 96), by purely mathematical Punnett square analysis, the cell is theoretically expected to produce 25% Fc/Fc, 50% Fc/Fc*, and 25% Fc*/Fc*. Biologically, however, one might expect (pre-enrichment) most of the antibody produced to be Fc/Fc.

As shown in Table 5, cells selected, pooled, and enriched for bispecific antibody production produced as much as 49% Fc/Fc* species, with titers of Fc/Fc* bispecific antibodies of at least about 3.2 g/L.

TABLE 5

Enrichment of Fc/Fc* bispecific antibody IgG4-mAb-2

| pool | Cell line | Fc/Fc* Titer (g/L) | % | Fc/Fc Titer (g/L) | % | Fc*/Fc* Titer (g/L) | % |
|---|---|---|---|---|---|---|---|
| 5 | 1 | 1.2 | 28 | 2.2 | 50 | 0.99 | 23 |
| | 2 | 1.9 | 49 | 1.3 | 32 | 0.73 | 19 |
| | 3 | 1.5 | 47 | 1.2 | 40 | 0.40 | 13 |
| | 4 | 1.6 | 37 | 1.3 | 31 | 1.3 | 32 |
| | 5 | 1.5 | 48 | 1.1 | 35 | 0.58 | 18 |
| | 6 | 1.8 | 47 | 1.3 | 33 | 0.75 | 20 |
| 6 | 7 | 2.6 | 44 | 2.0 | 34 | 1.3 | 23 |
| | 8 | 3.2 | 42 | 2.4 | 31 | 2.0 | 27 |
| | 9 | 2.1 | 45 | 1.5 | 33 | 1.0 | 22 |
| | 10 | 2.8 | 43 | 2.0 | 31 | 1.7 | 28 |
| | 11 | 2.3 | 44 | 1.6 | 31 | 1.3 | 24 |

Although the foregoing invention has been described in some detail by way of illustration and example, it will be readily apparent to those of ordinary skill in the art that certain changes and modifications may be made to the teachings of the invention without departing from the spirit or scope of the appended claims.

What is claimed:

1. A recombinant antigen-binding protein that binds a human IgG1-Fc domain, a human IgG2-Fc domain, or a human IgG4-Fc domain, wherein the antigen-binding protein comprises a heavy chain CDR-1 (HCDR-1) having the amino acid sequence of SEQ ID NO:27, an HCDR-2 having the amino acid sequence of SEQ ID NO:28, an HCDR-3 having the amino acid sequence of SEQ ID NO:29, and a light chain variable region having the amino acid sequence of SEQ ID NO: 16.

2. The recombinant antigen-binding protein of claim 1, wherein the antigen-binding protein binds a polypeptide comprising an amino acid sequence of SEQ ID NO:26.

3. The recombinant antigen-binding protein of claim 2, wherein the antigen-binding protein binds the polypeptide with a KD of less than about 40 nM as measured in a surface plasmon resonance assay.

4. The recombinant antigen-binding protein of claim 2, wherein the antigen-binding protein comprises an HCVR having an amino acid sequence that is at least 95% identical to SEQ ID NO:15.

5. The recombinant antigen-binding protein of claim 4, wherein the antigen-binding protein comprises an HCVR having the amino acid sequence of SEQ ID NO:15.

6. The recombinant antigen-binding protein of claim 4, wherein the antigen-binding protein is an ScFv fusion protein comprising (a) a heavy chain variable domain comprising an amino acid sequence that is at least 95% identical to SEQ ID NO:15, and (b) a membrane anchor domain comprising an amino acid sequence that is at least 95% identical to SEQ ID NO:17 or SEQ ID NO:21.

7. The recombinant antigen-binding protein of claim 6, wherein the antigen-binding protein is an ScFv fusion protein comprising a heavy chain variable domain that has an amino acid sequence identical to SEQ ID NO:15.

8. The recombinant antigen-binding protein of claim 7, wherein the antigen-binding protein is an ScFv fusion protein comprising the amino acid sequence of SEQ ID NO:19.

* * * * *

```
                       SEQUENCE LISTING

<160> NUMBER OF SEQ ID NOS: 51

<210> SEQ ID NO 1
<211> LENGTH: 195
<212> TYPE: PRT
<213> ORGANISM: Streptococcus

<400> SEQUENCE: 1

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
                20                  25                  30

Ala Asn Asp Asn Gly Val Asp Gly Glu Trp Thr Tyr Asp Asp Ala Thr
            35                  40                  45

Lys Thr Phe Thr Val Thr Glu Lys Pro Glu Val Ile Asp Ala Ser Glu
        50                  55                  60

Leu Thr Pro Ala Val Thr Thr Tyr Lys Leu Val Ile Asn Gly Lys Thr
```

```
                65                  70                  75                  80
Leu Lys Gly Glu Thr Thr Thr Glu Ala Val Asp Ala Ala Thr Ala Glu
                    85                  90                  95

Lys Val Phe Lys Gln Tyr Ala Asn Asp Asn Gly Val Asp Gly Glu Trp
                100                 105                 110

Thr Tyr Asp Asp Ala Thr Lys Thr Phe Thr Val Thr Glu Lys Pro Glu
                115                 120                 125

Val Ile Asp Ala Ser Glu Leu Thr Pro Ala Val Thr Thr Tyr Lys Leu
        130                 135                 140

Val Ile Asn Gly Lys Thr Leu Lys Gly Glu Thr Thr Thr Lys Ala Val
145                 150                 155                 160

Asp Ala Glu Thr Ala Glu Lys Ala Phe Lys Gln Tyr Ala Asn Asp Asn
                165                 170                 175

Gly Val Asp Gly Val Trp Thr Tyr Asp Asp Ala Thr Lys Thr Phe Thr
                180                 185                 190

Val Thr Glu
        195

<210> SEQ ID NO 2
<211> LENGTH: 96
<212> TYPE: PRT
<213> ORGANISM: Homo sapiens

<400> SEQUENCE: 2

Gln Val Leu Gly Leu Gln Leu Pro Thr Pro Val Trp Phe His Val Leu
1               5                   10                  15

Phe Tyr Leu Ala Val Gly Ile Met Phe Leu Val Asn Thr Val Leu Trp
                20                  25                  30

Val Thr Ile Arg Lys Glu Leu Lys Arg Lys Lys Lys Trp Asp Leu Glu
            35                  40                  45

Ile Ser Leu Asp Ser Gly His Glu Lys Lys Val Thr Ser Ser Leu Gln
        50                  55                  60

Glu Asp Arg His Leu Glu Glu Glu Leu Lys Cys Gln Glu Gln Lys Glu
65                  70                  75                  80

Glu Gln Leu Gln Glu Gly Val His Arg Lys Pro Gln Gly Ala Thr
                85                  90                  95

<210> SEQ ID NO 3
<211> LENGTH: 33
<212> TYPE: DNA
<213> ORGANISM: artificial sequence
<220> FEATURE:
<223> OTHER INFORMATION: synthetic

<400> SEQUENCE: 3
cgggctgatg ctgcaccaac tgtatccatc ttc                                33

<210> SEQ ID NO 4
<211> LENGTH: 33
<212> TYPE: DNA
<213> ORGANISM: artificial sequence
<220> FEATURE:
<223> OTHER INFORMATION: synthetic

<400> SEQUENCE: 4
acactctccc ctgttgaagc tcttgacaat ggg                                33

<210> SEQ ID NO 5
<211> LENGTH: 31
```

```
<212> TYPE: DNA
<213> ORGANISM: artificial sequence
<220> FEATURE:
<223> OTHER INFORMATION: synthetic

<400> SEQUENCE: 5
gccaaaacaa cagccccatc ggtctatcca c                            31

<210> SEQ ID NO 6
<211> LENGTH: 35
<212> TYPE: DNA
<213> ORGANISM: artificial sequence
<220> FEATURE:
<223> OTHER INFORMATION: synthetic

<400> SEQUENCE: 6
tcatttaccc ggagtccggg agaagctctt agtcg                        35

<210> SEQ ID NO 7
<211> LENGTH: 47
<212> TYPE: DNA
<213> ORGANISM: artificial sequence
<220> FEATURE:
<223> OTHER INFORMATION: synthetic

<400> SEQUENCE: 7
gagagtacct gcgtcatgca gatgtgaaac tgcaggagtc tggccct           47

<210> SEQ ID NO 8
<211> LENGTH: 38
<212> TYPE: DNA
<213> ORGANISM: artificial sequence
<220> FEATURE:
<223> OTHER INFORMATION: synthetic

<400> SEQUENCE: 8
gagagacctg cgtcagctga ggagacggtg accgtggt                     38

<210> SEQ ID NO 9
<211> LENGTH: 35
<212> TYPE: DNA
<213> ORGANISM: artificial sequence
<220> FEATURE:
<223> OTHER INFORMATION: synthetic

<400> SEQUENCE: 9
gagagggtct cacagccaaa acaacagccc catcg                        35

<210> SEQ ID NO 10
<211> LENGTH: 42
<212> TYPE: DNA
<213> ORGANISM: artificial sequence
<220> FEATURE:
<223> OTHER INFORMATION: synthetic

<400> SEQUENCE: 10
gagagggtct ccggccgctc atttacccgg agtccgggag aa                42

<210> SEQ ID NO 11
<211> LENGTH: 40
<212> TYPE: DNA
<213> ORGANISM: artificial sequence
<220> FEATURE:
<223> OTHER INFORMATION: synthetic

<400> SEQUENCE: 11
```
gagagcgtct catgcagaca tccagatgac ccagtctcca                40

<210> SEQ ID NO 12
<211> LENGTH: 40
<212> TYPE: DNA
<213> ORGANISM: artificial sequence
<220> FEATURE:
<223> OTHER INFORMATION: synthetic

<400> SEQUENCE: 12
gagagcgtct cacagcccgt tttatttcca gcttggtccc                40

<210> SEQ ID NO 13
<211> LENGTH: 36
<212> TYPE: DNA
<213> ORGANISM: artificial sequence
<220> FEATURE:
<223> OTHER INFORMATION: synthetic

<400> SEQUENCE: 13
gagagggtct cagctgatgc tgcaccaact gtatcc                    36

<210> SEQ ID NO 14
<211> LENGTH: 48
<212> TYPE: DNA
<213> ORGANISM: artificial sequence
<220> FEATURE:
<223> OTHER INFORMATION: synthetic

<400> SEQUENCE: 14
gagagggtct caggccgctc aacactctcc cctgttgaag ctcttgac       48

<210> SEQ ID NO 15
<211> LENGTH: 113
<212> TYPE: PRT
<213> ORGANISM: Homo sapiens

<400> SEQUENCE: 15

Gln Leu Gln Gln Ser Gly Ala Glu Leu Ala Lys Pro Gly Ala Ser Val
1               5                   10                  15
Lys Met Ser Cys Lys Ala Ser Gly Tyr Thr Phe Thr Asn Tyr Trp Ile
            20                  25                  30
His Trp Glu Lys Gln Arg Pro Glu Gln Gly Leu Glu Trp Ile Gly Tyr
        35                  40                  45
Ile Asn Pro Asn Thr Gly His Thr Glu Tyr Asn Gln Lys Phe Lys Asp
    50                  55                  60
Lys Ala Thr Leu Thr Ala Asp Arg Ser Ser Thr Ala Tyr Met Gln
65                  70                  75                  80
Leu Ser Ser Leu Thr Ser Glu Asp Ser Ala Val Tyr Phe Cys Ala Arg
            85                  90                  95
Thr Tyr Ser Gly Ser Ser His Phe Asp Tyr Trp Gly Gln Gly Thr Thr
            100                 105                 110
Leu

<210> SEQ ID NO 16
<211> LENGTH: 112
<212> TYPE: PRT
<213> ORGANISM: Homo sapiens

<400> SEQUENCE: 16

Ser Asp Ile Val Met Thr Gln Thr Pro Val Ser Leu Pro Val Ser Leu
1               5                   10                  15

Gly Asp Gln Ala Ser Ile Ser Cys Arg Ser Ser Gln Ser Leu Val His
            20                  25                  30

Asn Asn Gly Asp Thr Phe Leu His Trp Tyr Leu Gln Lys Pro Gly Gln
        35                  40                  45

Ser Pro Lys Leu Leu Ile Tyr Lys Val Ser Asn Arg Phe Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Leu Gly Val Tyr Phe Cys Ser Gln
                85                  90                  95

Thr Thr Leu Ile Pro Arg Thr Phe Gly Gly Gly Thr Lys Leu Glu Ile
            100                 105                 110

<210> SEQ ID NO 17
<211> LENGTH: 21
<212> TYPE: PRT
<213> ORGANISM: Homo sapiens

<400> SEQUENCE: 17

Val Leu Phe Tyr Leu Ala Val Gly Ile Met Phe Leu Val Asn Thr Val
 1               5                  10                  15

Leu Trp Val Thr Ile
            20

<210> SEQ ID NO 18
<211> LENGTH: 61
<212> TYPE: PRT
<213> ORGANISM: Homo sapiens

<400> SEQUENCE: 18

Arg Lys Glu Leu Lys Arg Lys Lys Lys Trp Asp Leu Glu Ile Ser Leu
 1               5                  10                  15

Asp Ser Gly His Glu Lys Lys Val Thr Ser Ser Leu Gln Glu Asp Arg
            20                  25                  30

His Leu Glu Glu Glu Leu Lys Cys Gln Glu Gln Lys Glu Glu Gln Leu
        35                  40                  45

Gln Glu Gly Val His Arg Lys Glu Pro Gln Gly Ala Thr
 50                  55                  60

<210> SEQ ID NO 19
<211> LENGTH: 334
<212> TYPE: PRT
<213> ORGANISM: artificial sequence
<220> FEATURE:
<223> OTHER INFORMATION: synthetic

<400> SEQUENCE: 19

Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Asn Tyr
            20                  25                  30

Trp Ile His Trp Glu Lys Gln Arg Pro Glu Gln Gly Leu Glu Trp Ile
        35                  40                  45

Gly Tyr Ile Asn Pro Asn Thr Gly His Thr Glu Tyr Asn Gln Lys Phe
 50                  55                  60

Lys Asp Lys Ala Thr Leu Thr Ala Asp Arg Ser Ser Ser Thr Ala Tyr
 65                  70                  75                  80

Met Gln Leu Ser Ser Leu Thr Ser Glu Asp Ser Ala Val Tyr Phe Cys

```
            85                  90                  95
Ala Arg Thr Tyr Ser Gly Ser Ser His Phe Asp Tyr Trp Gly Gln Gly
                100                 105                 110

Thr Thr Leu Ile Val Ser Ser Gly Gly Gly Ser Gly Gly Gly Gly
            115                 120                 125

Ser Gly Gly Gly Ser Asp Ile Val Met Thr Gln Thr Pro Val Ser
        130                 135                 140

Leu Pro Val Ser Leu Gly Asp Gln Ala Ser Ile Ser Cys Arg Ser Ser
145                 150                 155                 160

Gln Ser Leu Val His Asn Asn Gly Asp Thr Phe Leu His Trp Tyr Leu
                165                 170                 175

Gln Lys Pro Gly Gln Ser Pro Lys Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Leu Gly Val
    210                 215                 220

Tyr Phe Cys Ser Gln Thr Thr Leu Ile Pro Arg Thr Phe Gly Gly Gly
225                 230                 235                 240

Thr Lys Leu Glu Ile Lys Arg Gly Gly Gly Gly Ser Val Leu Phe Tyr
                245                 250                 255

Leu Ala Val Gly Ile Met Phe Leu Val Asn Thr Val Leu Trp Val Thr
            260                 265                 270

Ile Arg Lys Glu Leu Lys Arg Lys Lys Trp Asp Leu Glu Ile Ser
        275                 280                 285

Leu Asp Ser Gly His Glu Lys Lys Val Thr Ser Ser Leu Gln Glu Asp
    290                 295                 300

Arg His Leu Glu Glu Glu Leu Lys Cys Gln Glu Gln Lys Glu Glu Gln
305                 310                 315                 320

Leu Gln Glu Gly Val His Arg Lys Glu Pro Gln Gly Ala Thr
                325                 330

<210> SEQ ID NO 20
<211> LENGTH: 1005
<212> TYPE: DNA
<213> ORGANISM: artificial sequence
<220> FEATURE:
<223> OTHER INFORMATION: synthetic

<400> SEQUENCE: 20
caagtacaac tgcaacaaag cggagctgaa ctggccaaac caggcgcttc cgtgaagatg    60
tcttgtaaag ccagcgggta catttact aattactgga ttcactggga gaagcaaaga   120
cctgaacagg gattggaatg gattggatac attaatccta acaccggaca cagagtat    180 aatcaaaaat tcaaggataa ggccaccctc acagccgaca tcttcttc aaccgcctat    240 atgcaacttt cttccctcac ttctgaagac tccgcagttt actttgcgc acgaacttat   300 tctggaagct cccatttcga ctactgggt caaggaacaa cactgatcgt gtctagcggc    360
ggcggagggt ccggcggggg cggtagcggt ggcggaggtt ctgatattgt catgactcaa   420
acacctgtct ctctgcctgt ttcacttgga gatcaagcta gcatttcctg ccgctctagt    480
caatctctcg tccacaacaa cggcgatact ttcttgcatt ggtatctgca gaaaccaggt   540
cagtcaccta aactgcttat atacaaagtc tctaatagat ctcagggggt gccagatcga   600
ttcagtggtt ctgggtccgg tacagatttt acactcaaga tatccagagt agaagcagaa   660
```

| | |
|---|---|
| gatctgggcg tgtatttctg cagtcaaaca acacttattc ctcgtacttt tggaggcggt | 720 |
| acaaaactgg agatcaagcg tggaggcgga gggagtgttt tgttttatct ggccgttggg | 780 |
| ataatgtttc tcgtaaatac agtactttgg gtaacaataa ggaaggaact gaagagaaag | 840 |
| aaaaaatggg atctggaaat atcattggac agtggacacg aaaaaaaagt cacatcatca | 900 |
| ttgcaagaag accggcactt ggaggaggaa ctgaaatgtc aagagcaaaa agaagaacaa | 960 |
| ctgcaagaag gcgtacatag aaaagaacca cagggagcaa catag | 1005 |

```
<210> SEQ ID NO 21
<211> LENGTH: 82
<212> TYPE: PRT
<213> ORGANISM: Homo sapiens

<400> SEQUENCE: 21

Val Leu Phe Tyr Leu Ala Val Gly Ile Met Phe Leu Val Asn Thr Val
1               5                   10                  15

Leu Trp Val Thr Ile Arg Lys Glu Leu Lys Arg Lys Lys Lys Trp Asp
            20                  25                  30

Leu Glu Ile Ser Leu Asp Ser Gly His Glu Lys Lys Val Thr Ser Ser
        35                  40                  45

Leu Gln Glu Asp Arg His Leu Glu Glu Leu Lys Cys Gln Glu Gln
    50                  55                  60

Lys Glu Glu Gln Leu Gln Glu Gly Val His Arg Lys Glu Pro Gln Gly
65                  70                  75                  80

Ala Thr

<210> SEQ ID NO 22
<211> LENGTH: 5759
<212> TYPE: DNA
<213> ORGANISM: artificial sequence
<220> FEATURE:
<223> OTHER INFORMATION: synthetic

<400> SEQUENCE: 22
```

| | |
|---|---|
| acaacttcgt atagcataca ttatacgaag ttatggtacc aagcctaggc ctccaaaaaa | 60 |
| gcctcctcac tacttctgga atagctcaga ggcagaggcg gcctcggcct ctgcataaat | 120 |
| aaaaaaaatt agtcagccat ggggcggaga atgggcggaa ctgggcggag ttaggggcgg | 180 |
| gatgggcgga gttaggggcg ggactatggt tgctgactaa ttgagatgca tgctttgcat | 240 |
| acttctgcct gctggggagc ctggggactt ccacacctg gttgctgact aattgagatg | 300 |
| catgctttgc atacttctgc ctgctgggga gcctgggggac tttccacacc ggatccacca | 360 |
| tgggttcagc tattgagcag gatgggttgc atgctggtag tcccgccgca tgggtcgaac | 420 |
| gactgttggg atacgattgg gcccaacaga ctataggctg ttccgacgct gctgtctttc | 480 |
| gtctttctgc acaaggtcgt ccagttctgt tcgtgaaaac cgacttgtcc ggagccctca | 540 |
| atgagttgca agacgaagct gcacgactga gttggcttgc caccactggt gtcccatgtg | 600 |
| ccgcagtact tgacgtcgtc acagaggctg gtcgcgattg gttgctcctt ggagaagtgc | 660 |
| ccggccaaga tcttctcagt tcccaccttg cccctgccga aaagtttca ataatggctg | 720 |
| acgctatgag aaggctgcac acccttgacc ctgccacatg tccattcgat caccaagcca | 780 |
| aacaccgaat tgaacgagct agaacccgca tggaagccgg cctcgttgat caagacgatt | 840 |
| tggatgagga acaccagggt ctcgcacccg ctgaactctt cgctcgcctc aaagcacgaa | 900 |
| tgccagacgg agatgacttg gtcgtaaccc acggagatgc ctgccttcct aacataatgg | 960 |

```
tagagaatgg aagatttagc ggcttcattg attgtggacg acttggagtt gcagatcggt    1020
accaagatat cgctctcgct accagagata ttgctgaaga attgggcgga gaatgggctg    1080
atcggtttct cgtactctac ggaattgccg cacctgattc ccaacgcatt gcttttacc    1140 gtcttctgga tgagttcttc taaacgcgtc cccctctcc ctccccccc cctaacgtta     1200 ctggccgaag ccgcttggaa taaggccggt gtgcgtttgt ctatatgtta ttttccacca   1260
tattgccgtc ttttggcaat gtgagggccc ggaaacctgg ccctgtcttc ttgacgagca   1320
ttcctagggg tctttcccct ctcgccaaag gaatgcaagg tctgttgaat gtcgtgaagg   1380
aagcagttcc tctggaagct tcttgaagac aaacaacgtc tgtagcgacc ctttgcaggc   1440
agcggaaccc cccacctggc gacaggtgcc tctgcggcca aaagccacgt gtataagata   1500
cacctgcaaa ggcggcacaa ccccagtgcc acgttgtgag ttggatagtt gtggaaagag   1560
tcaaatggct ctcctcaagc gtattcaaca aggggctgaa ggatgccag aaggtacccc    1620 attgtatggg atctgatctg gggcctcggt gcacatgctt tacatgtgtt tagtcgaggt   1680
taaaaaacgt ctaggccccc cgaaccacgg ggacgtggtt ttcctttgaa aaacacgatt   1740
gctcgaatca ccatggtgag caagggcgag gagctgttca ccggggtggt gcccatcctg   1800
gtcgagctgg acggcgacgt aaacggccac aagttcagcg tgtccggcga gggcgagggc   1860
gatgccacct acggcaagct gaccctgaag ttcatctgca ccaccggcaa gctgcccgtg   1920
ccctggccca cccttcggc tacggcctgc agtgcttcgc ccgctacccc                1980
gaccacatga agcagcacga cttcttcaag tccgccatgc ccgaaggcta cgtccaggag   2040
cgcaccatct tcttcaagga cgacggcaac tacaagaccc gcgccgaggt gaagttcgag   2100
ggcgacaccc tggtgaaccg catcgagctg aagggcatcg acttcaagga ggacggcaac   2160
atcctggggc acaagctgga gtacaactac aacagccaca acgtctatat catggccgac   2220
aagcagaaga cggcatcaa ggtgaacttc aagatccgcc acaacatcga ggacggcagc    2280
gtgcagctcg ccgaccacta ccagcagaac acccccatcg cgacggcccc cgtgctgctg   2340
cccgacaacc actacctgag ctaccagtcc gccctgagca agacccccaa cgagaagcgc   2400
gatcacatgg tcctgctgga gttcgtgacc gccgccggga tcactctcgg catggacgag   2460
ctgtacaagt aatcggccgc taatcagcca taccacattt gtagaggttt tacttgcttt   2520
aaaaaacctc ccacacctcc ccctgaacct gaaacataaa atgaatgcaa ttgttgttgt   2580
taacttgttt attgcagctt ataatggtta caaataaagc aatagcatca caaatttcac   2640
aaataaagca ttttttttcac tgcattctag ttgtggtttg tccaaactca tcaatgtatc   2700
ttatcatgtc ggcgcgttga cattgattat tgactagtta ttaatagtaa tcaattacgg   2760
ggtcattagt tcatagccca tatatggagt tccgcgttac ataacttacg gtaaatggcc   2820
cgcctggctg accgcccaac gacccccgcc cattgacgtc aataatgacg tatgttccca   2880
tagtaacgcc aatagggact ttccattgac gtcaatgggt ggagtattta cggtaaactg   2940
cccacttggc agtacatcaa gtgtatcata tgccaagtac gccccctatt gacgtcaatg   3000
acggtaaatg gcccgcctgg cattatgccc agtacatgac cttatgggac tttcctactt   3060
ggcagtacat ctacgtatta gtcatcgcta ttaccatggt gatgcggttt tggcagtaca   3120
tcaatgggcg tggatagcgg tttgactcac ggggatttcc aagtctccac cccattgacg   3180
tcaatgggag tttgttttgg caccaaaatc aacgggactt tccaaaatgt cgtaacaact   3240
ccgccccatt gacgcaaatg gcggtaggc gtgtacggtg ggaggtctat ataagcagag    3300
ctctccctat cagtgataga gatctcccta tcagtgatag agatcgtcga cgtttagtga   3360
```

```
accgtcagat cgcctggaga cgccatccac gctgttttga cctccataga agacaccggg    3420
accgatccag cctccgcggc cgggaacggt gcattggaac gcggattccc cgtgccaaga    3480
gtgacgtaag taccgcctat agagtctata ggcccacccc cttggcttct tatgcatgct    3540
atactgtttt tggcttgggg tctatacacc cccgcttcct catgttatag gtgatggtat    3600
agcttagcct ataggtgtgg gttattgacc attattgacc actccctat tggtgacgat     3660
actttccatt actaatccat aacatggctc tttgccacaa ctctctttat tggctatatg    3720
ccaatacact gtccttcaga gactgacacg gactctgtat ttttacagga tggggtctca    3780
tttattattt acaaattcac atatacaaca ccaccgtccc cagtgcccgc agtttttatt    3840
aaacataacg tgggatctcc acgcgaatct cgggtacgtg ttccggacat ggtctcttct    3900
ccggtagcgg cggagcttct catccgagcc cctgctccca tgcctccagc gactcatggt    3960
cgctcggcag ctccttgctc ctaacagtgg aggccagact taggcacagc acgatgccca    4020
ccaccaccag tgtgccgcac aaggccgtgg cggtagggta tgtgtctgaa aatgagctcg    4080
gggagcgggc ttgcaccgct gacgcatttg gaagacttaa ggcagcggca gaagaagatg    4140
caggcagctg agttgttgtg ttctgataag agtcagaggt aactcccgtt gcggtgctgt    4200
taacggtgga gggcagtgta gtctgagcag tactcgttgc tgccgcgcgc gccaccagac    4260
ataatagctg acagactaac agactgttcc tttccatggg tcttttctgc agtcaccgtc    4320
cttgacacga agcttatact cgagctctag attgggaacc cgggtctctc gaattcgaga    4380
tctccaccat gcacagacct agacgtcgtg gaactcgtcc acctccactg gcactgctcg    4440
ctgctctcct cctggctgca cgtggtgctg atgcacaagt acaactgcaa caaagcggag    4500
ctgaactggc caaccaggc gcttccgtga agatgtcttg taaagccagc gggtatacat      4560
ttactaatta ctggattcac tgggagaagc aaagacctga cagggattg gaatggattg     4620
gatacattaa tcctaacacc ggacacacag agtataatca aaaattcaag gataaggcca    4680
ccctcacagc cgacagatct tcttcaaccg cctatatgca actttcttcc ctcacttctg    4740
aagactccgc agtttacttt tgcgcacgaa cttattctgg aagctcccat ttcgactact    4800
ggggtcaagg aacaacactg atcgtgtcta gcggcggcgg agggtccggc gggggcggta    4860
gcggtggcgg aggttctgat attgtcatga ctcaaacacc tgtctctctg cctgtttcac    4920
ttggagatca agctagcatt tcctgccgct ctagtcaatc tctcgtccac aacaacggcg    4980
atactttctt gcattggtat ctgcagaaac caggtcagtc acctaaactg cttatataca    5040
aagtctctaa tagattctca ggggtgccag atcgattcag tggttctggg tccggtacag    5100
attttacact caagatatcc agagtagaag cagaagatct gggcgtgtat ttctgcagtc    5160
aaacaacact tattcctcgt acttttggag gcggtacaaa actggagatc aagcgtggag    5220
gcggagggag tgttttgttt tatctggccg ttgggataat gtttctcgta aatacagtac    5280
tttgggtaac aataaggaag gaactgaaga gaaagaaaaa atgggatctg aaatatcat    5340
tggacagtgg acacgaaaaa aaagtcacat catcattgca agaagaccgg cacttggagg    5400
aggaactgaa atgtcaagag caaaagaag aacaactgca agaaggcgta catagaaaag     5460
aaccacaggg agcaacatag gcggccgcta atcagccata ccacatttgt agaggtttta    5520
cttgctttaa aaaacctccc acacctcccc ctgaacctga acataaaat gaatgcaatt     5580
gttgttgtta acttgtttat tgcagcttat aatggttaca aataaagcaa tagcatcaca    5640
aatttcacaa ataaagcatt ttttcactg cattctagtt gtggtttgtc caaactcatc     5700
```
aatgtatctt atcatgtcta ccggtataac ttcgtataat gtatactata cgaagttag    5759

<210> SEQ ID NO 23
<211> LENGTH: 7627
<212> TYPE: DNA
<213> ORGANISM: artificial sequence
<220> FEATURE:
<223> OTHER INFORMATION: synthetic

<400> SEQUENCE: 23

| | |
|---|---|
| aagcttatac tcgagctcta gattgggaac ccgggtctct cgaattcgag atctccacca | 60 |
| tgcacagacc tagacgtcgt ggaactcgtc cacctccact ggcactgctc gctgctctcc | 120 |
| tcctggctgc acgtggtgct gatgcacaag tacaactgca acaaagcgga gctgaactgg | 180 |
| ccaaaccagg cgcttccgtg aagatgtctt gtaaagccag cggtatacga tttactaatt | 240 |
| actggattca ctgggagaag caagacctga acagggatt ggaatggatt ggatacatta | 300 |
| atcctaacac cggacacaca gagtataatc aaaaattcaa ggataaggcc accctcacag | 360 |
| ccgacagatc ttcttcaacc gcctatatgc aactttcttc cctcacttct gaagactccg | 420 |
| cagtttactt ttgcgcacga acttattctg gaagctccca tttcgactac tggggtcaag | 480 |
| gaacaacact gatcgtgtct agcggcggcg gagggtccgg cggggcggt agcggtggcg | 540 |
| gaggttctga tattgtcatg actcaaacac ctgtctctct gcctgtttca cttggagatc | 600 |
| aagctagcat ttcctgccgc tctagtcaat ctctcgtcca caacaacggc gatactttct | 660 |
| tgcattggta tctgcagaaa ccaggtcagt cacctaaact gcttatatac aaagtctcta | 720 |
| atagattctc aggggtgcca gatcgattca gtggttctgg gtccggtaca gattttacac | 780 |
| tcaagatatc cagagtagaa gcagaagatc tgggcgtgta tttctgcagt caaacaacac | 840 |
| ttattcctcg tacttttgga ggcggtacaa aactggagat caagcgtgga ggcggaggga | 900 |
| gtgtttttgtt ttatctggcc gttgggataa tgtttctcgt aaatacagta ctttgggtaa | 960 |
| caataaggaa ggaactgaag agaaagaaaa aatgggatct ggaaatatca ttggacagtg | 1020 |
| gacacgaaaa aaagtcaca tcatcattgc aagaagaccg gcacttggag gaggaactga | 1080 |
| aatgtcaaga gcaaaagaa gaacaactgc aagaaggcgt acatagaaaa gaaccacagg | 1140 |
| gagcaacata ggcggccgct aatcagccat accacatttg tagaggtttt acttgcttta | 1200 |
| aaaaacctcc cacacctccc cctgaacctg aaacataaaa tgaatgcaat tgttgttgtt | 1260 |
| aacttgttta ttgcagctta taatggttac aaataaagca atagcatcac aaatttcaca | 1320 |
| aataaagcat ttttttcact gcattctagt tgtggtttgt ccaaactcat caatgtatct | 1380 |
| tatcatgtct accggtataa cttcgtataa tgtatactat acgaagttag ccggtagggc | 1440 |
| ccctctcttc atgtgagcaa aaggccagca aaaggccagg aaccgtaaaa aggccgcgtt | 1500 |
| gctggcgttt ttccataggc tccgcccccc tgacgagcat cacaaaaatc gacgctcaag | 1560 |
| tcagaggtgg cgaaacccga caggactata aagataccag gcgtttcccc ctggaagctc | 1620 |
| cctcgtgcgc tctcctgttc cgaccctgcc gcttaccgga tacctgtccg cctttctccc | 1680 |
| ttcgggaagc gtggcgcttt ctcatagctc acgctgtagg tatctcagtt cggtgtaggt | 1740 |
| cgttcgctcc aagctgggct gtgtgcacga accccccgtt cagcccgacc gctgcgcctt | 1800 |
| atccggtaac tatcgtcttg agtccaaccc ggtaagacac gacttatcgc cactggcagc | 1860 |
| agccactggt aacaggatta gcagagcgag gtatgtaggc ggtgctacag agttcttgaa | 1920 |
| gtggtggcct aactacggct acactagaag aacagtattt ggtatctgcg ctctgctgaa | 1980 |
| gccagttacc ttcggaaaaa gagttggtag ctcttgatcc ggcaaacaaa ccaccgctgg | 2040 |

```
tagcggtggt ttttttgttt gcaagcagca gattacgcgc agaaaaaaag gatctcaaga    2100
agatcctttg atcttttcta cggggtctga cgctcagtgg aacgaaaact cacgttaagg    2160
gattttggtc atgggcgcgc ctcatactcc tgcaggcatg agattatcaa aaaggatctt    2220
cacctagatc cttttaaatt aaaaatgaag ttttaaatca atctaaagta tatatgagta    2280
aacttggtct gacagttacc aatgcttaat cagtgaggca cctatctcag cgatctgtct    2340
atttcgttca tccatagttg cctgactccc cgtcgtgtag ataactacga tacgggaggg    2400
cttaccatct ggccccagtg ctgcaatgat accgcgagac ccacgctcac cggctccaga    2460
tttatcagca ataaaccagc cagccggaag ggccgagcgc agaagtggtc ctgcaacttt    2520
atccgcctcc atccagtcta ttaattgttg ccgggaagct agagtaagta gttcgccagt    2580
taatagtttg cgcaacgttg ttgccattgc tacaggcatc gtggtgtcac gctcgtcgtt    2640
tggtatggct tcattcagct ccggttccca acgatcaagg cgagttacat gatccccat     2700 gttgtgcaaa aaagcggtta gctccttcgg tcctccgatc gttgtcagaa gtaagttggc    2760
cgcagtgtta tcactcatgg ttatggcagc actgcataat tctcttactg tcatgccatc    2820
cgtaagatgc ttttctgtga ctggtgagta ctcaaccaag tcattctgag aatagtgtat    2880
gcggcgaccg agttgctctt gcccggcgtc aatacgggat aatactgcgc cacatagcag    2940
aactttaaaa gtgctcatca ttggaaaacg ttcttcgggg cgaaaactct caaggatctt    3000
accgctgttg agatccagtt cgatgtaacc cactcgtgca cccaactgat cttcagcatc    3060
ttttactttc accagcgttt ctgggtgagc aaaaacagga aggcaaaatg ccgcaaaaaa    3120
gggaataagg gcgacacgga aatgttgaat actcatactc ttcctttttc aatattattg    3180
aagcatttat cagggttatt gtctcatgag cggatacata tttgaatgta tttagaaaaa    3240
taaacaaata ggggttccgc gcacatttcc ccgaaaagtg ccacctgacg tcaggtacac    3300
aacttcgtat agcatacatt atacgaagtt atggtaccaa gcctaggcct ccaaaaaagc    3360
ctcctcacta cttctggaat agctcagagg cagaggcggc ctcggcctct gcataaataa    3420
aaaaaattag tcagccatgg ggcggagaat gggcggaact gggcggagtt agggcggga    3480 tgggcggagt taggggcggg actatggttg ctgactaatt gagatgcatg ctttgcatac    3540
ttctgcctgc tggggagcct ggggactttc cacacctggt tgctgactaa ttgagatgca    3600
tgctttgcat acttctgcct gctggggagc tggggactt tccacaccgg atccaccatg    3660
ggttcagcta ttgagcagga tgggttgcat gctggtagtc ccgccgcatg ggtcgaacga    3720
ctgtttggat acgattgggc ccaacagact ataggctgtt ccgacgctgc tgtctttcgt    3780
ctttctgcac aaggtcgtcc agttctgttc gtgaaaaccg acttgtccgg agccctcaat    3840
gagttgcaag acgaagctgc acgactgagt tggcttgcca ccactggtgt cccatgtgcc    3900
gcagtacttg acgtcgtcac agaggctggt cgcgattggt tgctccttgg agaagtgccc    3960
ggccaagatc ttctcagttc ccaccttgcc cctgccgaaa aagtttcaat aatggctgac    4020
gctatgagaa ggctgcacac ccttgaccct gccacatgtc cattcgatca ccaagccaaa    4080
caccgaattg aacagctag aacccgcatg gaagccggcc tcgttgatca agacgatttg    4140
gatgaggaac accagggtct cgcacccgct gaactcttcg ctcgcctcaa agcacgaatg    4200
ccagacggag atgacttggt cgtaacccac ggagatgcct gccttcctaa cataatggta    4260
gagaatggaa gatttagcgg cttcattgat tgtggacgac ttggagttgc agatcggtac    4320
caagatatcg ctctcgctac cagagatatt gctgaagaat tgggcggaga atgggctgat    4380
```

```
cggtttctcg tactctacgg aattgccgca cctgattccc aacgcattgc ttttttaccgt    4440 cttctggatg agttcttcta aacgcgtccc ccctctccct ccccccccccc taacgttact    4500 ggccgaagcc gcttggaata aggccggtgt gcgtttgtct atatgttatt ttccaccata    4560
ttgccgtctt ttggcaatgt gagggcccgg aaacctggcc ctgtcttctt gacgagcatt    4620 cctagggggtc tttcccctct cgccaaagga atgcaaggtc tgttgaatgt cgtgaaggaa    4680
gcagttcctc tggaagcttc ttgaagacaa acaacgtctg tagcgaccct ttgcaggcag    4740
cggaaccccc cacctggcga caggtgcctc tgcggccaaa agccacgtgt ataagataca    4800
cctgcaaagg cggcacaacc ccagtgccac gttgtgagtt ggatagttgt ggaaagagtc    4860
aaatggctct cctcaagcgt attcaacaag gggctgaagg atgcccagaa ggtaccccat    4920
tgtatgggat ctgatctggg gcctcggtgc acatgcttta catgtgttta gtcgaggtta    4980
aaaaacgtct aggccccccg aaccacgggg acgtggtttt cctttgaaaa acacgattgc    5040
tcgaatcacc atggtgagca agggcgagga gctgttcacc ggggtggtgc ccatcctggt    5100
cgagctggac ggcgacgtaa acggccacaa gttcagcgtg tccggcgagg gcgagggcga    5160
tgccacctac ggcaagctga ccctgaagtt catctgcacc accggcaagc tgcccgtgcc    5220
ctggcccacc ctcgtgacca ccttcggcta cggcctgcag tgcttcgccc gctaccccga    5280
ccacatgaag cagcacgact tcttcaagtc cgccatgccc gaaggctacg tccaggagcg    5340
caccatcttc ttcaaggacg acggcaacta caagacccgc gccgaggtga agttcgaggg    5400
cgacaccctg gtgaaccgca tcgagctgaa gggcatcgac ttcaaggagg acggcaacat    5460
cctggggcac aagctggagt acaactacaa cagccacaac gtctatatca tggccgacaa    5520
gcagaagaac ggcatcaagg tgaacttcaa gatccgccac aacatcgagg acggcagcgt    5580
gcagctcgcc gaccactacc agcagaacac ccccatcggc gacggccccg tgctgctgcc    5640
cgacaaccac tacctgagct accagtccgc cctgagcaaa gaccccaacg agaagcgcga    5700
tcacatggtc ctgctggagt tcgtgaccgc cgccgggatc actctcggca tggacgagct    5760
gtacaagtaa tcggccgcta atcagccata ccacatttgt agaggtttta cttgctttaa    5820
aaaacctccc acacctcccc ctgaacctga aacataaaat gaatgcaatt gttgttgtta    5880
acttgtttat tgcagcttat aatggttaca aataaagcaa tagcatcaca aatttcacaa    5940
ataaagcatt ttttcactg cattctagtt gtggtttgtc caaactcatc aatgtatctt    6000
atcatgtcgg cgcgttgaca ttgattattg actagttatt aatagtaatc aattacgggg    6060
tcattagttc atagcccata tatggagttc cgcgttacat aacttacggt aaatggcccg    6120
cctggctgac cgcccaacga cccccgccca ttgacgtcaa taatgacgta tgttcccata    6180
gtaacgccaa tagggacttt ccattgacgt caatgggtgg agtatttacg gtaaactgcc    6240
cacttggcag tacatcaagt gtatcatatg ccaagtacgc cccctattga cgtcaatgac    6300
ggtaaatggc ccgcctggca ttatgcccag tacatgacct tatgggactt tcctacttgg    6360
cagtacatct acgtattagt catcgctatt accatggtga tgcggttttg gcagtacatc    6420
aatgggcgtg atagcggtt tgactcacgg ggatttccaa gtctccaccc cattgacgtc    6480
aatgggagtt gtttttggca ccaaaatcaa cgggactttc caaaatgtcg taacaactcc    6540
gccccattga cgcaaatggg cggtaggcgt gtacggtggg aggtctatat aagcagagct    6600
ctccctatca gtgatagaga tctccctatc agtgatagag atcgtcgacg tttagtgaac    6660
cgtcagatcg cctggagacg ccatccacgc tgttttgacc tccatagaag acaccgggac    6720
cgatccagcc tccgcggccg ggaacggtgc attggaacgc ggattccccg tgccaagagt    6780
```

-continued

```
gacgtaagta ccgcctatag agtctatagg cccacccct tggcttctta tgcatgctat      6840 actgttttg gcttgggtc tatacacccc cgcttcctca tgttataggt gatggtatag       6900
cttagcctat aggtgtgggt tattgaccat tattgaccac tcccctattg gtgacgatac     6960
tttccattac taatccataa catggctctt tgccacaact ctctttattg gctatatgcc    7020
aatacactgt ccttcagaga ctgacacgga ctctgtattt ttacaggatg gggtctcatt    7080
tattatttac aaattcacat atacaacacc accgtcccca gtgcccgcag tttttattaa    7140
acataacgtg ggatctccac gcgaatctcg ggtacgtgtt ccggacatgg tctcttctcc    7200
ggtagcggcg gagcttctac atccgagccc tgctcccatg cctccagcga ctcatggtcg    7260
ctcggcagct ccttgctcct aacagtggag gccagactta ggcacagcac gatgcccacc    7320
accaccagtg tgccgcacaa ggccgtggcg gtagggtatg tgtctgaaaa tgagctcggg    7380
gagcgggctt gcaccgctga cgcatttgga agacttaagg cagcggcaga agaagatgca    7440
ggcagctgag ttgttgtgtt ctgataagag tcagaggtaa ctcccgttgc ggtgctgtta    7500
acggtggagg gcagtgtagt ctgagcagta ctcgttgctg ccgcgcgcgc caccagacat    7560
aatagctgac agactaacag actgttcctt tccatgggtc ttttctgcag tcaccgtcct    7620
tgacacg                                                              7627
```

<210> SEQ ID NO 24
<211> LENGTH: 2669
<212> TYPE: DNA
<213> ORGANISM: artificial sequence
<220> FEATURE:
<223> OTHER INFORMATION: synthetic

<400> SEQUENCE: 24

```
agcctaggcc tccaaaaaag cctcctcact acttctggaa tagctcagag gcagaggcgg     60
cctcggcctc tgcataaata aaaaaaatta gtcagccatg gggcgagaa tgggcggaac     120 tgggcggagt taggggcggg atgggcggag ttaggggcgg gactatggtt gctgactaat    180
tgagatgcat gctttgcata cttctgcctg ctggggagcc tggggacttt ccacacctgg    240
ttgctgacta attgagatgc atgctttgca tacttctgcc tgctggggag cctggggact    300
ttccacaccg gatccaccat gggttcagct attgagcagg atgggttgca tgctggtagt    360
cccgccgcat gggtcgaacg actgtttgga tacgattggg cccaacagac tataggctgt    420
tccgacgctg ctgtctttcg tctttctgca caaggtcgtc cagttctgtt cgtgaaaacc    480
gacttgtccg gagccctcaa tgagttcaa gacgaagctg cacgactgag ttggcttgcc    540
accactggtg tcccatgtgc cgcagtactt gacgtcgtca cagaggctgg tcgcgattgg    600
ttgctccttg gagaagtgcc cggccaagat cttctcagtt cccaccttgc ccctgccgaa    660
aaagtttcaa taatggctga cgctatgaga aggctgcaca cccttgaccc tgccacatgt    720
ccattcgatc accaagccaa acaccgaatt gaacagagcta gaacccgcat ggaagccggc    780
ctcgttgatc aagacgattt ggatgaggaa caccagggtc tcgcacccgc tgaactcttc    840
gctcgcctca aagcacgaat gccagacgga gatgacttgg tcgtaaccca cggagatgcc    900
tgccttccta acataatggt agagaatgga agatttagcg gcttcattga ttgtggacga    960
cttggagttg cagatcggta ccaagatatc gctctcgcta ccagagatat tgctgaagaa   1020
ttgggcggag aatgggctga tcggtttctc gtactctacg gaattgccgc acctgattcc   1080
caacgcattg cttttttaccg tcttctggat gagttcttct aaacgcgtcc ccctctccc    1140
```

```
tccccccccc ctaacgttac tggccgaagc cgcttggaat aaggccggtg tgcgtttgtc      1200
tatatgttat tttccaccat attgccgtct tttggcaatg tgaggcccg gaaacctggc       1260 cctgtcttct tgacgagcat tcctaggggt cttccccctc tcgccaaagg aatgcaaggt     1320
ctgttgaatg tcgtgaagga agcagttcct ctggaagctt cttgaagaca acaacgtct      1380 gtagcgaccc tttgcaggca gcggaacccc ccacctggcg acaggtgcct ctgcggccaa     1440
aagccacgtg tataagatac acctgcaaag gcggcacaac cccagtgcca cgttgtgagt    1500
tggatagttg tggaaagagt caaatggctc tcctcaagcg tattcaacaa ggggctgaag     1560
gatgcccaga aggtaccccca ttgtatggga tctgatctgg ggcctcggtg cacatgcttt   1620
acatgtgttt agtcgaggtt aaaaaacgtc taggcccccc gaaccacggg acgtggttt      1680 tcctttgaaa acacgattg ctcgaatcac catggtgagc aagggcgagg agctgttcac      1740
cggggtggtg cccatcctgg tcgagctgga cggcgacgta acggccaca agttcagcgt     1800 gtccggcgag ggcgagggcg atgccaccta cggcaagctg accctgaagt tcatctgcac   1860
caccggcaag ctgcccgtgc cctggcccac cctcgtgacc accttcggct acggcctgca   1920
gtgcttcgcc cgctacccg accacatgaa gcagcacgac ttcttcaagt ccgccatgcc    1980
cgaaggctac gtccaggagc gcaccatctt cttcaaggac gacggcaact acaagacccg  2040
cgccgaggtg aagttcgagg gcgacaccct ggtgaaccgc atcgagctga agggcatcga  2100
cttcaaggag gacggcaaca tcctggggca agctggagt acaactaca cagccacaa      2160 cgtctatatc atggccgaca gcagaagaa cggcatcaag gtgaacttca agatccgcca   2220
caacatcgag gacggcagcg tgcagctcgc cgaccactac cagcagaaca cccccatcgg  2280
cgacggcccc gtgctgctgc ccgacaacca ctacctgagc taccagtccg ccctgagcaa  2340
agaccccaac gagaagcgcg atcacatggt cctgctggag ttcgtgaccg ccgccgggat  2400
cactctcggc atggacgagc tgtacaagta atcggccgct aatcagccat accacatttg  2460
tagaggtttt acttgcttta aaaaacctcc cacacctccc cctgaacctg aaacataaaa   2520
tgaatgcaat tgttgttgtt aacttgttta ttgcagctta taatggttac aaataaagca   2580
atagcatcac aaatttcaca ataaagcat ttttttcact gcattctagt tgtggtttgt      2640
ccaaactcat caatgtatct tatcatgtc                                       2669

<210> SEQ ID NO 25
<211> LENGTH: 3003
<212> TYPE: DNA
<213> ORGANISM: artificial sequence
<220> FEATURE:
<223> OTHER INFORMATION: synthetic

<400> SEQUENCE: 25
gttgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggagt atttacggta aactgcccac ttggcagtac     240
atcaagtgta tcatatgcca agtacgcccc ctattgacgt caatgacggt aaatggcccg     300
cctggcatta tgcccagtac atgaccttat gggactttcc tacttggcag tacatctacg     360
tattagtcat cgctattacc atggtgatgc ggttttggca gtacatcaat gggcgtggat     420
agcggtttga ctcacgggga tttccaagtc tccaccccat tgacgtcaat gggagtttgt     480
tttggcacca aaatcaacgg gactttccaa aatgtcgtaa caactccgcc ccattgacgc     540
```

```
aaatgggcgg taggcgtgta cggtgggagg tctatataag cagagctctc cctatcagtg    600
atagagatct ccctatcagt gatagagatc gtcgacgttt agtgaaccgt cagatcgcct    660
ggagacgcca tccacgctgt tttgacctcc atagaagaca ccgggaccga tccagcctcc    720
gcggccggga acggtgcatt ggaacgcgga ttccccgtgc caagagtgac gtaagtaccg    780
cctatagagt ctataggccc accccttgg cttcttatgc atgctatact gtttttggct    840
tggggtctat acaccccgc ttcctcatgt tataggtgat ggtatagctt agcctatagg    900
tgtgggttat tgaccattat tgaccactcc cctattggtg acgatacttt ccattactaa    960
tccataacat ggctctttgc cacaactctc tttattggct atatgccaat acactgtcct   1020
tcagagactg acacggactc tgtatttta caggatgggg tctcatttat tatttacaaa   1080
ttcacatata caacaccacc gtccccagtg cccgcagttt ttattaaaca taacgtggga   1140
tctccacgcg aatctcgggt acgtgttccg gacatggtct cttctccggt agcggcggag   1200
cttctacatc cgagccctgc tcccatgcct ccagcgactc atggtcgctc ggcagctcct   1260
tgctcctaac agtggaggcc agacttaggc acagcacgat gcccaccacc accagtgtgc   1320
cgcacaaggc cgtggcggta gggtatgtgt ctgaaaatga gctcggggag cgggcttgca   1380
ccgctgacgc atttggaaga cttaaggcag cggcagaaga agatgcaggc agctgagttg   1440
ttgtgttctg ataagagtca gaggtaactc ccgttgcggt gctgttaacg gtggagggca   1500
gtgtagtctg agcagtactc gttgctgccg cgcgcgccac cagacataat agctgacaga   1560
ctaacagact gttcctttcc atgggtcttt tctgcagtca ccgtccttga cacgaagctt   1620
atactcgagc tctagattgg gaacccgggt ctctcgaatt cgagatctcc accatgcaca   1680
gacctagacg tcgtggaact cgtccacctc cactggcact gctcgctgct ctcctcctgg   1740
ctgcacgtgg tgctgatgca caagtacaac tgcaacaaag cggagctgaa ctggccaaac   1800
caggcgcttc cgtgaagatg tcttgtaaag ccagcgggta tacatttact aattactgga   1860
ttcactggga gaagcaaaga cctgaacagg gattggaatg gattggatac attaatccta   1920
acaccggaca cacagagtat aatcaaaaat tcaaggataa ggccaccctc acagccgaca   1980
gatcttcttc aaccgcctat atgcaacttt cttccctcac ttctgaagac tccgcagttt   2040
actttgcgc acgaacttat tctgaagct cccatttcga ctactggggt caaggaacaa   2100
cactgatcgt gtctagcggc ggcggagggt ccggcggggg cggtagcggt ggcggaggtt   2160
ctgatattgt catgactcaa acacctgtct ctctgcctgt ttcacttgga gatcaagcta   2220
gcatttcctg ccgctctagt caatctctcg tccacaacaa cggcgatact ttcttgcatt   2280
ggtatctgca gaaaccaggt cagtcaccta aactgcttat atacaaagtc tctaatagat   2340
tctcaggggt gccagatcga ttcagtggtt ctgggtccgg tacagatttt acactcaaga   2400
tatccagagt agaagcagaa gatctgggcg tgtatttctg cagtcaaaca acacttattc   2460
ctcgtacttt tggaggcgt acaaaactgg agatcaagcg tggaggcgga gggagtgttt   2520
tgttttatct ggccgttggg ataatgtttc tcgtaaatac agtactttgg gtaacaataa   2580
ggaaggaact gaagagaaag aaaaaatggg atctggaaat atcattggac agtggacacg   2640
aaaaaaagt cacatcatca ttgcaagaag accggcactt ggaggaggaa ctgaaatgtc   2700
aagagcaaaa agaagaacaa ctgcaagaag cgtacatag aaaagaacca cagggagcaa   2760
cataggcggc cgctaatcag ccataccaca tttgtagagg ttttacttgc tttaaaaaac   2820
ctcccacacc tccccctgaa cctgaaacat aaaatgaatg caattgttgt tgttaacttg   2880
```

```
tttattgcag cttataatgg ttacaaataa agcaatagca tcacaaattt cacaaataaa   2940
gcattttttt cactgcattc tagttgtggt ttgtccaaac tcatcaatgt atcttatcat   3000
gtc                                                                3003
```

<210> SEQ ID NO 26
<211> LENGTH: 208
<212> TYPE: PRT
<213> ORGANISM: Homo sapiens

<400> SEQUENCE: 26

```
Val Phe Leu Phe Pro Pro Lys Pro Lys Asp Thr Leu Met Ile Ser Arg
1               5                   10                  15

Thr Pro Glu Val Thr Cys Val Val Asp Val Ser Gln Glu Asp Pro
            20                  25                  30

Glu Val Gln Phe Asn Trp Tyr Val Asp Gly Val Glu Val His Asn Ala
        35                  40                  45

Lys Thr Lys Pro Arg Glu Glu Gln Phe Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Gly Leu Pro Ser Ser Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Gln Glu Glu Met Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Arg Leu Thr Val Asp Lys Ser
                165                 170                 175

Arg Trp Gln Glu Gly Asn Val Phe Ser Cys Ser Val Met His Glu Ala
            180                 185                 190

Leu His Asn His Tyr Thr Gln Lys Ser Leu Ser Leu Ser Leu Gly Lys
        195                 200                 205
```

<210> SEQ ID NO 27
<211> LENGTH: 8
<212> TYPE: PRT
<213> ORGANISM: Homo sapiens

<400> SEQUENCE: 27

```
Gly Tyr Thr Phe Thr Asn Tyr Trp
1               5
```

<210> SEQ ID NO 28
<211> LENGTH: 8
<212> TYPE: PRT
<213> ORGANISM: Homo sapiens

<400> SEQUENCE: 28

```
Ile Asn Pro Asn Thr Gly His Thr
1               5
```

<210> SEQ ID NO 29
<211> LENGTH: 13
<212> TYPE: PRT

<213> ORGANISM: Homo sapiens

<400> SEQUENCE: 29

Cys Ala Arg Thr Tyr Ser Gly Ser Ser His Phe Asp Tyr
1               5                   10

<210> SEQ ID NO 30
<211> LENGTH: 10
<212> TYPE: PRT
<213> ORGANISM: Homo sapiens

<400> SEQUENCE: 30

Ser Leu Val His Asn Asn Gly Asp Thr Phe
1               5                   10

<210> SEQ ID NO 31
<211> LENGTH: 9
<212> TYPE: PRT
<213> ORGANISM: Homo sapiens

<400> SEQUENCE: 31

Ser Gln Thr Thr Leu Ile Pro Arg Thr
1               5

<210> SEQ ID NO 32
<211> LENGTH: 8
<212> TYPE: PRT
<213> ORGANISM: Homo sapiens

<400> SEQUENCE: 32

Gly Phe Thr Phe Ser Asn Ala Trp
1               5

<210> SEQ ID NO 33
<211> LENGTH: 10
<212> TYPE: PRT
<213> ORGANISM: Homo sapiens

<400> SEQUENCE: 33

Ile Leu Ser Lys Thr Asp Gly Gly Thr Thr
1               5                   10

<210> SEQ ID NO 34
<211> LENGTH: 13
<212> TYPE: PRT
<213> ORGANISM: Homo sapiens

<400> SEQUENCE: 34

Thr Thr Ala Asp Phe Trp Ser Ala Tyr Ser Ser Asp Tyr
1               5                   10

<210> SEQ ID NO 35
<211> LENGTH: 4
<212> TYPE: PRT
<213> ORGANISM: Homo sapiens

<400> SEQUENCE: 35

Gln Ser Leu Leu
1

<210> SEQ ID NO 36
<211> LENGTH: 7
<212> TYPE: PRT
<213> ORGANISM: Homo sapiens

```
<400> SEQUENCE: 36

His Ser Asn Gly Tyr Asn Tyr
1               5

<210> SEQ ID NO 37
<211> LENGTH: 9
<212> TYPE: PRT
<213> ORGANISM: Homo sapiens

<400> SEQUENCE: 37

Met Gln Gly Leu Gln Thr Pro Tyr Thr
1               5

<210> SEQ ID NO 38
<211> LENGTH: 122
<212> TYPE: PRT
<213> ORGANISM: Homo sapiens

<400> SEQUENCE: 38

Glu Val Gln Leu Val Glu Ser Gly Gly Ala Ile Val Lys Pro Gly Gly
1               5                   10                  15

Ser His Arg Val Ser Cys Glu Ala Ser Gly Phe Thr Phe Ser Asn Ala
                20                  25                  30

Trp Met Ser Trp Val Arg Gln Ala Pro Gly Arg Gly Leu Glu Trp Val
            35                  40                  45

Gly Arg Ile Leu Ser Lys Thr Asp Gly Gly Thr Thr Asp Tyr Ala Ala
        50                  55                  60

Pro Val Lys Asp Arg Phe Thr Ile Ser Arg Asp Ser Lys Asn Met
65                  70                  75                  80

Leu Phe Leu Gln Met Asp Ser Leu Lys Ile Glu Asp Thr Ala Val Tyr
                85                  90                  95

Phe Cys Thr Thr Ala Asp Phe Trp Ser Ala Tyr Ser Ser Asp Tyr Trp
            100                 105                 110

Gly Gln Gly Thr Leu Val Thr Val Ser Ser
        115                 120

<210> SEQ ID NO 39
<211> LENGTH: 112
<212> TYPE: PRT
<213> ORGANISM: Homo sapiens

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Met Glu Ala Glu Asp Val Gly Val Tyr Tyr Cys Met Gln Gly
                85                  90                  95

Leu Gln Thr Pro Tyr Thr Phe Gly Gln Gly Thr Lys Leu Glu Ile Lys
            100                 105                 110

<210> SEQ ID NO 40
```

```
<211> LENGTH: 452
<212> TYPE: PRT
<213> ORGANISM: Homo sapiens

<400> SEQUENCE: 40

Glu Val Gln Leu Val Glu Ser Gly Gly Ala Ile Val Lys Pro Gly Gly
 1               5                  10                  15

Ser His Arg Val Ser Cys Glu Ala Ser Gly Phe Thr Phe Ser Asn Ala
            20                  25                  30

Trp Met Ser Trp Val Arg Gln Ala Pro Gly Arg Gly Leu Glu Trp Val
        35                  40                  45

Gly Arg Ile Leu Ser Lys Thr Asp Gly Thr Thr Asp Tyr Ala Ala
    50                  55                  60

Pro Val Lys Asp Arg Phe Thr Ile Ser Arg Asp Asp Ser Lys Asn Met
65                  70                  75                  80

Leu Phe Leu Gln Met Asp Ser Leu Lys Ile Glu Asp Thr Ala Val Tyr
                85                  90                  95

Phe Cys Thr Thr Ala Asp Phe Trp Ser Ala Tyr Ser Ser Asp Tyr Trp
            100                 105                 110

Gly Gln Gly Thr Leu Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
```

```
                385                 390                 395                 400
        Pro Val Leu Asp Ser Asp Gly Ser Tyr Phe Met Tyr Ser Lys Leu Arg
                        405                 410                 415

Val Glu Lys Lys Asn Trp Val Glu Arg Asn Ser Tyr Ser Cys Ser Val
                        420                 425                 430

Val His Glu Gly Leu His Asn His Thr Thr Lys Ser Phe Ser Arg
                        435                 440                 445

Thr Pro Gly Lys
                450

<210> SEQ ID NO 41
<211> LENGTH: 219
<212> TYPE: PRT
<213> ORGANISM: Homo sapiens

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Met Glu Ala Glu Asp Val Gly Val Tyr Tyr Cys Met Gln Gly
                85                  90                  95

Leu Gln Thr Pro Tyr Thr Phe Gly Gln Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Gly Glu Cys
    210                 215

<210> SEQ ID NO 42
<211> LENGTH: 256
<212> TYPE: PRT
<213> ORGANISM: Homo sapiens

<400> SEQUENCE: 42

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Pro Gly Asp Lys Thr
            20                  25                  30

His Thr Cys Pro Pro Cys Pro Ala Pro Glu Leu Leu Gly Gly Pro Ser
```

```
            35                  40                  45
Val Phe Leu Phe Pro Pro Lys Pro Lys Asp Thr Leu Met Ile Ser Arg
 50                  55                  60

Thr Pro Glu Val Thr Cys Val Val Asp Val Ser His Glu Asp Pro
 65                  70                  75                  80

Glu Val Lys Phe Asn Trp Tyr Val Asp Gly Val Glu Val His Asn Ala
                 85                  90                  95

Lys Thr Lys Pro Arg Glu Glu Gln Tyr Asn Ser Thr Tyr Arg Val Val
                100                 105                 110

Ser Val Leu Thr Val Leu His Gln Asp Trp Leu Asn Gly Lys Glu Tyr
                115                 120                 125

Lys Cys Lys Val Ser Asn Lys Ala Leu Pro Ala Pro Ile Glu Lys Thr
130                 135                 140

Ile Ser Lys Ala Lys Gly Gln Pro Arg Glu Pro Gln Val Tyr Thr Leu
145                 150                 155                 160

Pro Pro Ser Arg Asp Glu Leu Thr Lys Asn Gln Val Ser Leu Thr Cys
                165                 170                 175

Leu Val Lys Gly Phe Tyr Pro Ser Asp Ile Ala Val Glu Trp Glu Ser
                180                 185                 190

Asn Gly Gln Pro Glu Asn Asn Tyr Lys Thr Thr Pro Pro Val Leu Asp
            195                 200                 205

Ser Asp Gly Ser Phe Phe Leu Tyr Ser Lys Leu Thr Val Asp Lys Ser
210                 215                 220

Arg Trp Gln Gln Gly Asn Val Phe Ser Cys Ser Val Met His Glu Ala
225                 230                 235                 240

Leu His Asn Arg Phe Thr Gln Lys Ser Leu Ser Leu Ser Pro Gly Lys
                245                 250                 255

<210> SEQ ID NO 43
<211> LENGTH: 336
<212> TYPE: PRT
<213> ORGANISM: Artificial sequence
<220> FEATURE:
<223> OTHER INFORMATION: synthetic

<400> SEQUENCE: 43

Glu Val Gln Leu Val Glu Ser Gly Gly Ala Ile Val Lys Pro Gly Gly
 1               5                  10                  15

Ser His Arg Val Ser Cys Glu Ala Ser Gly Phe Thr Phe Ser Asn Ala
                 20                  25                  30

Trp Met Ser Trp Val Arg Gln Ala Pro Gly Arg Gly Leu Glu Trp Val
             35                  40                  45

Gly Arg Ile Leu Ser Lys Thr Asp Gly Gly Thr Thr Asp Tyr Ala Ala
 50                  55                  60

Pro Val Lys Asp Arg Phe Thr Ile Ser Arg Asp Asp Ser Lys Asn Met
 65                  70                  75                  80

Leu Phe Leu Gln Met Asp Ser Leu Lys Ile Glu Asp Thr Ala Val Tyr
                 85                  90                  95

Phe Cys Thr Thr Ala Asp Phe Trp Ser Ala Tyr Ser Ser Asp Tyr Trp
                100                 105                 110

Gly Gln Gly Thr Leu Val Thr Val Ser Ser Gly Gly Gly Ser Gly
                115                 120                 125

Gly Gly Gly Ser Gly Gly Gly Ser Asp Ile Val Met Thr Gln Ser
            130                 135                 140

Pro Leu Ser Leu Pro Val Thr Pro Gly Glu Pro Ala Ser Ile Ser Cys
```

```
                145                 150                 155                 160
Arg Ser Ser Gln Ser Leu Leu His Ser Asn Gly Tyr Asn Tyr Leu Asp
                    165                 170                 175
Trp Tyr Leu Gln Lys Pro Gly Gln Ser Pro Gln Leu Leu Ile Tyr Leu
                    180                 185                 190
Gly Ser Asn Arg Ala Ser Gly Val Pro Asp Arg Phe Ser Gly Ser Gly
                    195                 200                 205
Ser Gly Thr Asp Phe Thr Leu Lys Ile Ser Arg Met Glu Ala Glu Asp
        210                 215                 220
Val Gly Val Tyr Tyr Cys Met Gln Gly Leu Gln Thr Pro Tyr Thr Phe
225                 230                 235                 240
Gly Gln Gly Thr Lys Leu Glu Ile Lys Gly Gly Gly Ser Val Leu
                    245                 250                 255
Phe Tyr Leu Ala Val Gly Ile Met Phe Leu Val Asn Thr Val Leu Trp
                    260                 265                 270
Val Thr Ile Arg Lys Glu Leu Lys Arg Lys Lys Lys Trp Asp Leu Glu
                    275                 280                 285
Ile Ser Leu Asp Ser Gly His Glu Lys Lys Val Thr Ser Ser Leu Gln
        290                 295                 300
Glu Asp Arg His Leu Glu Glu Glu Leu Lys Cys Gln Glu Gln Lys Glu
305                 310                 315                 320
Glu Gln Leu Gln Glu Gly Val His Arg Lys Glu Pro Gln Gly Ala Thr
                    325                 330                 335
```

<210> SEQ ID NO 44
<211> LENGTH: 7633
<212> TYPE: DNA
<213> ORGANISM: Artificial sequence
<220> FEATURE:
<223> OTHER INFORMATION: synthetic

<400> SEQUENCE: 44

```
aagcttatac tcgagctcta gattgggaac ccgggtctct cgaattcgag atctccacca      60
tgcacagacc tagacgtcgt ggaactcgtc cacctccact ggcactgctc gctgctctcc     120
tcctggctgc acgtggtgct gatgcagagg tgcagctggt ggagtctggg ggagccatag     180
taaagccggg ggggtcccat agagtctcct gtgaagcctc tggattcact ttcagtaacg     240
cctggatgag ttgggtccgc caggctccag gagggggct ggagtgggtt ggccgtattt     300
taagcaagac tgatggtggg acgacagact acgctgcacc cgtgaaagac agattcacca     360
tttcaagaga tgattctaaa aatatgttgt ttctgcaaat ggacagcctg aaaatcgagg     420
acacagccgt gtatttctgt accacggccg attttggag tgcttattct tctgactact     480
ggggccaggg aaccctggtc accgtctcct caggaggtgg aggttccggg ggcggggct     540
ccggcggagg tggatcagat attgtgatga ctcagtctcc actctccctg cccgtcaccc     600
ctggagagcc ggcctccatc tcctgcaggt ctagtcagag cctcctgcat agtaatgggt     660
acaactattt ggattggtac ctacagaagc agggcagtc tccacaactc ctgatctatt     720
tgggttctaa tcgggcctcc ggggtccctg acaggttcag tggcagtgga tcaggcacag     780
attttacact gaaaatcagc agaatggagg ctgaggatgt ggggtttat tactgcatgc     840
aaggtctaca aactccgtac acttttggcc aggggaccaa gctggagatc aaaggaggcg     900
gagggagtgt tttgttttat ctggccgttg ggataatgtt tctcgtaaat acagtacttt     960
gggtaacaat aaggaaggaa ctgaagagaa agaaaaaatg ggatctggaa atatcattgg    1020
```

```
acagtggaca cgaaaaaaaa gtcacatcat cattgcaaga agaccggcac ttggaggagg    1080
aactgaaatg tcaagagcaa aaagaagaac aactgcaaga aggcgtacat agaaaagaac    1140
cacagggagc aacataggcg gccgctaatc agccatacca catttgtaga ggttttactt    1200
gctttaaaaa acctcccaca cctcccctg aacctgaaac ataaaatgaa tgcaattgtt     1260
gttgttaact tgtttattgc agcttataat ggttacaaat aaagcaatag catcacaaat    1320
ttcacaaata aagcattttt ttcactgcat tctagttgtg gtttgtccaa actcatcaat    1380
gtatcttatc atgtctaccg gtataacttc gtataatgta tactatacga agttagccgg    1440
tagggcccct ctcttcatgt gagcaaaagg ccagcaaaag gccaggaacc gtaaaaaggc    1500
cgcgttgctg gcgttttcc ataggctccg ccccctgac gagcatcaca aaaatcgacg      1560
ctcaagtcag aggtggcgaa acccgacagg actataaaga taccaggcgt ttccccctgg    1620
aagctccctc gtgcgctctc ctgttccgac cctgccgctt accggatacc tgtccgcctt    1680
tctcccttcg ggaagcgtgg cgctttctca tagctcacgc tgtaggtatc tcagttcggt    1740
gtaggtcgtt cgctccaagc tgggctgtgt gcacgaaccc cccgttcagc ccgaccgctg    1800
cgccttatcc ggtaactatc gtcttgagtc caacccggta agacacgact tatcgccact    1860
ggcagcagcc actggtaaca ggattagcag agcgaggtat gtaggcggtg ctacagagtt    1920
cttgaagtgg tggcctaact acggctacac tagaagaaca gtatttggta tctgcgctct    1980
gctgaagcca gttaccttcg gaaaaagagt tggtagctct tgatccggca acaaaccac     2040 cgctggtagc ggtggttttt tgtttgcaa gcagcagatt acgcgcagaa aaaaggatc      2100 tcaagaagat cctttgatct tttctacggg gtctgacgct cagtggaacg aaaactcacg    2160
ttaagggatt ttggtcatgg gcgcgcctca tactcctgca ggcatgagat tatcaaaaag    2220
gatcttcacc tagatccttt taaattaaaa atgaagtttt aaatcaatct aaagtatata    2280
tgagtaaact tggtctgaca gttaccaatg cttaatcagt gaggcaccta tctcagcgat    2340
ctgtctattt cgttcatcca tagttgcctg actccccgtc gtgtagataa ctacgatacg    2400
ggagggctta ccatctggcc ccagtgctgc aatgataccg cgagacccac gctcaccggc    2460
tccagattta tcagcaataa accagccagc cggaagggcc gagcgcagaa gtggtcctgc    2520
aactttatcc gcctccatcc agtctattaa ttgttgccgg gaagctagag taagtagttc    2580
gccagttaat agtttgcgca acgttgttgc cattgctaca ggcatcgtgg tgtcacgctc    2640
gtcgtttggt atggcttcat tcagctccgg ttcccaacga tcaaggcgag ttacatgatc    2700
ccccatgttg tgcaaaaaag cggttagctc cttcggtcct ccgatcgttg tcagaagtaa    2760
gttggccgca gtgttatcac tcatggttat ggcagcactg cataattctc ttactgtcat    2820
gccatccgta agatgctttt ctgtgactgg tgagtactca accaagtcat tctgagaata    2880
gtgtatgcgg cgaccgagtt gctcttgccc ggcgtcaata cgggataata ctgcgccaca    2940
tagcagaact ttaaaagtgc tcatcattgg aaaacgttct cggggcgaa aactctcaag     3000 gatcttaccg ctgttgagat ccagttcgat gtaacccact cgtgcaccca actgatcttc    3060
agcatctttt actttcacca gcgtttctgg gtgagcaaaa acaggaaggc aaaatgccgc    3120
aaaaaaggga ataagggcga cacggaaatg ttgaatactc atactcttcc tttttcaata    3180
ttattgaagc atttatcagg gttattgtct catgagcgga tacatatttg aatgtattta    3240
gaaaaataaa caaatagggg ttccgcgcac atttccccga aaagtgccac ctgacgtcag    3300
gtacacaact tcgtatagca tacattatac gaagttatgg taccaagcct aggcctccaa    3360
aaaagcctcc tcactacttc tggaatagct cagaggcaga ggcggcctcg gcctctgcat    3420
```

```
aaataaaaaa aattagtcag ccatggggcg gagaatgggc ggaactgggc ggagttaggg    3480
gcgggatggg cggagttagg ggcgggacta tggttgctga ctaattgaga tgcatgcttt    3540
gcatacttct gcctgctggg gagcctgggg actttccaca cctggttgct gactaattga    3600
gatgcatgct ttgcatactt ctgcctgctg gggagcctgg ggactttcca caccggatcc    3660
accatgggtt cagctattga gcaggatggg ttgcatgctg gtagtcccgc cgcatgggtc    3720
gaacgactgt ttggatacga ttgggcccaa cagactatag gctgttccga cgctgctgtc    3780
tttcgtcttt ctgcacaagg tcgtccagtt ctgttcgtga aaaccgactt gtccggagcc    3840
ctcaatgagt tgcaagacga agctgcacga ctgagttggc ttgccaccac tggtgtccca    3900
tgtgccgcag tacttgacgt cgtcacagag gctggtcgcg attggttgct ccttggagaa    3960
gtgcccggcc aagatcttct cagttcccac cttgcccctg ccgaaaaagt ttcaataatg    4020
gctgacgcta tgagaaggct gcacaccctt gaccctgcca catgtccatt cgatcaccaa    4080
gccaaacacc gaattgaacg agctagaacc cgcatggaag ccggcctcgt tgatcaagac    4140
gatttggatg aggaacacca gggtctcgca cccgctgaac tcttcgctcg cctcaaagca    4200
cgaatgccag acgagatgac ttggtcgta acccacggag atgcctgcct tcctaacata    4260
atggtagaga atggaagatt tagcggcttc attgattgtg gacgacttgg agttgcagat    4320
cggtaccaag atatcgctct cgctaccaga gatattgctg aagaattggg cggagaatgg    4380
gctgatcggt ttctcgtact ctacggaatt gccgcacctg attcccaacg cattgctttt    4440
taccgtcttc tggatgagtt cttctaaacg cgtccccct ctcctcccc cccccctaac      4500 gttactggcc gaagccgctt ggaataaggc cggtgtgcgt ttgtctatat gttattttcc    4560
accatattgc cgtcttttgg caatgtgagg gcccggaaac ctggccctgt cttcttgacg    4620
agcattccta ggggtctttc ccctctcgcc aaaggaatgc aaggtctgtt gaatgtcgtg    4680
aaggaagcag ttcctctgga agcttcttga agacaaacaa cgtctgtagc gaccctttgc    4740
aggcagcgga acccccacc tggcgacagg tgcctctgcg gccaaaagcc acgtgtataa     4800
gatacacctg caaaggcggc acaacccag tgccacgttg tgagttggat agttgtggaa     4860
agagtcaaat ggctctcctc aagcgtattc aacaagggc tgaaggatgc ccagaaggta     4920
ccccattgta tgggatctga tctggggcct cggtgcacat gctttacatg tgtttagtcg    4980
aggttaaaaa acgtctaggc cccccgaacc acggggacgg ggttttcctt tgaaaaacac    5040
gattgctcga atcaccatgg tgagcaaggg cgaggagctg ttcaccgggg tggtgcccat    5100
cctggtcgag ctggacggcg acgtaaacgg ccacaagttc agcgtgtccg gcgagggcga    5160
gggcgatgcc acctacggca agctgaccct gaagttcatc tgcaccaccg gcaagctgcc    5220
cgtgccctgg cccaccctcg tgaccacctt cggctacggc ctgcagtgct tcgcccgcta    5280
ccccgaccac atgaagcagc acgacttctt caagtccgcc atgcccgaag gctacgtcca    5340
ggagcgcacc atcttcttca aggacgacgg caactacaag acccgcgccg aggtgaagtt    5400
cgagggcgac accctggtga accgcatcga gctgaagggc atcgacttca aggaggacgg    5460
caacatcctg gggcacaagc tggagtacaa ctacaacagc cacaacgtct atatcatggc    5520
cgacaagcag aagaacggca tcaaggtgaa cttcaagatc cgccacaaca tcgaggacgg    5580
cagcgtgcag ctcgccgacc actaccagca gaacaccccc atcggcgacg gccccgtgct    5640
gctgcccgac aaccactacc tgagctacca gtccgccctg agcaaagacc ccaacgagaa    5700
gcgcgatcac atggtcctgc tggagttcgt gaccgccgcc gggatcactc tcggcatgga    5760
```

```
cgagctgtac aagtaatcgg ccgctaatca gccataccac atttgtagag gttttacttg    5820
ctttaaaaaa cctcccacac ctccccctga acctgaaaca taaatgaat gcaattgttg     5880
ttgttaactt gtttattgca gcttataatg gttacaaata aagcaatagc atcacaaatt    5940
tcacaaataa agcattttt tcactgcatt ctagttgtgg tttgtccaaa ctcatcaatg     6000
tatcttatca tgtcggcgcg ttgacattga ttattgacta gttattaata gtaatcaatt    6060
acggggtcat tagttcatag cccatatatg gagttccgcg ttacataact tacggtaaat    6120
ggcccgcctg gctgaccgcc caacgacccc cgcccattga cgtcaataat gacgtatgtt    6180
cccatagtaa cgccaatagg gactttccat tgacgtcaat gggtggagta tttacgtaa     6240
actgcccact tggcagtaca tcaagtgtat catatgccaa gtacgccccc tattgacgtc    6300
aatgacggta aatggcccgc ctggcattat gcccagtaca tgaccttatg gactttcct     6360
acttggcagt acatctacgt attagtcatc gctattacca tggtgatgcg gttttggcag    6420
tacatcaatg ggcgtggata gcggtttgac tcacggggat ttccaagtct ccaccccatt    6480
gacgtcaatg ggagtttgtt ttggcaccaa aatcaacggg actttccaaa atgtcgtaac    6540
aactccgccc cattgacgca aatgggcggt aggcgtgtac ggtgggaggt ctatataagc    6600
agagctctcc ctatcagtga tagagatctc cctatcagtg atagagatcg tcgacgttta    6660
gtgaaccgtc agatcgcctg gagacgccat ccacgctgtt tgacctccag tagaagacac    6720
cgggaccgat ccagcctccg cggccgggaa cggtgcattg gaacgcggat tccccgtgcc    6780
aagagtgacg taagtaccgc ctatagagtc tataggccca ccccttggc ttcttatgca     6840
tgctatactg ttttttggctt ggggtctata cacccccgct tcctcatgtt ataggtgatg   6900
gtatagctta gcctataggt gtgggttatt gaccattatt gaccactccc ctattggtga    6960
cgatactttc cattactaat ccataacatg gctctttgcc acaactctct ttattggcta    7020
tatgccaata cactgtcctt cagagactga cacggactct gtatttttac aggatggggt    7080
ctcatttatt atttacaaat tcacatatac aacaccaccg tccccagtgc cgcagttt     7140
tattaaacat aacgtgggat ctccacgcga atctcggta cgtgttccgg acatggtctc    7200
ttctccggta gcggcggagc ttctacatcc gagccctgct cccatgcctc cagcgactca    7260
tggtcgctcg gcagctcctt gctcctaaca gtggaggcca gacttaggca cagcacgatg    7320
cccaccacca ccagtgtgcc gcacaaggcc gtggcggtag ggtatgtgtc tgaaaatgag    7380
ctcggggagc gggcttgcac cgctgacgca tttggaagac ttaaggcagc ggcagaagaa    7440
gatgcaggca gctgagttgt tgtgttctga taagagtcag aggtaactcc cgttgcggtg    7500
ctgttaacgg tggagggcag tgtagtctga gcagtactcg ttgctgccgc gcgcgccacc    7560
agacataata gctgacagac taacagactg ttcctttcca tgggtctttt ctgcagtcac    7620
cgtccttgac acg                                                        7633
```

<210> SEQ ID NO 45
<211> LENGTH: 1011
<212> TYPE: DNA
<213> ORGANISM: Artificial sequence
<220> FEATURE:
<223> OTHER INFORMATION: synthetic

<400> SEQUENCE: 45

```
gaggtgcagc tggtggagtc tgggggagcc atagtaaagc cggggggtc ccatagagtc      60
tcctgtgaag cctctggatt cactttcagt aacgcctgga tgagttgggt ccgccaggct    120
ccagggaggg gctggagtg ggttggccgt attttaagca agactgatgg tgggacgaca    180
```

```
gactacgctg cacccgtgaa agacagattc accatttcaa gagatgattc taaaaatatg      240
ttgtttctgc aaatggacag cctgaaaatc gaggacacag ccgtgtattt ctgtaccacg      300
gccgattttt ggagtgctta ttcttctgac tactggggcc agggaaccct ggtcaccgtc      360
tcctcaggag gtggaggttc cggggggcggg ggctccggcg gaggtggatc agatattgtg      420
atgactcagt ctccactctc cctgcccgtc acccctggag agccggcctc catctcctgc      480
aggtctagtc agagcctcct gcatagtaat gggtacaact atttggattg gtacctacag      540
aagccagggc agtctccaca actcctgatc tatttgggtt ctaatcgggc ctccggggtc      600
cctgacaggt tcagtggcag tggatcaggc acagatttta cactgaaaat cagcagaatg      660
gaggctgagg atgttggggt ttattactgc atgcaaggtc tacaaactcc gtacactttt      720
ggccagggga ccaagctgga gatcaaagga ggcggaggga gtgttttgtt ttatctggcc      780
gttgggataa tgtttctcgt aaatacagta ctttgggtaa cataaggaa ggaactgaag       840 agaaagaaaa aatgggatct ggaaatatca ttggacagtg gacacgaaaa aaaagtcaca      900
tcatcattgc aagaagaccg gcacttggag gaggaactga aatgtcaaga gcaaaaagaa      960
gaacaactgc aagaaggcgt acatagaaaa gaaccacagg gagcaacata g             1011
```

<210> SEQ ID NO 46
<211> LENGTH: 2669
<212> TYPE: DNA
<213> ORGANISM: Artificial sequence
<220> FEATURE:
<223> OTHER INFORMATION: synthetic

<400> SEQUENCE: 46

```
agcctaggcc tccaaaaaag cctcctcact acttctggaa tagctcagag gcagaggcgg       60
cctcggcctc tgcataaata aaaaaaatta gtcagccatg gggcggagaa tgggcggaac      120
tgggcggagt taggggcggg atgggcggag ttaggggcgg gactatggtt gctgactaat      180
tgagatgcat gctttgcata cttctgcctg ctggggagcc tggggacttt ccacacctgg      240
ttgctgacta attgagatgc atgctttgca tacttctgcc tgctggggag cctggggact      300
ttccacaccg gatccaccat gggttcagct attgagcagg atgggttgca tgctggtagt      360
cccgccgcat gggtcgaacg actgtttgga tacgattggg cccaacagac tataggctgt      420
tccgacgctg ctgtctttcg tctttctgca caaggtcgtc cagttctgtt cgtgaaaacc      480
gacttgtccg gagcccctcaa tgagttgcaa gacgaagctg cacgactgag ttggcttgcc      540
accactggtg tcccatgtgc cgcagtactt gacgtcgtca cagaggctgg tcgcgattgg      600
ttgctccttg gagaagtgcc cggccaagat cttctcagtt cccaccttgc ccctgccgaa      660
aaagtttcaa taatggctga cgctatgaga aggctgcaca cccttgaccc tgccacatgt      720
ccattcgatc accaagccaa acaccgaatt gaacgagcta gaaccgcat ggaagccggc       780 ctcgttgatc aagacgattt ggatgaggaa caccagggtc tcgcacccgc tgaactcttc      840
gctcgcctca aagcacgaat gccagacgga gatgacttgg tcgtaaccca cggagatgcc      900
tgccttccta acataatggt agagaatgga agatttagcg gcttcattga ttgtggacga      960 cttgagttg cagatcggta ccaagatatc gctctcgcta ccagagatat tgctgaagaa     1020
ttgggcggag aatgggctga tcggtttctc gtactctacg gaattgccgc acctgattcc     1080
caacgcattg ctttttaccg tcttctggat gagttcttct aaacgcgtcc ccctctccc     1140 tcccccccc ctaacgttac tggccgaagc cgcttggaat aaggccggtg tgcgtttgtc     1200
```

| | |
|---|---|
| tatatgttat tttccaccat attgccgtct tttggcaatg tgagggcccg gaaacctggc | 1260 |
| cctgtcttct tgacgagcat tcctaggggt cttccccctc tcgccaaagg aatgcaaggt | 1320 |
| ctgttgaatg tcgtgaagga agcagttcct ctggaagctt cttgaagaca acaacgtct | 1380 |
| gtagcgaccc tttgcaggca gcggaacccc ccacctggcg acaggtgcct ctgcggccaa | 1440 |
| aagccacgtg tataagatac acctgcaaag gcggcacaac cccagtgcca cgttgtgagt | 1500 |
| tggatagttg tggaaagagt caaatggctc tcctcaagcg tattcaacaa ggggctgaag | 1560 |
| gatgcccaga aggtacccca ttgtatggga tctgatctgg ggcctcggtg cacatgcttt | 1620 |
| acatgtgttt agtcgaggtt aaaaaacgtc taggcccccc gaaccacggg gacgtggttt | 1680 |
| tcctttgaaa aacacgattg ctcgaatcac catggtgagc aagggcgagg agctgttcac | 1740 |
| cggggtggtg cccatcctgg tcgagctgga cggcgacgta aacggccaca gttcagcgt | 1800 |
| gtccggcgag ggcgagggcg atgccaccta cggcaagctg accctgaagt tcatctgcac | 1860 |
| caccggcaag ctgcccgtgc cctggcccac cctcgtgacc accttcggct acggcctgca | 1920 |
| gtgcttcgcc cgctaccccg accacatgaa gcagcacgac ttcttcaagt ccgccatgcc | 1980 |
| cgaaggctac gtccaggagc gcaccatctt cttcaaggac gacggcaact acaagacccg | 2040 |
| cgccgaggtg aagttcgagg gcgacaccct ggtgaaccgc atcgagctga agggcatcga | 2100 |
| cttcaaggag gacggcaaca tcctggggca caagctggag tacaactaca acagccacaa | 2160 |
| cgtctatatc atggccgaca agcagaagaa cggcatcaag gtgaacttca gatccgcca | 2220 |
| caacatcgag gacggcagcg tgcagctcgc cgaccactac cagcagaaca ccccatcgg | 2280 |
| cgacggcccc gtgctgctgc ccgacaacca ctacctgagc taccagtccg ccctgagcaa | 2340 |
| agacccaac gagaagcgcg atcacatggt cctgctggag ttcgtgaccg ccgcgggat | 2400 |
| cactctcggc atggacgagc tgtacaagta atcggccgct aatcagccat accacatttg | 2460 |
| tagaggtttt acttgcttta aaaaacctcc cacacctccc cctgaacctg aaacataaaa | 2520 |
| tgaatgcaat tgttgttgtt aacttgttta ttgcagctta taatggttac aaataaagca | 2580 |
| atagcatcac aaatttcaca aataaagcat ttttttcact gcattctagt tgtggtttgt | 2640 |
| ccaaactcat caatgtatct tatcatgtc | 2669 |

<210> SEQ ID NO 47
<211> LENGTH: 2992
<212> TYPE: DNA
<213> ORGANISM: Artificial sequence
<220> FEATURE:
<223> OTHER INFORMATION: synthetic

<400> SEQUENCE: 47

| | |
|---|---|
| gttgacattg attattgact agttattaat agtaatcaat tacggggtca ttagttcata | 60 |
| gcccatatat ggagttccgc gttacataac ttacggtaaa tggcccgcct ggctgaccgc | 120 |
| ccaacgaccc ccgcccattg acgtcaataa tgacgtatgt tcccatagta acgccaatag | 180 |
| ggactttcca ttgacgtcaa tgggtggagt atttacggta aactgcccac ttggcagtac | 240 |
| atcaagtgta tcatatgcca agtacgcccc ctattgacgt caatgacggt aaatggcccg | 300 |
| cctggcatta tgcccagtac atgaccttat gggactttcc tacttggcag tacatctacg | 360 |
| tattagtcat cgctattacc atggtgatgc ggttttggca gtacatcaat gggcgtggat | 420 |
| agcggtttga ctcacgggga tttccaagtc tccaccccat tgacgtcaat gggagtttgt | 480 |
| tttggcacca aaatcaacgg gactttccaa aatgtcgtaa caactccgcc ccattgacgc | 540 |
| aaatgggcgg taggcgtgta cggtgggagg tctatataag cagagctctc cctatcagtg | 600 |

```
atagagatct ccctatcagt gatagagatc gtcgacgttt agtgaaccgt cagatcgcct    660
ggagacgcca tccacgctgt tttgacctcc atagaagaca ccgggaccga tccagcctcc    720
gcggccggga acggtgcatt ggaacgcgga ttccccgtgc caagagtgac gtaagtaccg    780
cctatagagt ctataggccc accccttgg cttcttatgc atgctatact gttttggct     840
tggggtctat acaccccgc ttcctcatgt tataggtgat ggtatagctt agcctatagg    900
tgtgggttat tgaccattat tgaccactcc cctattggtg acgatacttt ccattactaa    960
tccataacat ggctctttgc cacaactctc tttattggct atatgccaat acactgtcct   1020
tcagagactg acacggactc tgtatttta caggatgggg tctcatttat tatttacaaa   1080
ttcacatata caacaccacc gtccccagtg cccgcagttt ttattaaaca taacgtggga   1140
tctccacgcg aatctcgggt acgtgttccg gacatggtct cttctccggt agcggcggag   1200
cttctacatc cgagccctgc tcccatgcct ccagcgactc atggtcgctc ggcagctcct   1260
tgctcctaac agtggaggcc agacttaggc acagcacgat gcccaccacc accagtgtgc   1320
cgcacaaggc cgtggcggta gggtatgtgt ctgaaaatga gctcggggag cgggcttgca   1380
ccgctgacga atttggaaga cttaaggcag cggcagaaga agatgcaggc agctgagttg   1440
ttgtgttctg ataagagtca gaggtaactc ccgttgcggt gctgttaacg gtggagggca   1500
gtgtagtctg agcagtactc gttgctgccg cgcgcgccac cagacataat agctgacaga   1560
ctaacagact gttcctttcc atgggtcttt tctgcagaag cttatactcg agctctagat   1620
tgggaacccg ggtctctcga attcgagatc tccaccatgc acagacctag acgtcgtgga   1680
actcgtccac ctccactggc actgctcgct gctctcctcc tggctgcacg tggtgctgat   1740
gcagaggtgc agctggtgga gtctggggga gccatagtaa agccggggg gtcccataga   1800
gtctcctgtg aagcctctgg attcactttc agtaacgcct ggatgagttg ggtccgccag   1860
gctccaggga gggggctgga gtgggttggc cgtattttaa gcaagactga tggtgggacg   1920
acagactacg ctgcacccgt gaaagacaga ttcaccattt caagagatga ttctaaaaat   1980
atgttgtttc tgcaaatgga cagcctgaaa atcgaggaca cagccgtgta tttctgtacc   2040
acggccgatt tttggagtgc ttattcttct gactactggg gccagggaac cctggtcacc   2100
gtctcctcag gaggtggagg ttccgggggc ggggctccg gcggaggtgg atcagatatt   2160
gtgatgactc agtctccact ctccctgccc gtcacccctg gagagccggc ctccatctcc   2220
tgcaggtcta gtcagagcct cctgcatagt aatgggtaca actatttgga ttggtaccta   2280
cagaagccag gcagtctcc acaactcctg atctatttgg gttctaatcg ggcctccggg   2340
gtccctgaca ggttcagtgg cagtggatca ggcacagatt ttacactgaa aatcagcaga   2400
atggaggctg aggatgttgg ggtttattac tgcatgcaag gtctacaaac tccgtacact   2460
tttggccagg ggaccaagct ggagatcaaa ggaggcggag ggagtgtttt gttttatctg   2520
gccgttggga taatgtttct cgtaaataca gtactttggg taacaataag gaaggaactg   2580
aagagaaaga aaaatgggga tctggaaata tcattggaca gtggacacga aaaaaaagtc   2640
acatcatcat tgcaagaaga ccggcacttg gaggaggaac tgaaatgtca agagcaaaaa   2700
gaagaacaac tgcaagaagg cgtacataga aaagaaccac agggagcaac ataggcggcc   2760
gctaatcagc cataccacat ttgtagaggt tttacttgct ttaaaaaacc tcccacacct   2820
ccccctgaac ctgaaacata aaatgaatgc aattgttgtt gttaacttgt ttattgcagc   2880
ttataatggt tacaaataaa gcaatagcat cacaaatttc acaaataaag cattttttc    2940
```
actgcattct agttgtggtt tgtccaaact catcaatgta tcttatcatg tc    2992

<210> SEQ ID NO 48
<211> LENGTH: 5765
<212> TYPE: DNA
<213> ORGANISM: Artificial sequence
<220> FEATURE:
<223> OTHER INFORMATION: synthetic

<400> SEQUENCE: 48

```
acaacttcgt atagcataca ttatacgaag ttatggtacc aagcctaggc ctccaaaaaa      60
gcctcctcac tacttctgga atagctcaga ggcagaggcg gcctcggcct ctgcataaat     120
aaaaaaaatt agtcagccat ggggcggaga atgggcggaa ctgggcggag ttaggggcgg     180
gatgggcgga gttaggggcg ggactatggt tgctgactaa ttgagatgca tgctttgcat     240
acttctgcct gctggggagc ctggggactt ccacacctg gttgctgact aattgagatg      300
catgctttgc atacttctgc ctgctgggga gcctggggac tttccacacc ggatccacca     360
tgggttcagc tattgagcag gatgggttgc atgctgtag tcccgccgca tgggtcgaac      420
gactgtttgg atacgattgg gcccaacaga ctataggctg ttccgacgct gctgtctttc     480
gtctttctgc acaaggtcgt ccagttctgt tcgtgaaaac cgacttgtcc ggagccctca     540
atgagttgca agacgaagct gcacgactga gttggcttgc caccactggt gtcccatgtg     600
ccgcagtact tgacgtcgtc acagaggctg gtcgcgattg gttgctcctt ggagaagtgc     660
ccggccaaga tcttctcagt tcccaccttg ccctgccga aaagtttca ataatggctg       720
acgctatgag aaggctgcac acccttgacc ctgccacatg tccattcgat caccaagcca     780
aacaccgaat tgaacgagct agaacccgca tggaagccgg cctcgttgat caagacgatt     840
tggatgagga caccagggt ctcgcacccg ctgaactctt cgctcgcctc aaagcacgaa      900
tgccagacgg agatgacttg gtcgtaaccc acggagatgc ctgccttcct aacataatgg     960
tagagaatgg aagatttagc ggcttcattg attgtggacg acttggagtt gcagatcggt    1020
accaagatat cgctctcgct accagagata ttgctgaaga attgggcgga gaatgggctg    1080
atcggtttct cgtactctac ggaattgccg cacctgattc ccaacgcatt gcttttacc     1140
gtcttctgga tgagttcttc taaacgcgtc ccccctctcc ctccccccc cctaacgtta     1200
ctggccgaag ccgcttggaa taaggccggt gtgcgtttgt ctatatgtta ttttccacca    1260
tattgccgtc ttttggcaat gtgagggccc ggaaacctgg ccctgtcttc ttgacgagca    1320
ttcctagggg tctttcccct ctcgccaaag gaatgcaagg tctgttgaat gtcgtgaagg    1380
aagcagttcc tctggaagct tcttgaagac aaacaacgtc tgtagcgacc ctttgcaggc    1440
agcggaaccc cccacctggc gacaggtgcc tctgcggcca aaagccacgt gtataagata    1500
cacctgcaaa ggcggcacaa ccccagtgcc acgttgtgag ttggatagtt gtggaaagag    1560
tcaaatggct ctcctcaagc gtattcaaca aggggctgaa ggatgcccag aaggtacccc    1620
attgtatggg atctgatctg gggcctcggt gcacatgctt tacatgtgtt tagtcgaggt    1680
taaaaaacgt ctaggccccc cgaaccacgg ggacgtggtt ttcctttgaa aaacacgatt    1740
gctcgaatca ccatggtgag caagggcgag gagctgttca ccggggtggt gcccatcctg    1800
gtcgagctgg acggcgacgt aaacggccac aagttcagcg tgtccggcga gggcgagggc    1860
gatgccacct acggcaagct gaccctgaag ttcatctgca ccaccggcaa gctgcccgtg    1920
ccctggccca ccctcgtgac cacctttcggc tacggcctgc agtgcttcgc ccgctacccc    1980
gaccacatga agcagcacga cttcttcaag tccgccatgc ccgaaggcta cgtccaggag    2040
```

```
cgcaccatct tcttcaagga cgacggcaac tacaagaccc gcgccgaggt gaagttcgag    2100
ggcgacaccc tggtgaaccg catcgagctg aagggcatcg acttcaagga ggacggcaac    2160
atcctggggc acaagctgga gtacaactac aacagccaca acgtctatat catggccgac    2220
aagcagaaga acggcatcaa ggtgaacttc aagatccgcc acaacatcga ggacggcagc    2280
gtgcagctcg ccgaccacta ccagcagaac accccatcg gcgacggccc cgtgctgctg     2340
cccgacaacc actacctgag ctaccagtcc gccctgagca agacccaa cgagaagcgc      2400
gatcacatgg tcctgctgga gttcgtgacc gccgccggga tcactctcgg catggacgag    2460
ctgtacaagt aatcggccgc taatcagcca taccacattt gtagaggttt tacttgcttt    2520
aaaaaacctc ccacacctcc ccctgaacct gaaacataaa atgaatgcaa ttgttgttgt    2580
taacttgttt attgcagctt ataatggtta caaataaagc aatagcatca caaatttcac    2640
aaataaagca ttttttcac tgcattctag ttgtggtttg tccaaactca tcaatgtatc     2700
ttatcatgtc ggcgcgttga cattgattat tgactagtta ttaatagtaa tcaattacgg    2760
ggtcattagt tcatagccca tatatggagt tccgcgttac ataacttacg gtaaatggcc    2820
cgcctggctg accgcccaac gacccccgcc cattgacgtc aataatgacg tatgttccca    2880
tagtaacgcc aatagggact ttccattgac gtcaatgggt ggagtattta cggtaaactg    2940
cccacttggc agtacatcaa gtgtatcata tgccaagtac gccccctatt gacgtcaatg    3000
acggtaaatg gcccgcctgg cattatgccc agtacatgac cttatgggac tttcctactt    3060
ggcagtacat ctacgtatta gtcatcgcta ttaccatggt gatgcggttt tggcagtaca    3120
tcaatgggcg tggatagcgg tttgactcac ggggatttcc aagtctccac cccattgacg    3180
tcaatgggag tttgttttgg caccaaaatc aacgggactt tccaaaatgt cgtaacaact    3240
ccgccccatt gacgcaaatg ggcggtaggc gtgtacggtg ggaggtctat ataagcagag    3300
ctctccctat cagtgataga gatctcccta tcagtgatag agatcgtcga cgtttagtga    3360
accgtcagat cgcctggaga cgccatccac gctgttttga cctccataga agacaccggg    3420
accgatccag cctccgcggc cgggaacggt gcattggaac gcggattccc cgtgccaaga    3480
gtgacgtaag taccgcctat agagtctata ggcccacccc cttggcttct tatgcatgct    3540
atactgtttt tggcttgggg tctatacacc cccgcttcct catgttatag gtgatggtat    3600
agcttagcct ataggtgtgg gttattgacc attattgacc actcccctat tggtgacgat    3660
actttccatt actaatccat aacatggctc tttgccacaa ctctctttat tggctatatg    3720
ccaatacact gtccttcaga gactgacacg gactctgtat ttttacagga tggggtctca    3780
tttattattt acaaattcac atatacaaca ccaccgtccc cagtgcccgc agttttattt    3840
aaacataacg tgggatctcc acgcgaatct cgggtacgtg ttccggacat ggtctcttct    3900
ccggtagcgg cggagcttct acatccgagc cctgctccca tgcctccagc gactcatggt    3960
cgctcggcag ctccttgctc ctaacagtgg aggccagact taggcacagc acgatgccca    4020
ccaccaccag tgtgccgcac aaggccgtgg cggtagggta tgtgtctgaa atgagctcg    4080
gggagcgggc ttgcaccgct gacgcatttg gaagacttaa ggcagcggca gaagaagatg    4140
caggcagctg agttgttgtg ttctgataag agtcagaggt aactcccgtt gcggtgctgt    4200
taacggtgga gggcagtgta gtctgagcag tactcgttgc tgccgcgcgc gccaccagac    4260
ataatagctg acagactaac agactgttcc tttccatggg tcttttctgc agtcaccgtc    4320
cttgacacga agcttatact cgagctctag attgggaacc cgggtctctc gaattcgaga    4380
```

```
tctccaccat gcacagacct agacgtcgtg gaactcgtcc acctccactg gcactgctcg    4440
ctgctctcct cctggctgca cgtggtgctg atgcagaggt gcagctggtg gagtctgggg    4500
gagccatagt aaagccgggg gggtcccata gagtctcctg tgaagcctct ggattcactt    4560
tcagtaacgc ctggatgagt tgggtccgcc aggctccagg gaggggggctg gagtgggttg    4620 gccgtatttt aagcaagact gatggtggga cgacagacta cgctgcaccc gtgaaagaca    4680
gattcaccat ttcaagagat gattctaaaa atatgttgtt tctgcaaatg acagcctga    4740 aaatcgagga cacagccgtg tatttctgta ccacggccga ttttggagt gcttattctt    4800 ctgactactg gggccaggga accctggtca ccgtctcctc aggaggtgga ggttccgggg    4860 gcggggggctc cggcggaggt ggatcagata ttgtgatgac tcagtctcca ctctccctgc    4920
ccgtcacccc tggagagccg gcctccatct cctgcaggtc tagtcagagc ctcctgcata    4980
gtaatgggta caactatttg gattggtacc tacagaagcc agggcagtct ccacaactcc    5040
tgatctattt gggttctaat cgggcctccg ggtccctga caggttcagt ggcagtggat    5100
caggcacaga ttttacactg aaaatcagca gaatggaggc tgaggatgtt ggggtttatt    5160
actgcatgca aggtctacaa actccgtaca cttttggcca ggggaccaag ctggagatca    5220
aaggaggcgg agggagtgtt ttgttttatc tggccgttgg gataatgttt ctcgtaaata    5280
cagtactttg ggtaacaata aggaaggaac tgaagagaaa gaaaaaatgg gatctggaaa    5340
tatcattgga cagtggacac gaaaaaaaag tcacatcatc attgcaagaa gaccggcact    5400
tggaggagga actgaaatgt caagagcaaa aagaagaaca actgcaagaa ggcgtacata    5460
gaaaagaacc acagggagca acataggcgg ccgctaatca gccataccac atttgtagag    5520
gttttacttg ctttaaaaaa cctcccacac ctcccctga acctgaaaca taaaatgaat    5580
gcaattgttg ttgttaactt gtttattgca gcttataatg gttacaaata aagcaatagc    5640
atcacaaatt tcacaaataa agcatttttt tcactgcatt ctagttgtgg tttgtccaaa    5700
ctcatcaatg tatcttatca tgtctaccgg tataacttcg tataatgtat actatacgaa    5760
gttag                                                               5765

<210> SEQ ID NO 49
<211> LENGTH: 660
<212> TYPE: DNA
<213> ORGANISM: Artificial sequence
<220> FEATURE:
<223> OTHER INFORMATION: synthetic

<400> SEQUENCE: 49
gacatcgtga tgacccagtc tccactctcc ctgcccgtca cccctggaga gccggcctcc      60
atctcctgca ggtctagtca gagcctcctg catagtaatg ggtacaacta tttggattgg    120
tacctacaga agccagggca gtctccacaa ctcctgatct atttgggttc taatcgggcc    180
tccggggtcc ctgacaggtt cagtggcagt ggatcaggca cagattttac actgaaaatc    240
agcagaatgg aggctgagga tgttggggtt tattactgca tgcaaggtct acaaactccg    300
tacacttttg gccaggggac caagctggag atcaaacgag ctgatgctgc accaactgta    360
tccatcttcc caccatccag tgagcagtta acatctggag gtgcctcagt cgtgtgcttc    420
ttgaacaact tctaccccaa agacatcaat gtcaagtgga agattgatgg cagtgaacga    480
caaaatggcg tcctgaacag ttggactgat caggacagca agacagcac ctacagcatg    540 agcagcaccc tcacgttgac caaggacgag tatgaacgca taacagcta tacctgtgag    600 gccactcaca gagacatcaac ttcacccatt gtcaagagct caacagggg agagtgttga    660
```

```
<210> SEQ ID NO 50
<211> LENGTH: 1359
<212> TYPE: DNA
<213> ORGANISM: Artificial sequence
<220> FEATURE:
<223> OTHER INFORMATION: synthetic

<400> SEQUENCE: 50
gaggtgcagc tggtggagtc tgggggagcc atagtaaagc cggggggggtc ccatagagtc      60 tcctgtgaag cctctggatt cactttcagt aacgcctgga tgagttgggt ccgccaggct     120
ccagggaggg gctggagtg gttggccgt attttaagca agactgatgg tgggacgaca       180
gactacgctg cacccgtgaa agacagattc accatttcaa gagatgattc taaaaatatg    240
ttgtttctgc aaatggacag cctgaaaatc gaggacacag ccgtgtattt ctgtaccacg    300
gccgattttt ggagtgctta ttcttctgac tactggggcc agggaaccct ggtcaccgtc    360
tcctcagcca aaacaacagc ccatcggtc tatccactgg cccctgtgtg tggagataca     420
actggctcct cggtgactct aggatgcctg gtcaagggtt atttccctga ccagtgacc     480 ttgacctgga actctggatc cctgtccagt ggtgtgcaca ccttcccagc tgtcctgcag    540
tctgacctct acaccctcag cagctcagtg actgtaacct cgagcacctg cccagccag    600 tccatcacct gcaatgtggc ccacccggca agcagcacca aggtggacaa gaaaattgag    660
cccagagggc ccacaatcaa gccctgtcct ccatgcaaat gcccagcacc taacctcttg    720
ggtggaccat ccgtcttcat cttccctcca aagatcaagg atgtactcat gatctccctg    780
agccccatag tcacatgtgt ggtggtggat gtgagcgagg atgacccaga tgtccagatc    840
agctggtttg tgaacaacgt ggaagtacac acagctcaga cacaaaccca tagagaggat    900
tacaacagta ctctccgggt ggtcagtgcc ctccccatcc agcaccagga ctggatgagt    960
ggcaaggagt tcaaatgcaa ggtcaacaac aaagacctcc cagcgcccat cgagagaacc   1020
atctcaaaac ccaaagggtc agtaagagct ccacaggtat atgtcttgcc tccaccagaa   1080
gaagagatga ctaagaaaca ggtcactctg acctgcatgg tcacagactt catgcctgaa   1140
gacatttacg tggagtggac caacaacggg aaaacagagc taaactacaa gaacactgaa   1200
ccagtcctgg actctgatgg ttcttacttc atgtacagca agctgagagt ggaaaagaag   1260
aactgggtgg aaagaaatag ctactcctgt tcagtggtcc acgagggtct gcacaatcac   1320
cacacgacta agagcttctc ccggactccg ggtaaatga                           1359

<210> SEQ ID NO 51
<211> LENGTH: 1011
<212> TYPE: DNA
<213> ORGANISM: Artificial sequence
<220> FEATURE:
<223> OTHER INFORMATION: synthetic

<400> SEQUENCE: 51
gaggtgcagc tggtggagtc tgggggagcc atagtaaagc cggggggggtc ccatagagtc     60 tcctgtgaag cctctggatt cactttcagt aacgcctgga tgagttgggt ccgccaggct    120
ccagggaggg gctggagtg gttggccgt attttaagca agactgatgg tgggacgaca      180
gactacgctg cacccgtgaa agacagattc accatttcaa gagatgattc taaaaatatg   240
ttgtttctgc aaatggacag cctgaaaatc gaggacacag ccgtgtattt ctgtaccacg   300
gccgattttt ggagtgctta ttcttctgac tactggggcc agggaaccct ggtcaccgtc   360
```

-continued

```
tcctcaggag gtggaggttc cggggcggg ggctccggcg gaggtggatc agatattgtg        420
atgactcagt ctccactctc cctgcccgtc acccctggag agccggcctc catctcctgc        480
aggtctagtc agagcctcct gcatagtaat gggtacaact atttggattg gtacctacag        540
aagccagggc agtctccaca actcctgatc tatttgggtt ctaatcgggc ctccggggtc        600
cctgacaggt tcagtggcag tggatcaggc acagatttta cactgaaaat cagcagaatg        660
gaggctgagg atgttggggt ttattactgc atgcaaggtc tacaaactcc gtacactttt        720
ggccagggga ccaagctgga gatcaaagga ggcggaggga gtgttttgtt ttatctggcc        780
gttgggataa tgtttctcgt aaatacagta ctttgggtaa caataaggaa ggaactgaag        840
agaaagaaaa aatgggatct ggaaatatca ttggacagtg gacacgaaaa aaaagtcaca        900
tcatcattgc aagaagaccg gcacttggag gaggaactga aatgtcaaga gcaaaaagaa        960
gaacaactgc aagaaggcgt acatagaaaa gaaccacagg gagcaacata g               1011
```